US008557802B2

(12) United States Patent
Yamanoi et al.

(10) Patent No.: US 8,557,802 B2
(45) Date of Patent: Oct. 15, 2013

(54) AMIDE DERIVATIVE

(75) Inventors: Shigeo Yamanoi, Kanagawa (JP);
Hidenori Namiki, Kanagawa (JP);
Takahiro Katagiri, Tokyo (JP);
Mayuko Akiu, Tokyo (JP); Katsuji Kagechika, Tokyo (JP); Takeshi Honda, Tokyo (JP); Koji Matsumoto, Tokyo (JP); Ryutaro Nakashima, Kanagawa (JP)

(73) Assignee: Daiichi Sankyo Company, Limited, Chuo-ku (JP)

( * ) Notice: Subject to any disclaimer, the term of this patent is extended or adjusted under 35 U.S.C. 154(b) by 11 days.

(21) Appl. No.: 13/388,210

(22) PCT Filed: Aug. 4, 2010

(86) PCT No.: PCT/JP2010/063149
§ 371 (c)(1),
(2), (4) Date: Jan. 31, 2012

(87) PCT Pub. No.: WO2011/016469
PCT Pub. Date: Feb. 10, 2011

(65) Prior Publication Data
US 2012/0129832 A1    May 24, 2012

(30) Foreign Application Priority Data
Aug. 5, 2009  (JP) ................. 2009-182720

(51) Int. Cl.
A61K 31/4245  (2006.01)
C07D 413/10   (2006.01)
C07D 413/12   (2006.01)
C07D 413/14   (2006.01)

(52) U.S. Cl.
USPC ............ 514/210.18; 514/236.2; 514/364; 548/131

(58) Field of Classification Search
CPC ............. A61K 31/4245; C07D 413/10
See application file for complete search history.

(56) References Cited

FOREIGN PATENT DOCUMENTS

| WO | 97/46556 A1 | 12/1997 |
| WO | 02/16332 A1 | 2/2002 |
| WO | 2005/116016 A1 | 12/2005 |
| WO | 2007/116229 A1 | 10/2007 |

OTHER PUBLICATIONS

Schafer et al. Drug Discovery Today, 2008, 13 (21/22), 913-916.*
Horig et al. Journal of Translational Medicine 2004, 2(44), p. 1-8.*
Extended European Search Report mailed Nov. 14, 2012, issued in corresponding Application No. EP 10 80 6468.4, filed Aug. 4, 2010, 6 pages.
International Search Report mailed Sep. 7, 2010, issued in corresponding International Application No. PCT/JP2010/063149, filed Aug. 4, 2010, 2 pages.

* cited by examiner

*Primary Examiner* — Yong Chu
(74) *Attorney, Agent, or Firm* — Christensen O'Connor Johnson Kindness PLLC

(57) ABSTRACT

Provided are a compound having an excellent hypoglycemic action, or a pharmaceutically acceptable salt thereof, and a pharmaceutical composition having an excellent therapeutic effect and/or prophylactic effect on type 1 diabetes, type 2 diabetes, and the like, which cause an increase in the blood sugar level due to abnormal sugar metabolism. A compound represented by general formula (I), or a pharmaceutically acceptable salt thereof, is disclosed.

22 Claims, No Drawings

AMIDE DERIVATIVE

TECHNICAL FIELD

The present invention relates to a novel amide derivative having a hypoglycemic action and/or a β cell- or pancreas-protecting action, or a pharmaceutically acceptable salt thereof, and to a pharmaceutical composition containing these as active ingredients.

BACKGROUND ART

Diabetes mellitus is a metabolic disease primarily characterized by a chronic hyperglycemic state due to a lack of insulin action. The treatment of diabetes is generally by drug therapy together with diet therapy and exercise therapy. Examples of oral hypoglycemic agents in use, which are a class of therapeutic drugs for diabetes, include biguanide agents and thiazolidinedione agents that improve insulin resistance; sulfonylurea agents and glinide drugs that promote insulin secretion from pancreatic β cells; and α-glucosidase inhibitors that inhibit sugar absorption.

However, it is reported that biguanide agents have adverse side effects such as digestive symptoms and lactic acidosis; thiazolidinedione agents have adverse side products such as weight gain and edema; sulfonylurea agents and glinide drugs have adverse side effects such as hypoglycemia or secondary failure due to long-term use; and α-glucosidase inhibitors have adverse side effects such as diarrhea. Therefore, development of an oral hypoglycemic agent which can address such problems is desired.

Furthermore, in recent years, piperidine compounds have been developed as oral hypoglycemic agents having new structures (see, for example, Patent Literatures 1 to 4).

CITATION LIST

Patent Literatures

Patent Literature 1: WO 07/116,229
Patent Literature 2: WO 07/003,960
Patent Literature 3: WO 07/003,962
Patent Literature 4: WO 05/061489

SUMMARY OF THE INVENTION

Technical problem

However, the compounds described in the above-described patent literatures have a problem in that a sufficient hypoglycemic action and a β cell- or pancreas-protecting action cannot be easily obtained. Furthermore, the patent literatures described above disclose compounds containing a cyclohexane ring or a piperidine ring in their structures, but neither describe nor suggest any compounds containing a benzene ring, a pyridine ring or a pyridazine ring in their structures, instead of a cyclohexane ring or a piperidine ring. Thus, an object of the present invention is to provide compounds which have a new structure that is neither described nor suggested in the above patent literatures and has an excellent hypoglycemic action and a β cell- or pancreas-protecting action, or a pharmaceutically acceptable salt thereof; a pharmaceutical composition having an excellent therapeutic effect and/or prophylactic effect on type 1 diabetes, type 2 diabetes and the like, which cause an increase in the blood sugar level due to abnormal sugar metabolism; and a pharmaceutical composition having a β cell- or pancreas-protecting action.

Solution to Problem

The present invention provides:
(1) A compound represented by general formula (I):

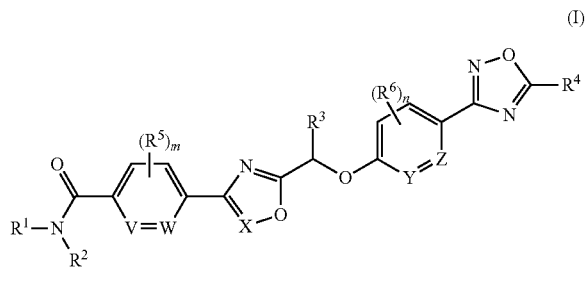

wherein $R^1$ represents a hydrogen atom, or a C1-C6 alkyl group substituted with one or two substituents selected from a substituent subgroup α;

the substituent subgroup α is the group consisting of a C1-C6 alkoxy group, a C1-C6 alkoxycarbonyl group, a hydroxyl group which may be substituted with a substituent selected from a substituent subgroup β, and a carboxyl group;

the substituent subgroup β is the group consisting of a C1-C6 alkylcarbonyl group substituted with one or two substituents selected from a substituent subgroup γ, and a 4- to 6-membered heterocyclic carbonyl group which may be substituted with one C1-C6 alkyl group;

the substituent subgroup γ is the group consisting of a hydroxyl group, an amino group, a (C1-C6 alkyl)amino group, a di(C1-C6 alkyl)amino group, a carbamoyl group, a phenyl group and a 4- to 6-membered heterocyclic group;

$R^2$ represents a hydrogen atom, or a C1-C6 alkyl group which may be substituted with one hydroxyl group;

or $R^1$ and $R^2$, together with the nitrogen atom to which $R^1$ and $R^2$ are bonded, may be joined to form an azetidino group, a pyrrolidino group or a morpholino group, wherein the azetidino group, pyrrolidino group or morpholino group may be substituted with one hydroxyl group or one hydroxy-C1-C6 alkyl group;

$R^3$ and $R^4$ each independently represent a C1-C6 alkyl group;

$R^5$ represents a halogen atom or a C1-C6 alkyl group;

$R^6$ represents a halogen atom;

m and n each independently represent an integer from 0 to 4; and

V, W, X, Y and Z each independently represent CH or N, or a pharmaceutically acceptable salt thereof;

(2) the compound as set forth in item (1), wherein Y and Z both represent CH;

(3) the compound as set forth in item (1) or (2), wherein V and W both represent CH;

(4) the compound as set forth in any one of items (1) to (3), wherein X represents N;

(5) the compound as set forth in any one of items (1) to (4), wherein $R^1$ represents a C1-C4 alkyl group substituted with one or two hydroxyl groups;

(6) the compound as set forth in any one of items (1) to (4), wherein $R^1$ represents a hydroxyethyl group, a hydroxyisopropyl group, a hydroxy-1,1-dimethylethyl group or a 2-hydroxy-1-(hydroxymethyl)ethyl group;

(7) the compound as set forth in any one of items (1) to (4), wherein $R^1$ represents a C1-C4 alkyl group substituted with one substituent selected from the substituent subgroup α, wherein the substituent subgroup α is a hydroxyl group substituted with one substituent selected from the substituent subgroup β, the substituent subgroup β is a C1-C4 alkylcarbonyl group substituted with one substituent selected from the substituent subgroup γ, and the substituent subgroup γ is an amino group;

(8) the compound as set forth in any one of items (1) to (4), wherein $R^4$ represents an aminomethylcarbonyloxyethyl group, an aminomethylcarbonyloxyisopropyl group or an aminomethylcarbonyloxy-1,1-dimethylethyl group;

(9) the compound as set forth in any one of items (1) to (8), wherein $R^2$ represents a hydrogen atom;

(10) the compound as set forth in any one of items (1) to (9), wherein $R^3$ represents a C1-C3 alkyl group;

(11) the compound as set forth in any one of items (1) to (9), wherein $R^3$ represents an ethyl group;

(12) the compound as set forth in any one of items (1) to (11), wherein $R^4$ represents a C1-C3 alkyl group;

(13) the compound as set forth in any one of items (1) to (11), wherein $R^4$ represents an ethyl group or an isopropyl group;

(14) the compound as set forth in any one of items (1) to (13), wherein $R^5$ represents a halogen atom, and m represents 1;

(15) the compound as set forth in any one of items (1) to (13), wherein $R^5$ represents a fluorine atom, and m represents 1;

(16) the compound as set forth in any one of items (1) to (15), wherein n represents 0;

(17) a compound selected from the group consisting of the following compounds:
2-fluoro-N-(2-hydroxyethyl)-4-(5-{1-[4-(5-isopropyl-1,2,4-oxadiazol-3-yl)phenoxy]propyl}-1,2,4-oxadiazol-3-yl)benzamide,
2-fluoro-N-[(1R)-2-hydroxy-1-methylethyl]-4-(5-{1-[4-(5-isopropyl-1,2,4-oxadiazol-3-yl)phenoxy]propyl}-1,2,4-oxadiazol-3-yl)benzamide,
2-fluoro-N-(2-hydroxy-1,1-dimethylethyl)-4-(5-{1-[4-(5-isopropyl-1,2,4-oxadiazol-3-yl)phenoxy]propyl}-1,2,4-oxadiazol-3-yl)benzamide,
(2R)-2-{[2-fluoro-4-(5-{1-[4-(5-isopropyl-1,2,4-oxadiazol-3-yl)phenoxy]propyl}-1,2,4-oxadiazol-3-yl)benzoyl] amino}propyl glycinate hydrochloride,
2-{[2-fluoro-4-(5-{1-[4-(5-isopropyl-1,2,4-oxadiazol-3-yl) phenoxy]propyl}-1,2,4-oxadiazol-3-yl)benzoyl]amino}-2-methylpropyl glycinate hydrochloride,
2-fluoro-N-[(1S)-2-hydroxy-1-methylethyl]-4 (2-{1-[4 (5 isopropyl-1,2,4-oxadiazol-3-yl)phenoxy]propyl}-1,3-oxazol-4-yl)benzamide,
(2S)-2-{[2-fluoro-4 (2-{1-[4 (5 isopropyl-1,2,4-oxadiazol-3-yl)phenoxy]propyl}-1,3-oxazol-4-yl)benzoyl] amino}propyl glycinate hydrochloride,
4-(5-{1-[4-(5-ethyl-1,2,4-oxadiazol-3-yl)phenoxy]propyl}-1,2,4-oxadiazol-3-yl)-2-fluoro-N-[(1S)-2-hydroxy-1-methylethyl]benzamide,
(2S)-2-{[4-(5-{1-[4-(5-ethyl-1,2,4-oxadiazol-3-yl)phenoxy] propyl}-1,2,4-oxadiazol-3-yl)-2-fluorobenzoyl] amino}propyl glycinate hydrochloride,
2-fluoro-N-[(1R)-2-hydroxy-1-methylethyl]-4-(5-{(1R)-1-[4-(5-isopropyl-1,2,4-oxadiazol-3-yl)phenoxy]propyl}-1,2,4-oxadiazol-3-yl)benzamide, and
N-(cyclopropylmethyl)-2-fluoro-4-(5-{(1R)-1-[4-(5-isopropyl-1,2,4-oxadiazol-3-yl)phenoxy]propyl}-1,2,4-oxadiazol-3-yl)benzamide;

(18) a pharmaceutical composition comprising, as an active ingredient, the compound as set forth in any one of items (1) to (17), or a pharmaceutically acceptable salt thereof;

(19) the pharmaceutical composition as set forth in item (18), for treating and/or preventing type 1 diabetes mellitus, type 2 diabetes mellitus, a diabetes-associated disease, or obesity;

(20) the pharmaceutical composition as set forth in item (18), for protecting β cells or the pancreas;

(21) use of the compound as set forth in any one of items (1) to (17) or a pharmaceutically acceptable salt thereof, for preparing a pharmaceutical composition;

(22) a method for treating and/or preventing a disease, the method including administering to a mammal a pharmacologically effective amount of the compound as set forth in any one of items (1) to (17) or a pharmaceutically acceptable salt thereof;

(23) the method as set forth in item (22), wherein the disease is type 1 diabetes mellitus, type 2 diabetes mellitus, a diabetes-associated disease, or obesity;

(24) a method for protecting β cells or pancreas, the method including administering to a mammal a pharmacologically effective amount of the compound as set forth in any one of items (1) to (17) or a pharmaceutically acceptable salt thereof; and

(25) the method as set forth in any one of items (22) to (24), wherein the mammal is a human being.

Advantageous Effects of Invention

According to the present invention, there can be provided an oxadiazole compound having an excellent hypoglycemic action, or a pharmaceutically acceptable salt thereof, a pharmaceutical composition having an excellent therapeutic effect and/or prophylactic effect on type 1 diabetes, type 2 diabetes and the like, which cause an increase in the blood sugar level, and a pharmaceutical composition having a β cell- or pancreas-protecting effect.

DESCRIPTION OF EMBODIMENTS

A "C1-C6 alkyl group" as used in the present specification means a linear, branched or cyclic alkyl group having 1 to 6 carbon atoms. Specific examples include a methyl group, an ethyl group, a propyl group, an isopropyl group, a cyclopropyl group, a butyl group, an isobutyl group, a sec-butyl group, a tert-butyl group, a pentyl group, a 1,2-dimethylpropyl group, an isopentyl group, a hexyl group, and an isohexyl group.

A "C1-C6 alkyl group substituted with one or two substituents" as used in the present specification means a group obtained by substituting one or two hydrogen atoms of a "C1-C6 alkyl group" with identical or different substituents.

A "C1-C6 alkoxy group" as used in the present specification means a group in which a "C1-C6 alkyl group" is bonded to an oxygen atom. Specific examples include a methoxy group, an ethoxy group, a propoxy group, a butoxy group, a pentyloxy group, and a hexyloxy group.

A "C1-C6 alkoxycarbonyl group" as used in the present specification means a group in which a "C1-C6 alkoxy group" is bonded to a carbonyl group. Specific examples include a methoxycarbonyl group, an ethoxycarbonyl group, a propoxycarbonyl group, a butoxycarbonyl group, a pentyloxycarbonyl group, and a hexyloxycarbonyl group.

A "C1-C6 alkylcarbonyl group" as used in the present specification means a group in which a "C1-C6 alkyl group"

is bonded to a carbonyl group. Specific examples include a methylcarbonyl group, an ethylcarbonyl group, a propylcarbonyl group, an isopropylcarbonyl group, a butylcarbonyl group, an isobutylcarbonyl group, a sec-butylcarbonyl group, and a tert-butylcarbonyl group.

A "hydroxyl group which may be substituted with a substituent" as used in the present specification means a hydroxyl group, or a group obtained by substituting the hydrogen atom of a hydroxyl group with a substituent.

A "C1-C6 alkylcarbonyl group substituted with one or two substituents" as used in the present specification means a group obtained by substituting one or two hydrogen atoms of the "C1-C6 alkyl group" in a "C1-C6 alkylcarbonyl group", with identical or different substituents.

A "4- to 6-membered heterocyclic group" as used in the present specification means a 4- to 6-membered saturated monocyclic or unsaturated monocyclic, monovalent group containing 1 to 3 heteroatoms selected from the group consisting of an oxygen atom, a nitrogen atom and a sulfur atom. Specific examples include a furanyl group, a tetrahydrofuranyl group, a pyranyl group, a tetrahydropyranyl group, a thienyl group, a thiopyranyl group, a pyrrolyl group, a pyrrolidinyl group, an imidazolyl group, an imidazolidinyl group, a pyrazolyl group, a pyrazolidinyl group, a thiazolyl group, a thiazolidinyl group, an isothiazolyl group, an isothiazolidinyl group, an oxazolyl group, an oxazolidinyl group, an isoxazolyl group, an isoxazolidinyl group, a pyridinyl group, a piperidinyl group, a pyrazinyl group, a piperazinyl group, a pyrimidinyl group, a pyridazinyl group, a thiomorpholinyl group, and a morpholinyl group.

A "4- to 6-membered heterocyclic carbonyl group" as used in the present specification means a group in which a "4- to 6-membered heterocyclic group" is bonded to a carbonyl group. Specific examples include a pyrrolidin-1-ylcarbonyl group, a pyrrolidin-2-ylcarbonyl group, an imidazolidin-2-ylcarbonyl group, and a morpholin-4-ylcarbonyl group.

A "4- to 6-membered heterocyclic carbonyl group which may be substituted with one C1-C6 alkyl group" as used in the present specification means a "4- to 6-membered heterocyclic carbonyl group", or a group obtained by substituting one hydrogen of a "4- to 6-membered heterocyclic carbonyl group" with a "C1-C6 alkyl group".

A "(C1-C6 alkyl)amino group" as used in the present specification means a group obtained by substituting one hydrogen atom of an amino group, with a "C1-C6 alkyl group". Specific examples include a methylamino group, an ethylamino group, a propylamino group, an isopropylamino group, a butylamino group, an isobutylamino group, a sec-butylamino group, and a tert-butylamino group.

A "di(C1-C6 alkyl)amino group" as used in the present specification means a group obtained by substituting two hydrogen atoms of an amino group, with "C1-C6 alkyl" groups which may be identical with or different from each other. Specific examples include an N,N-dimethylamino group, an N,N-diethylamino group, an N,N-dipropylamino group, a diisopropylamino group, an N,N-dibutylamino group, an N-methyl-N-ethylamino group, an N-methyl-N-propylamino group, and an N-ethyl-N-propylamino group.

A "halogen atom" as used in the present specification means a fluorine atom, a chlorine atom, a bromine atom, or an iodine atom.

A "C1-C6 alkylene group" as used in the present specification means a divalent group obtained by removing one hydrogen atom from a "C1-C6 alkyl group". Specific examples include a methylene group, an ethylene group, a propylene group, a butylene group, a pentylene group, and a hexylene group.

A "pharmaceutically acceptable salt" as used in the present specification means a salt formed by allowing the compound of the present invention to react with an acid or a base.

Examples of the salt include hydrohalogenic acid salts such as hydrofluorides, hydrochlorides, hydrobromides, and hydroiodides; inorganic acid salts such as hydrochlorides, nitrates, perchlorates, sulfates and phosphates; lower alkanesulfonic acid salts such as methanesulfonates, trifluoromethanesulfonates, and ethanesulfonates; arylsulfonic acid salts such as benzenesulfonates, and p-toluenesulfonates; organic acid salts such as acetates, malates, fumarates, succinates, citrates, ascorbates, tartrates, oxalates, and maleates; alkali metal salts such as sodium salts, potassium salts, and lithium salts; alkaline earth metal salts such as calcium salts and magnesium salts; metal salts such as aluminum salts and iron salts; inorganic salts such as ammonium salts; amine salts including organic salts such as t-octylamine salts, dibenzylamine salts, morpholine salts, glucosamine salts, phenylglycine alkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzylphenethylamine salts, piperazine salts, tetramethylammonium salts, and tris(hydroxymethyl)aminomethane salts; and amino acid salts such as glycine salts, lysine salts, arginine salts, ornithine salts, glutamates, and aspartates.

The compound of the present invention absorbs water when, for example, left to stand in the atmosphere or the like, so that adsorbed water may adhere to the compound and a hydrate may be formed. Therefore, such hydrates are also included in the concept of the salt of the present invention.

Since the compound of the present invention may have asymmetric carbon atoms in the molecule, the compound has optical isomers. These isomers and mixtures of these isomers are all represented by a single formula, that is, the general formula (I). Therefore, the present invention encompasses all of the optical isomers of the compound represented by the general formula (I), and mixtures of these optical isomers in any ratios. Such an optical isomer can be produced by, for example, using raw materials having optical activity instead of the raw materials used in the production methods, Reference Examples and Examples that will be described below, or can be obtained by subjecting a compound that has been produced by making reference to the production methods, Reference Examples, Examples and the like that will be described below, to an optical resolution method that is known in the relevant art, for example, a diastereomer method, an enzymatic reaction method, or an optical resolution method based on chromatography.

The present invention may also encompass compounds in which one or more of the atoms constituting the compound represented by the general formula (I) have been substituted with isotopes of the atoms. Isotopes include two classes such as radioactive isotopes and stable isotopes, and examples of the isotopes include, for example, isotopes of hydrogen ($^{2}H$ and $^{3}H$), isotopes of carbon ($^{11}C$, $^{13}C$ and $^{14}C$), isotopes of nitrogen ($^{13}N$ and $^{15}N$), isotopes of oxygen ($^{15}O$, $^{17}O$ and $^{18}O$), and isotopes of fluorine ($^{18}F$). A composition containing a compound labeled with an isotope is useful as, for example, a therapeutic agent, a prophylactic agent, a research reagent, an assay reagent, a diagnostic agent, or an in vivo diagnostic imaging agent. Compounds labeled with isotopes and mixtures of compounds labeled with isotopes in any ratios are all included in the present invention. A compound labeled with an isotope can be produced by methods known in the relevant art, for example, using raw materials labeled with isotopes instead of the raw materials used in the production methods of the present invention that will be described below.

The present invention may also encompass prodrugs of the compound represented by the general formula (I). A prodrug is a derivative of the compound represented by the general formula (I), and means a compound which is enzymatically or chemically converted to the compound of the present invention in the living body.

Examples of the prodrug include compounds in which an amino group in the molecule has been acylated, alkylated or phosphorylated; compounds in which a carboxyl group in the molecule has been esterified or amidated; and compounds in which a hydroxyl group in the molecule has been acylated, alkylated or phosphorylated (see, for example, Povl Krogsgaard-Larsen, et al., "A Textbook of Drug Design and Development", Second Edition, Harwood Academic Publishers, 1996, pp. 351-385). Such a prodrug can be produced from the compound represented by the general formula (I) by methods known in the relevant art.

V preferably represents CH.
W preferably represents CH.
X preferably represents N.
Y preferably represents CH.
Z preferably represents CH.
$R^1$ preferably represents a hydrogen atom, or a C1-C4 alkyl group substituted with one substituent selected from the substituent subgroup α; and more preferably represents a hydrogen atom, an ethyl group substituted with one substituent selected from the substituent subgroup α, a propyl group substituted with one substituent selected from the substituent subgroup α, an isopropyl group substituted with one substituent selected from the substituent subgroup α, an isobutyl group substituted with one substituent selected from the substituent subgroup α, a sec-butyl group, a tert-butyl group substituted with one substituent selected from the substituent subgroup α, or a 1,1-dimethylethyl group substituted with one substituent selected from the substituent subgroup α.

The substituent subgroup α is preferably a C1-C3 alkoxy group, and a hydroxyl group which may be substituted with a substituent selected from the substituent subgroup β; and more preferably a methoxy group, a hydroxyl group, and a hydroxyl group substituted with a substituent selected from the substituent subgroup β.

The substituent subgroup β is preferably a C1-C3 alkylcarbonyl group substituted with one or two substituents selected from the substituent subgroup γ, and a 5-membered heterocyclic carbonyl group which may be substituted with one C1-C3 alkyl group; and more preferably a methylcarbonyl group substituted with a substituent selected from the substituent subgroup γ, and a pyrrolidinecarbonyl group.

The substituent subgroup γ is preferably a hydroxyl group, an amino group, and a di(C1-C3 alkyl)amino group; and more preferably a hydroxyl group, an amino group, and a di(methyl)amino group.

$R^2$ is even more preferably a C1-C4 alkyl group substituted with one hydroxyl group, or a C1-C4 alkyl group substituted with one hydroxyl group that is substituted with one C1-C4 alkylcarbonyl group that is substituted with one amino group; and particularly preferably a hydroxyethyl group, a hydroxyisopropyl group, a hydroxy-1,1-dimethyl-ethyl group, an aminomethylcarbonyloxyethyl group, an aminomethylcarbonyloxyisopropyl group, or an aminomethylcarbonyloxy-1,1-dimethyl-ethyl group.

$R^2$ preferably represents a hydrogen atom or a C1-C3 alkyl group; and more preferably a hydrogen atom or a methyl group.

$R^3$ preferably represents a C1-C3 alkyl group; and more preferably a methyl group or an ethyl group.

$R^4$ preferably represents a C1-C3 alkyl group; and more preferably an ethyl group or an isopropyl group.

$R^5$ preferably represents a halogen atom or a C1-C3 alkyl group; and more preferably a fluorine atom or a methyl group.

m preferably represents 0 or 1; and more preferably 1.

$R^6$ preferably represents a halogen atom; and more preferably a bromine atom.

n preferably represents 0 or 1; and more preferably 0.

A preferred combination of V, W, X, Y, Z, $R^1$, $R^2$, $R^3$, $R^4$, $R^5$, $R^6$, m and n in the general formula (I) is the combination in which V is CH; W is CH; X is N; Y is CH; Z is CH; $R^2$ is a C1-C4 alkyl group substituted with one hydroxyl group, or a C1-C4 alkyl group substituted with one hydroxyl group that is substituted with one C1-C4 alkylcarbonyl group that is substituted with one amino group; $R^2$ is a hydrogen atom; $R^3$ is a C1-C3 alkyl group; $R^4$ is a C1-C3 alkyl group; $R^5$ is a halogen atom; m is 1; and n is 0.

A more preferred combination is the combination in which V is CH; W is CH; X is N; Y is CH; Z is CH; $R^2$ is a hydroxyethyl group, a hydroxyisopropyl group, a hydroxy-1,1-dimethyl-ethyl group, an aminomethylcarbonyloxyethyl group, an aminomethylcarbonyloxyisopropyl group, or an aminomethylcarbonyloxy-1,1-dimethyl-ethyl group; $R^2$ is a hydrogen atom; $R^3$ is an ethyl group; $R^4$ is a C1-C3 alkyl group; $R^5$ is a halogen atom; m is 1; and n is 0.

The compound of the present invention can be produced by, for example, the following methods A to C. In addition, for the benzene-based compounds, pyridine-based compounds, pyridazine-based compounds or amino-based compounds that are used as the starting raw materials in the following production methods, commercially available compounds can be used.

Method A is a method for producing a compound (Ia) of the present invention represented by the general formula (I), in which X is N; and $R^2$ is a hydrogen atom, or a C1-C6 alkyl group substituted with one or two substituents selected from a substituent subgroup α', wherein the substituent subgroup α' is the group consisting of a C1-C6 alkoxy group, a C1-C6 alkoxycarbonyl group, a hydroxyl group and a carboxyl group.

Method B is a method for producing a compound (Ib) of the present invention represented by the general formula (I), in which X is CH; and $R^1$ is a hydrogen atom, or a C1-C6 alkyl group substituted with one or two substituents selected from the substituent subgroup α', wherein the substituent subgroup α' has the same meaning as defined above.

Method C is a method for producing a compound (Ic) of the present invention represented by the general formula (I), in which $R^1$ is a C1-C6 alkyl group substituted with one hydroxyl group substituted with a substituent selected from the substituent subgroup β.

In the reactions of the various steps of the methods described below, when a compound serving as a reaction substrate has a group which inhibits the intended reaction (for example, an amino group, a hydroxyl group, or a carboxyl group), introduction of a protective group to such a group and removal of the introduced protective group may be carried out as necessary. There are no particular limitations on these protective groups as long as they are conventionally used protective groups, but examples include those protective groups described in T. H. Greene, P. G. Wuts, Protective Groups in Organic Synthesis. Third Edition, 1999, John Wiley & Sons, Inc., or the like. The reaction for introducing these protective groups and the reaction for removing the protective groups can be carried out according to routine methods, such as the methods described in the literature mentioned above.

Explanations of the various steps in methods A to C will be described below.

Method A

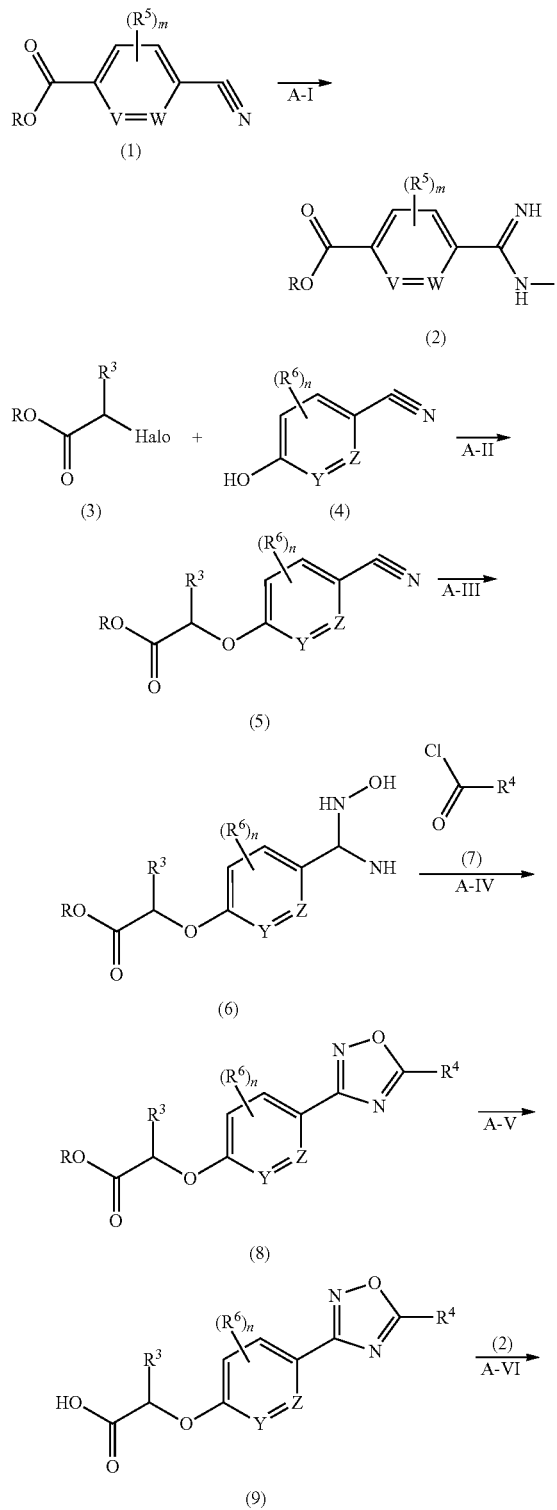

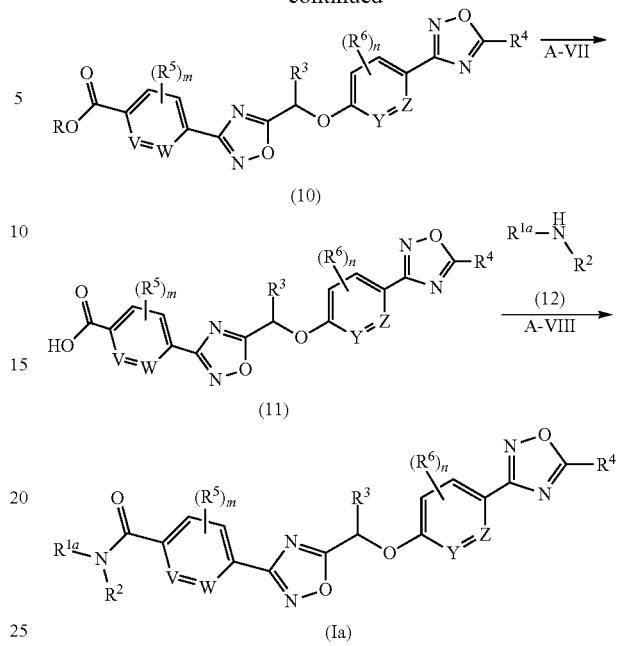

wherein R is a protective group of a carboxyl group; Halo represents a halogen atom; $R^{1a}$ represents a hydrogen atom, or a C1-C6 alkyl group substituted with one or two substituents selected from the substituent subgroup α'; V, W, Y, Z, $R^2$, $R^3$, $R^4$, $R^5$, $R^6$, m, n and α' respectively have the same meanings as defined above.

Step A-I is a step for producing a compound (2) by allowing a compound (I) to react with hydroxylamine.

Examples of a solvent used therein include methanol, ethanol, a methanol/toluene mixed solvent, dimethylformamide (DMF) and dimethyl sulfoxide, and a preferred example is ethanol.

Examples of hydroxylamine used therein include a 50 w/w % aqueous solution of hydroxylamine and hydroxylamine hydrochloride, and a preferred example is a 50 w/w % aqueous solution of hydroxylamine.

Examples of a reagent used therein include sodium carbonate, potassium carbonate, cesium carbonate, potassium tert-butoxide, triethylamine, and diisopropylethylamine.

The reaction temperature is 0° C. to 150° C., and preferably 50° C. to 100° C. The reaction time is 10 minutes to 24 hours, and preferably 30 minutes to 5 hours.

When a workup is needed, the workup may be carried out according to the following procedure, for example. The reaction mixture is cooled to room temperature, subsequently the solvent is distilled off under reduced pressure, and the resulting residue is washed with hexane.

Step A-II is a step for producing a compound (5) by allowing a compound (3) to react with a compound (4) in the presence of a base.

Examples of a solvent used therein include tetrahydrofuran (THF), 1,4-dioxane, acetonitrile and acetone, and a preferred example is acetonitrile.

Examples of the base used therein include sodium carbonate, potassium carbonate, cesium carbonate, potassium tert-butoxide and sodium hydroxide, and a preferred example is potassium carbonate.

The reaction temperature is 0° C. to 150° C., and preferably 20° C. to 130° C. The reaction time is 30 minutes to 24 hours, and preferably 30 minutes to 6 hours.

When a workup is needed, the workup may be carried out according to the following procedure, for example. The reaction mixture is cooled to room temperature, and then the insoluble matter is removed by using Celite. The solvent is distilled off under reduced pressure from the reaction mixture from which the insoluble matter has been removed. The resulting residue is purified by silica gel chromatography, or is washed with an organic solvent, water or the like.

Step A-III is a step for producing a compound (6) by allowing the compound (5) obtained in step A-II to react with hydroxylamine.

Examples of a solvent used therein include the same solvents as the solvents used in step A-I, and a preferred example is ethanol.

Examples of hydroxylamine used therein include the same hydroxylamines as the hydroxylamines used in step A-I, and a preferred example is a 50 w/w % aqueous solution of hydroxylamine.

Examples of a reagent used therein include the same reagents as the reagents used in step A-I.

The reaction temperature is 0° C. to 150° C., and preferably 50° C. to 100° C. The reaction time is 10 minutes to 24 hours, and preferably 30 minutes to 5 hours.

When a workup is needed, the workup may be carried out according to the following procedure, for example. The reaction mixture is cooled to room temperature, subsequently the solvent is distilled off under reduced pressure, and the resulting residue is washed with hexane.

Step A-IV is a step for producing an oxadiazole compound (8) by allowing the compound (6) obtained in step A-III to react with an acid halide (7).

Examples of a solvent used therein include THF, DMF, toluene and pyridine, and a preferred example is pyridine.

Examples of a reagent used therein include pyridine, triethylamine, diisopropylethylamine, and sodium hydride.

The reaction temperature is 20° C. to 150° C., and preferably 40° C. to 100° C. The reaction time is 30 minutes to 24 hours, and preferably 30 minutes to 10 hours.

When a workup is needed, the workup may be carried out according to the following procedure, for example. A saturated ammonium chloride solution, water or saturated brine is added to the reaction mixture, the product is extracted using an organic solvent such as ethyl acetate, and the organic layer thus obtained is dried over sodium sulfate. After the insoluble matter is removed, the solvent is distilled off under reduced pressure.

Step A-V is a step for producing a compound (9) by hydrolyzing the compound (8) obtained in step A-IV.

Examples of a solvent used therein include THF, methanol, ethanol and isopropyl alcohol, and a preferred example is methanol.

Examples of a reagent used therein include an aqueous solution of sodium hydroxide, an aqueous solution of potassium hydroxide and an aqueous solution of lithium hydroxide, and a preferred example is an aqueous solution of sodium hydroxide.

The reaction temperature is 0° C. to 130° C., and preferably 20° C. to 70° C. The reaction time is 30 minutes to 12 hours, and preferably 30 minutes to 4 hours.

When a workup is needed, the workup may be carried out according to the following procedure, for example. An acid such as hydrochloric acid is added to the reaction mixture to make the reaction mixture acidic or neutral, and the product is extracted using an organic solvent such as ethyl acetate. The organic layer thus obtained is dried over a desiccant such as sodium sulfate. The insoluble matter is removed, and then the solvent is distilled off under reduced pressure.

Step A-VI is a step for producing a compound (10) by allowing the compound (2) obtained in step A-I to react with the compound (9) obtained in step A-V.

Examples of a solvent used therein include 3-dimethyl-2-imidazolidinone, and DMF.

Examples of a reagent used therein include 1-(3-dimethylaminopropyl)-3-ethylcarbodiimide, and 1-hydroxybenzotriazole.

The reaction temperature is 30° C. to 130° C., and preferably 50° C. to 70° C. The reaction time is 30 minutes to 12 hours, and preferably 30 minutes to 6 hours.

When a workup is needed, the workup may be carried out according to the following procedure, for example. Water is added to the reaction mixture, and then the product is extracted using an organic solvent such as ethyl acetate. The organic layer thus obtained is washed with water, saturated brine or the like, and is dried over a desiccant such as sodium sulfate. The solvent is distilled off under reduced pressure, and the residue is purified by silica gel chromatography.

Step A-VII is a step for producing a compound (11) by hydrolyzing the compound (10) obtained in step A-VI.

The solvent, reagent, reaction temperature, reaction time, and workup used therein are the same as those used in step A-V.

Step A-VIII is a step for producing the compound (Ia) of the present invention by allowing the compound (11) obtained in step A-VII to react with an amine compound (12) in the presence of a condensing agent.

Examples of a solvent used therein include methylene chloride, tetrahydrofuran, 1,4-dioxane, DMF, and dimethylacetamide. Preferred examples include methylene chloride and DMF, and a more preferred example is DMF.

The condensing agent used therein is not particularly limited as long as it is an agent used in amidation reactions, and the condensing agents described in R. C. Larock, Comprehensive Organic Transformations, Second Edition, 1999, John Wiley & Sons, Inc., and the like may be used. Specific examples include (i) phosphoric acid esters such as diethylphosphoryl cyanide; (ii) carbodiimides such as 1,3-dicyclohexylcarbodiimide, 1,3-diisopropylcarbodiimide, and 1-ethyl-3-(3-dimethylaminopropyl)carbodiimide (WSC), and combinations of these carbodiimides and N-hydroxy compounds such as 4-hydroxybenzotriazole; (iii) imidazoles such as 1,1'-carbonyldiimidazole (CDI); (iv) 4-(4,6-dimethoxy-1,3,5-triazin-2-yl)-4-methylmorpholinium chloride (DMT-MM); and (v) phosphates such as O-(7-azabenzotriazol-1-yl)-N,N,N',N'-tetramethyluronium hexafluorophosphate (HATU), and O-benzotriazol-1-yl-N,N,N',N'-tetramethyluronium hexafluorophosphate (HBTU). A preferred example is a combination of WSC and 4-hydroxybenzotriazole.

The reaction temperature is 0° C. to 100° C., and preferably 0° C. to 50° C. The reaction time is 30 minutes to 96 hours, and preferably 1 to 12 hours.

When a workup is needed, the workup may be carried out according to the following procedure, for example. Water is added to the reaction mixture, and then the product is extracted using an organic solvent such as ethyl acetate. The organic layer thus obtained is washed with water, saturated brine and the like, and is dried over a desiccant such as sodium sulfate. The solvent is distilled off under reduced pressure, and the residue is purified by silica gel chromatography.

Method B

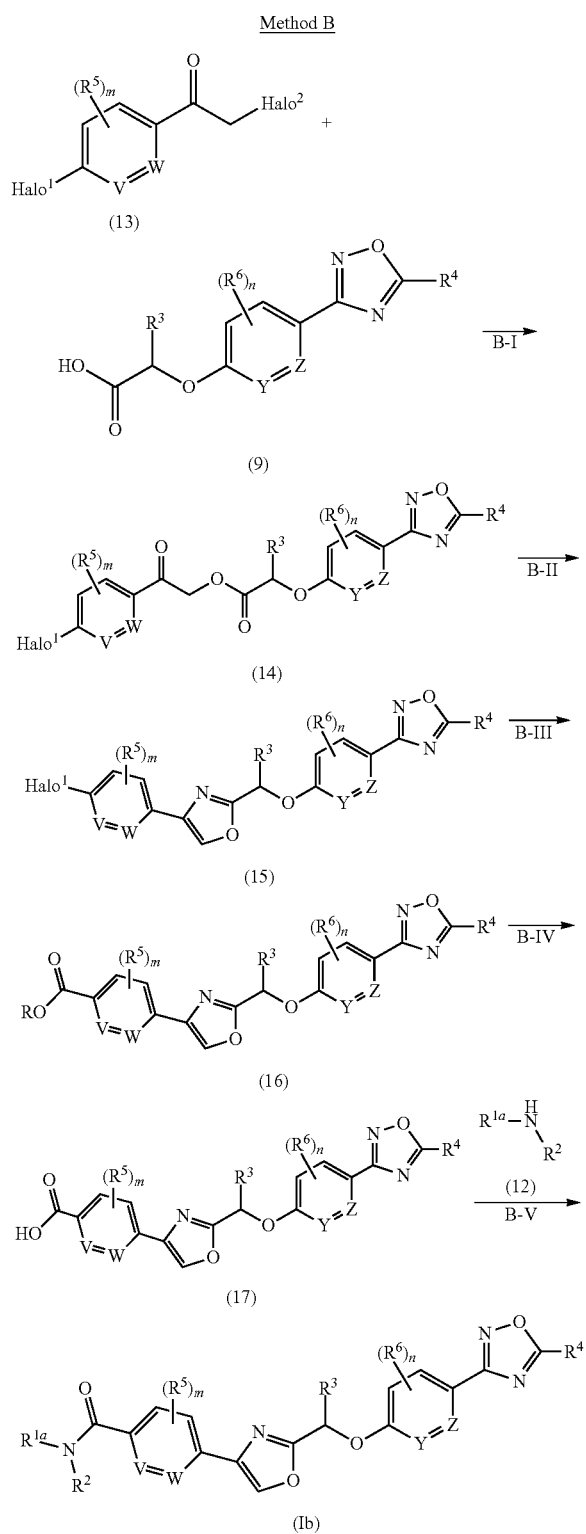

wherein Halo¹ and Halo² each independently represent a halogen atom; and R, $R^{1a}$, V, W, Y, Z, $R^2$, $R^3$, $R^4$, $R^5$, $R^6$, m and n respectively have the same meanings as defined above.

Step B-I is a step for producing a compound (14) by condensing the compound (9) obtained in step A-V described above, with a compound (13).

Examples of a solvent used therein include THF, DMF, 1,4-dioxane, acetonitrile and acetone, and a preferred example is DMF or acetone.

Examples of a reagent used therein include potassium tert-butoxide, cesium carbonate, potassium carbonate, sodium carbonate, sodium hydride, triethylamine and diisopropylethylamine, and a preferred example is triethylamine.

The reaction temperature is 0° C. to 100° C., and preferably 20° C. to 80° C. The reaction time is 30 minutes to 24 hours, and preferably 30 minutes to 6 hours.

When a workup is needed, the workup may be carried out according to the following procedure, for example. The reaction mixture is subjected to extraction with an organic solvent such as ethyl acetate, and the organic layer thus obtained is washed sequentially with water and saturated brine. Subsequently, the organic layer is dried over a desiccant such as sodium sulfate or anhydrous sodium sulfate, and then the resulting residue is purified by silica gel chromatography.

Step B-II is a step for producing a compound (15) by cyclizing the compound (14) obtained in step B-I.

Examples of a solvent used therein include toluene and acetic acid.

Examples of a reagent used therein include ammonium trifluoroacetate and ammonium acetate, and a preferred example is ammonium trifluoroacetate.

The reaction temperature is 80° C. to 200° C., and preferably 100° C. to 160° C. The reaction time is 30 minutes to 24 hours, and preferably 30 minutes to 12 hours.

When a workup is needed, the workup may be carried out according to the following procedure, for example. Water is added to the reaction mixture, and extraction is carried out with an organic solvent such as ethyl acetate. The organic layer thus obtained is washed sequentially with water and saturated brine. Subsequently, the solvent is distilled off under reduced pressure, and the resulting residue is purified by silica gel chromatography.

Step B-III is a step for producing a compound (16) from the compound (15) obtained in step B-II in a carbon monoxide atmosphere, in the presence of a base, using a palladium catalyst.

Examples of a solvent used therein include methanol, and a methanol-DMF mixed solvent, and a preferred example is a methanol-DMF mixed solvent.

Examples of the base used therein include triethylamine, diisopropylethylamine and tributylamine, and a preferred example is triethylamine.

Examples of the palladium catalyst used therein include palladium(II) acetate, palladium(0) dibenzylideneacetone, tetrakistriphenylphosphinepalladium(0), palladium(II) chloride, bistriphenylphosphinepalladium(II) chloride and palladium diphenylphosphinoferrocene(II) chloride, and a preferred example includes palladium(II) acetate or palladium diphenylphosphinoferrocene(II) chloride.

Examples of a reagent used therein include triphenylphosphine, tricyclohexylphosphine, 1,2-bis(diphenylphosphono)ethane, 1,3-bis(diphenylphosphono)propane, 2,2'-bis(diphenylphosphanyl)-1,1'-binaphthyl, 2-(dicyclohexylphosphono)biphenyl, and 2-dicyclohexylphosphino-2'-(N,N-dimethylamino)biphenyl, and a preferred example includes triphenylphosphine or 1,3-bis(diphenylphosphono)propane.

The reaction temperature is 0° C. to 130° C., and preferably 20° C. to 90° C. The reaction time is 30 minutes to 12 hours, and more preferably 30 minutes to 4 hours.

When a workup is needed, the workup may be carried out according to the following procedure, for example. Water is added to the reaction mixture, and extraction is carried out with an organic solvent such as ethyl acetate. The organic layer thus obtained is washed sequentially with water and saturated brine. Subsequently, the solvent is distilled off under reduced pressure, and the resulting residue is purified by silica gel chromatography.

Step B-IV is a step for producing a compound (17) by hydrolyzing the compound (16) obtained in step B-III.

The solvent, reagent, reaction temperature, reaction time and workup used therein are the same as those used in step A-VII described above.

Step B-V is a step for producing the compound (Ib) of the present invention by allowing the compound (17) obtained in step B-IV to react with an amine compound (12) in the presence of a condensing agent.

The solvent, condensing agent, reaction temperature, reaction time and workup used therein are the same as those used in step A-VIII.

mal lipid metabolism, hypertension, fatty liver, metabolic syndrome, edema, heart failure, angina pectoris, myocardial infarction, arteriosclerosis, hyperuricemia, and gout), or diabetic complications (for example, retinosis, kidney failure, neuropathy, cataract, gangrenous leg, infections, and ketosis).

Furthermore, the compound of the present invention or a pharmaceutically acceptable salt thereof has an excellent β cell- or pancreas-protecting action, and can therefore be used as an active ingredient of a pharmaceutical composition that can be used to protect β cells or the pancreas.

The compound of the present invention can also be used in combination with a therapeutic drug for diabetes, a therapeutic drug for diabetic complications, a therapeutic drug for hyperlipidemia, a therapeutic drug for hypertension, and the like other than the compound of the present invention.

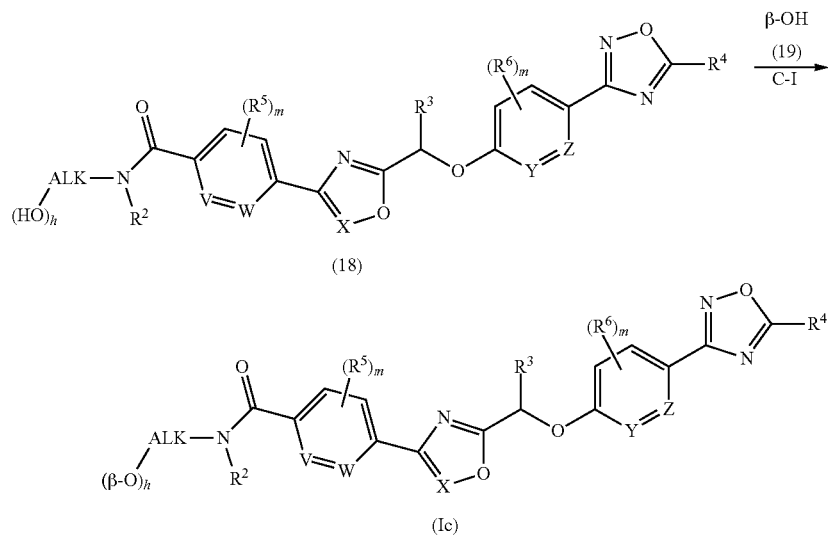

wherein ALK represents a C1-C6 alkylene group; h represents 1 or 2; and V, W, X, Y, Z, $R^2$, $R^3$, $R^4$, $R^5$, $R^6$, m, n and (respectively have the same meanings as defined above.

Step C-I is a step for producing the compound (Ic) of the present invention by allowing a compound (18) between the compound (Ia) and compound (Ib) of the present invention, in which $R^1$ represents a C1-C6 alkyl group substituted with one or two hydroxyl groups, to react with the compound (18) in the presence of a condensing agent.

The solvent, condensing agent, reaction temperature, reaction time and workup used therein are the same as those used in step A-VIII.

The compound of the present invention can be produced by using the methods described above, and can also be easily produced from known compounds according to the Reference Examples and Examples that will be described below.

The compound of the present invention or a pharmaceutically acceptable salt thereof obtained by the methods described above has an excellent hypoglycemic action, and can therefore be used as an active ingredient of a pharmaceutical composition that can be used in the treatment and/or prevention of type 1 diabetes, type 2 diabetes, gestational diabetes, hyperglycemia due to other factors, impaired glucose tolerance (IGT), obesity, diabetes-associated diseases (for example, hyperlipidemia, hypercholesterolemia, abnor- When a pharmaceutical composition containing the compound of the present invention or a pharmaceutically acceptable salt thereof is administered to a mammal (for example, a human, a horse, a cow or a pig; preferably a human), the pharmaceutical composition can be administered systemically or topically, and orally or parenterally.

The pharmaceutical composition of the present invention can be prepared according to the preparation methods for various conventionally used formulations, by selecting appropriate dosage forms in accordance with the administration mode.

Examples of dosage forms of the pharmaceutical composition for oral use include tablets, pills, powders, granules, capsules, liquids, suspensions, emulsions, syrups, and elixirs. Pharmaceutical compositions of such dosage forms can be prepared according to conventional methods, by appropriately selecting as necessary, excipients, binders, disintegrants, lubricating agents, swelling agents, swelling aids, coating agents, plasticizers, stabilizers, antiseptics, antioxidants, colorants, dissolution aids, suspending agents, emulsifiers, sweeteners, preservatives, buffers, diluents, wetting agents and the like, which are conventionally used as additives.

Examples of dosage forms of a pharmaceutical composition for parenteral use include injectable preparations, ointments, gels, creams, poultices, patches, aerosols, inhalants, sprays, eye drops, nose drops, and suppositories. Pharmaceutical compositions of such dosage forms can be prepared according to conventional methods, by appropriately selecting as necessary, stabilizers, antiseptics, dissolution aids, moisturizers, preservatives, antioxidants, fragrances, gelling agents, neutralizing agents, buffers, isotonic agents, surfactants, colorants, buffering agents, thickeners, wetting agents, fillers, absorption promoting agents, suspending agents, binders, and the like, which are conventionally used as additives.

The amount of administration of the compound of the present invention or a pharmaceutically acceptable salt thereof may vary according to symptoms, age, body weight or the like. However, in the case of oral administration, the compound or the salt is administered once or several times a day, in an amount of 1 to 2000 mg, and preferably 1 to 400 mg, in terms of the compound, per dose for an adult; and in the case of parenteral administration, the compound or the salt is administered once or several times a day, in an amount of 0.01 to 500 mg, and preferably 0.1 to 300 mg, in terms of the compound, per dose for an adult.

Hereinafter, the present invention will be described in more detail by way of Reference Examples, Examples, Formulation Example and Test Examples, but the scope of the present invention is not intended to be limited to these.

EXAMPLES

Reference Example 1

Methyl 4-cyano-2-fluorobenzoate

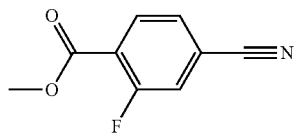

A 4 M hydrochloric acid dioxane solution (70.0 mL, 280 mmol) was added to a methanol (70.0 mL) solution of 4-cyano-2-fluorobenzoic acid (10.0 g, 60.6 mmol), and the mixture was stirred for one hour at 70° C. The reaction mixture was cooled to room temperature, and then the solvent was distilled off under reduced pressure. Thus, a crude product of the title compound was obtained.

Reference Example 2

Methyl 4-amino(hydroxyimino)methyl-2-fluorobenzoate

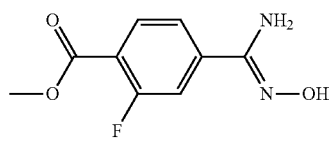

A 50% aqueous solution of hydroxylamine (3.20 mL, 100 mmol) was added to an ethanol (100 mL) solution of the compound obtained in Reference Example 1 (11.0 g, 66.6 mmol), and the mixture was stirred for 3 hours at 70° C. The reaction mixture was cooled to room temperature, subsequently the solvent was distilled off under reduced pressure, and the residue was washed with hexane. Thus, the title compound (9.10 g, yield: 71%) was obtained.

$^1$H-NMR (500 MHz, CD$_3$OD) δ ppm: 7.93 (1H, t, J=8 Hz), 7.56 (1H, d, J=8 Hz), 7.50 (1H, d, J=12 Hz), 3.91 (3H, s).

Reference Example 3

Ethyl 2-(4-cyanophenoxy)butanoate

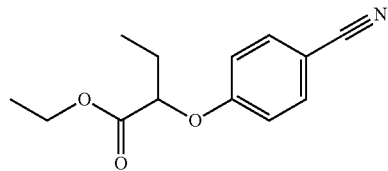 [SMILES: CCOC(=O)C(CC)Oc1ccc(C#N)cc1]

Potassium carbonate (14.5 g, 105 mmol) was added to an acetonitrile (80.0 mL) solution of 4-cyanophenol (5.00 g, 42.0 mmol) and ethyl 2-bromobutyrate (9.83 g, 50.4 mmol) at room temperature, and the mixture was stirred for 3 hours at 80° C. After the mixture was cooled to room temperature, water was added to the reaction mixture, and the mixture was subjected to extraction two times with ethyl acetate. The organic layer thus obtained was washed with saturated brine, and then was dried over anhydrous sodium sulfate. The solvent was distilled off under reduced pressure, and the resulting residue was purified by silica gel column chromatography (hexane:ethyl acetate=9:1→2:1, v/v). Thus, the title compound (9.79 g, yield: 100%) was obtained.

$^1$H-NMR (400 MHz, CDCl$_3$) δ ppm: 7.58 (2H, d, J=9 Hz), 6.92 (2H, d, J=9 Hz), 4.61 (1H, t, J=6 Hz), 4.25-4.20 (2H, m), 2.06-1.99 (2H, m), 1.25 (3H, t, J=7 Hz), 1.08 (3H, t, J=7 Hz).

Reference Example 4

Ethyl 2-{4-[amino(hydroxyimino)methyl]phenoxy}butanoate

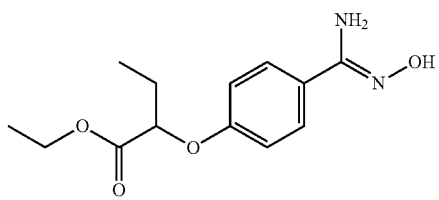 [SMILES: CCOC(=O)C(CC)Oc1ccc(/C(N)=N/O)cc1]

A 50% aqueous solution of hydroxylamine (8.32 mL, 126 mmol) was added to an ethanol (42.0 mL) solution of the compound obtained in Reference Example 3 (9.97 g, 42.0 mmol) at room temperature, and the mixture was stirred for 2.5 hours at 80° C. After the reaction mixture was cooled to room temperature, water was added to the reaction mixture, and the mixture was subjected to extraction two times with ethyl acetate. The organic layer thus obtained was washed with saturated brine, and then was dried over anhydrous sodium sulfate. The solvent was distilled off under reduced pressure, and the resulting residue was purified by silica gel column chromatography (hexane:ethyl acetate=1:1→0:1, v/v). Thus, the title compound (9.82 g, yield: 88%) was obtained.

¹H-NMR (400 MHz, CDCl₃) δ ppm: 7.54 (2H, d, J=9 Hz), 6.89 (2H, d, J=9 Hz), 4.81 (2H, s), 4.58 (1H, t, J=6 Hz), 4.22 (2H, q, J=7 Hz), 2.03-1.97 (2H, m), 1.24 (3H, t, J=7 Hz), 1.08 (3H, t, J=8 Hz).

Reference Example 5

Ethyl 2-[4-(5-isopropyl-1,2,4-oxadiazol-3-yl)phenoxy]butanoate

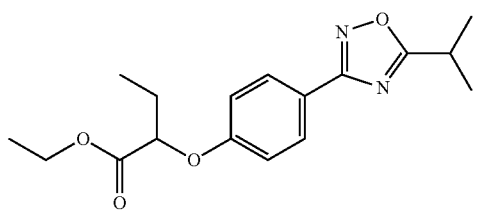 [SMILES: CCOC(=O)C(CC)Oc1ccc(-c2noc(C(C)C)n2)cc1]

Isobutyric acid chloride (1.29 mL, 12.4 mmol) was added to a pyridine (16.0 mL) solution of the compound obtained in Reference Example 4 (3.00 g, 11.3 mmol) at room temperature, and the mixture was stirred for 2 hours at 100° C. After the mixture was cooled to room temperature, the reaction mixture was concentrated under reduced pressure, and water was added thereto. The mixture was subjected to extraction two times with ethyl acetate, and the organic layer thus obtained was washed with a 1 M aqueous hydrochloric acid solution and saturated brine and was dried over anhydrous sodium sulfate. The solvent was distilled off under reduced pressure, and the resulting residue was purified by silica gel column chromatography (hexane:ethyl acetate=3:1, v/v). Thus, the title compound (3.25 g, yield: 91%) was obtained.

¹H-NMR (400 MHz, CDCl₃) δ ppm: 8.00 (2H, d, J=9 Hz), 6.95 (2H, d, J=9 Hz), 4.62 (1H, t, J=6 Hz), 4.22 (2H, q, J=7 Hz), 3.31-3.22 (1H, m), 2.05-1.99 (2H, m), 1.45 (6H, d, J=7 Hz), 1.24 (3H, t, J=7 Hz), 1.10 (3H, t, J=7 Hz).

Reference Example 6

2-[4-(5-Isopropyl-1,2,4-oxadiazol-3-yl)phenoxy]butanoic acid

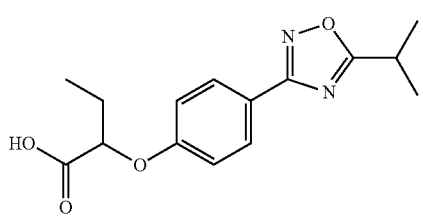 [SMILES: CCC(Oc1ccc(-c2noc(C(C)C)n2)cc1)C(=O)O]

The compound obtained in Reference Example 5 (1.50 g, 4.71 mmol) was dissolved in a tetrahydrofuran (6.00 mL)-methanol (6.00 mL) solution, and a 1 M aqueous solution of sodium hydroxide (5.65 mL, 5.65 mmol) was added thereto. The mixture was stirred for 30 minutes at room temperature. The reaction mixture was concentrated under reduced pressure, and water and a 1 M aqueous hydrochloric acid solution were added thereto. The mixture was subjected to extraction two times with ethyl acetate, and the organic layer thus obtained was washed with saturated brine and then was dried over anhydrous sodium sulfate. The solvent was distilled off under reduced pressure, and the resulting residue was washed with hexane. Thus, the title compound (1.30 g, yield: 95%) was obtained.

¹H-NMR (400 MHz, CDCl₃) δ ppm: 8.00 (2H, d, J=9 Hz), 6.98 (2H, d, J=9 Hz), 4.69 (1H, dd, J=6 Hz, 5 Hz), 3.31-3.25 (1H, m), 2.10-2.03 (2H, m), 1.45 (6H, d, J=7 Hz), 1.13 (3H, t, J=7 Hz).

Reference Example 7

Methyl 2-fluoro-4-(5-{1-[4-(5-isopropyl-1,2,4-oxadiazol-3-yl)phenoxy]propyl}-1,2,4-oxadiazol-3-yl)benzoate

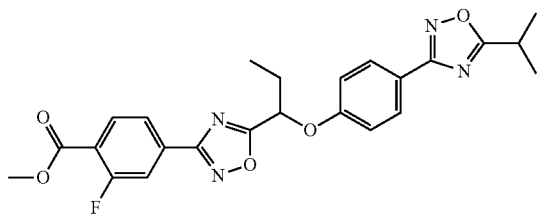 [SMILES: CCC(Oc1ccc(-c2noc(C(C)C)n2)cc1)c1nc(-c2ccc(C(=O)OC)c(F)c2)no1]

To a dimethylformamide (24.0 mL) solution of the compound obtained in Reference Example 6 (1.37 g, 4.71 mmol), 1-hydroxybenzotriazole monohydrate (722 mg, 4.71 mmol) and N-(3-dimethylaminopropyl)-N'-ethylcarbodiimide (1.81 g, 9.43 mmol) were added at room temperature. The mixture was stirred for 15 minutes at the same temperature. The compound obtained in Reference Example 2 (1.00 g, 4.71 mmol) was added thereto, and the resulting mixture was stirred for 15 minutes, and was further stirred for 3 hours at 100° C. The reaction mixture was cooled to room temperature, subsequently water was added to the reaction mixture, and the mixture was subjected to extraction two times with ethyl acetate. The organic layer thus obtained was washed with a saturated aqueous solution of sodium hydrogen carbonate and saturated brine, and then was dried over anhydrous sodium sulfate. The solvent was distilled off under reduced pressure, and the resulting residue was purified by silica gel column chromatography (hexane:ethyl acetate=1:0→3:1, v/v). Thus, the title compound (1.65 g, yield: 75%) was obtained.

¹H-NMR (400 MHz, CDCl₃) δ ppm: 8.05 (1H, dd, J=10 Hz, 8 Hz), 8.01 (2H, d, J=9 Hz), 7.92 (1H, dd, J=8 Hz, 2 Hz), 7.87 (1H, dd, J=10 Hz, 2 Hz), 7.06 (2H, d, J=9 Hz), 5.51 (1H, dd, J=7 Hz, 6 Hz), 3.96 (3H, s), 3.29-3.22 (1H, m), 2.34-2.20 (2H, m), 1.43 (6H, d, J=7 Hz), 1.14 (3H, t, J=7 Hz).

Reference Example 8

2-Fluoro-4-(5-{1-[4-(5-isopropyl-1,2,4-oxadiazol-3-yl)phenoxy]propyl}-1,2,4-oxadiazol-3-yl)benzoic acid

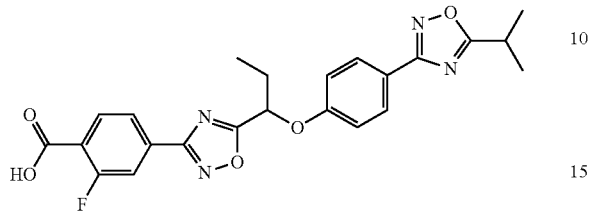

A 1 M aqueous solution of sodium hydroxide (4.22 mL, 4.22 mmol) was added to a tetrahydrofuran (4.00 mL)-methanol (4.00 mL) solution of the compound obtained in Reference Example 7 (1.64 g, 3.52 mmol), and the mixture was stirred for one hour at room temperature. The reaction mixture was concentrated under reduced pressure, water was added thereto, and the aqueous layer was washed with diethyl ether. Subsequently, a 1 M aqueous hydrochloric acid solution was added thereto, and the mixture was subjected to extraction two times with ethyl acetate. The organic layer thus obtained was washed with saturated brine, and then was dried over anhydrous sodium sulfate. The solvent was distilled off under reduced pressure, and the resulting residue was washed with hexane-diethyl ether (10:1, v/v). Thus, the title compound (1.44 g, yield: 91%) was obtained.

$^1$H-NMR (400 MHz, CDCl$_3$) δ ppm: 8.14 (1H, dd, J=10 Hz, 8 Hz), 8.01 (2H, d, J=9 Hz), 7.97 (1H, dd, J=8 Hz, 1 Hz), 7.91 (1H, dd, J=10 Hz, 1 Hz), 7.07 (2H, d, J=9 Hz), 5.52 (1H, dd, J=7 Hz, 6 Hz), 3.29-3.23 (1H, m), 2.35-2.20 (2H, m), 1.44 (6H, d, J=7 Hz), 1.15 (3H, t, J=8 Hz).

Reference Example 9

Methyl 4-bromo-2-methylbenzoate

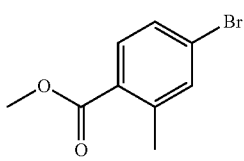

Concentrated sulfuric acid (500 μL) was added to a methanol (20.0 mL) solution of 4-bromo-2-methylbenzoic acid (2.00 g, 9.30 mmol), and the mixture was stirred for 5 hours at 80° C. The reaction mixture was cooled to room temperature, subsequently a saturated aqueous solution of sodium hydrogen carbonate was added to the reaction mixture, and the mixture was subjected to extraction two times with ethyl acetate. The organic layer thus obtained was washed once with saturated brine, and was dried over anhydrous sodium sulfate. The solvent was distilled off under reduced pressure, and thus, the title compound (2.02 g, yield: 95%) was obtained.

$^1$H-NMR (400 MHz, CDCl$_3$) δ ppm: 7.78 (1H, d, J=9 Hz), 7.41 (1H, d, J=2 Hz), 7.38 (1H, dd, J=9 Hz, 2 Hz), 3.89 (3H, s), 2.58 (3H, s).

Reference Example 10

Methyl 4-cyano-2-methylbenzoate

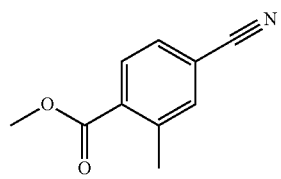

To a dimethylacetamide (4.62 mL) solution of the compound obtained in Reference Example 9 (498 mg, 2.32 mmol), zinc cyanide (163 mg, 1.39 mmol), tris(dibenzylideneacetone)dipalladium(0) (42 mg, 46.3 μmol) and 1,1'-bis(diphenylphosphino)ferrocene (51 mg, 92.6 μmol) were added, and the mixture was stirred for 2 hours at 90° C. The reaction mixture was cooled to room temperature, subsequently a saturated aqueous solution of ammonium chloride was added to the reaction mixture, and the mixture was subjected to extraction two times with ethyl acetate. The organic layer thus obtained was washed with water and saturated brine, and was dried over anhydrous sodium sulfate. The solvent was distilled off under reduced pressure, and the resulting residue was purified by silica gel column chromatography (hexane:ethyl acetate=4:1 (1:1, v/v). Thus, the title compound (294 mg, yield: 73%) was obtained.

1H-NMR (400 MHz, CDCl$_3$) (ppm: 7.97 (1H, d, J=8 Hz), 7.55-7.53 (2H, m), 3.93 (3H, s), 2.62 (3H, s).

Reference Example 11

Methyl 4-[amino(hydroxyimino)methyl]-2-methylbenzoate

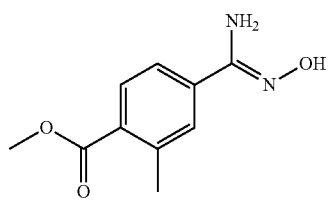

The synthesis was carried out in the same manner as in Reference Example 2, except that the compound obtained in Reference Example 10 (294 mg, 1.68 mmol) was used in place of methyl 4-cyano-2-fluorobenzoate. Thus, the title compound (255 mg, yield: 73%) was obtained.

$^1$H-NMR (400 MHz, CD$_3$OD) δ ppm: 7.89 (1H, d, J=8 Hz), 7.58 (1H, s), 7.55 (1H, d, J=8 Hz), 3.88 (3H, s), 2.59 (3H, s).

Reference Example 12

Methyl 4-(5-{1-[4-(5-isopropyl-1,2,4-oxadiazol-3-yl)phenoxy]propyl}-1,2,4-oxadiazol-3-yl)-2-methylbenzoate

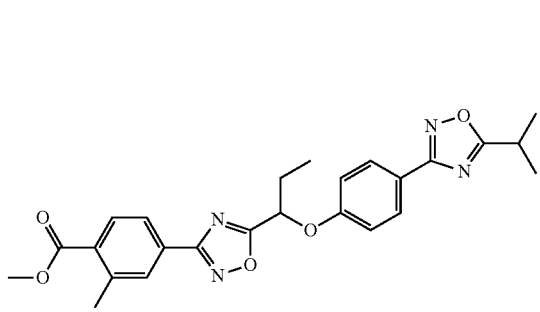 [SMILES: CCC(Oc1ccc(-c2noc(C(C)C)n2)cc1)c1nc(-c2ccc(C(=O)OC)c(C)c2)no1]

The synthesis was carried out in the same manner as in Reference Example 7, except that the compound obtained in Reference Example 11 (120 mg, 0.576 mmol) was used in place of methyl 4-amino(hydroxyimino)methyl-2-fluorobenzoate. Thus, the title compound (200 mg, yield: 75%) was obtained.

$^1$H-NMR (400 MHz, CDCl$_3$) δ ppm: 8.02-7.93 (5H, m), 7.07 (2H, d, J=9 Hz), 5.51 (1H, t, J=6 Hz), 3.92 (3H, s), 3.25 (1H, sept, J=7 Hz), 2.66 (3H, s), 2.34-2.20 (2H, m), 1.43 (6H, d, J=7 Hz), 1.14 (3H, t, J=7 Hz).

Reference Example 13

4-(5-{1-[4-(5-isopropyl-1,2,4-oxadiazol-3-yl)phenoxy]propyl}-1,2,4-oxadiazol-3-yl)-2-methylbenzoic acid

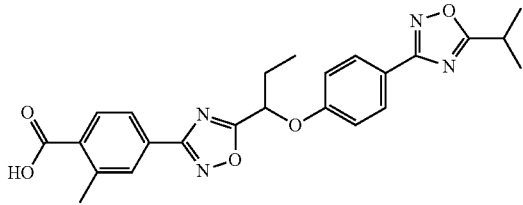 [SMILES: CCC(Oc1ccc(-c2noc(C(C)C)n2)cc1)c1nc(-c2ccc(C(=O)O)c(C)c2)no1]

The synthesis was carried out in the same manner as in Reference Example 8, except that the compound obtained in Reference Example 12 (154 mg, 0.333 mmol) was used in place of methyl 2-fluoro-4-(5-{1-[4-(5-isopropyl-1,2,4-oxadiazol-3-yl)phenoxy]propyl}-1,2,4-oxadiazol-3-yl)benzoate. Thus, the title compound (113 mg, yield: 76%) was obtained.

$^1$H-NMR (400 MHz, CDCl$_3$) δ ppm: 8.15 (1H, d, J=8 Hz), 8.02-7.98 (4H, m), 7.08 (2H, d, J=9 Hz), 5.52 (1H, t, J=6 Hz), 3.26 (1H, sept, J=7 Hz), 2.72 (3H, s), 2.35-2.21 (2H, m), 1.44 (6H, d, J=7 Hz), 1.15 (3H, t, J=7 Hz).

Reference Example 14

(2R)-2-{[2-fluoro-4-(5-{1-[4-(5-isopropyl-1,2,4-oxadiazol-3-yl)phenoxy]propyl}-1,2,4-oxadiazol-3-yl)benzoyl]amino}propyl N-(tert-butoxycarbonyl)glycinate

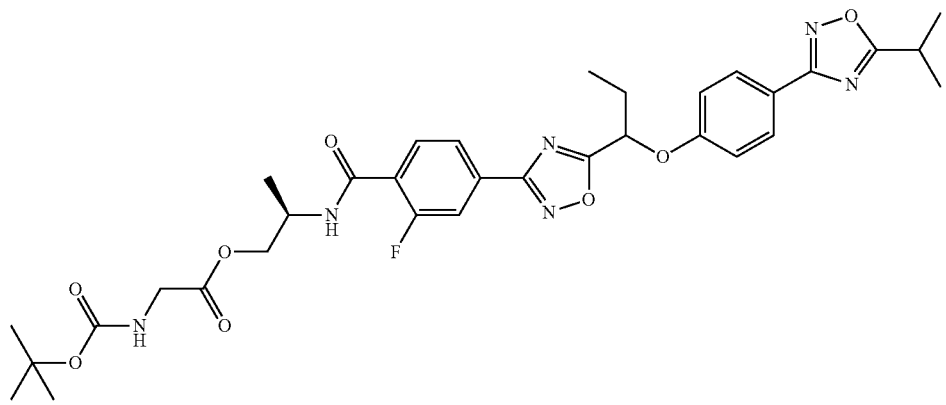 [SMILES: CCC(Oc1ccc(-c2noc(C(C)C)n2)cc1)c1nc(-c2ccc(C(=O)N[C@H](C)COC(=O)CNC(=O)OC(C)(C)C)c(F)c2)no1]

To a dimethylformamide (1.00 mL) solution of the compound obtained in Example 7 that will be described below (69.2 mg, 0.136 mmol), N-(tert-butoxycarbonyl)glycine (47.6 mg, 0.272 mmol), 1-(3-dimethylaminopropyl)-3-ethylcarbodiimide (78.1 mg, 0.405 mmol) and 4-dimethylaminopyridine (1.70 mg, 0.0183 mmol) were added, and the mixture was stirred for one hour at room temperature. Water was added to the reaction mixture, and the mixture was subjected to extraction two times with ethyl acetate, and the organic layer thus obtained was washed sequentially with water and saturated brine and was dried over anhydrous sodium sulfate. The solvent was distilled off under reduced pressure, and the resulting residue was purified by silica gel column chromatography (methylene chloride:methanol=99:1→90:10, v/v). Thus, the title compound (91 mg, yield: 100%) was obtained.

Reference Example 15

(2S)-2-{[2-fluoro-4-(5-{1-[4-(5-isopropyl-1,2,4-oxadiazol-3-yl)phenoxy]propyl}-1,2,4-oxadiazol-3-yl)benzoyl]amino}propyl N-(tert-butoxycarbonyl)glycinate

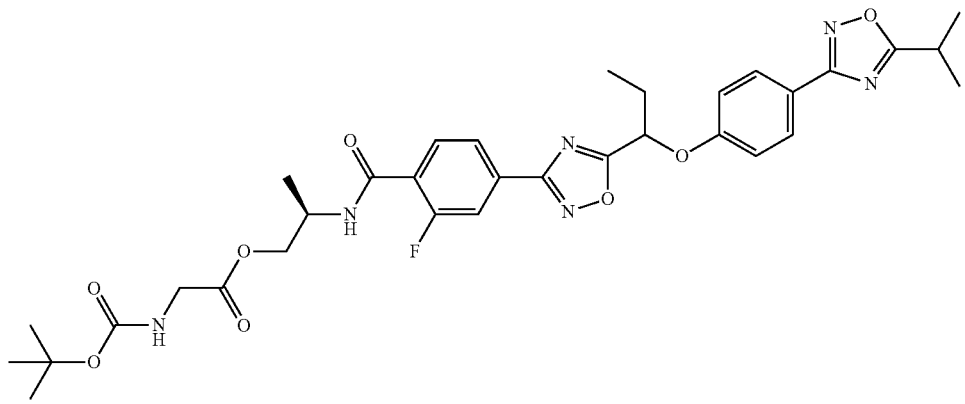 [SMILES: CCC(Oc1ccc(-c2noc(C(C)C)n2)cc1)c1nc(-c2ccc(C(=O)N[C@H](C)COC(=O)CNC(=O)OC(C)(C)C)c(F)c2)no1]

The synthesis was carried out in the same manner as in Reference Example 14, except that the compound obtained in Example 6 that will be described below (100 mg, 0.196 mmol) was used in place of 2-fluoro-N-[(1R)-2-hydroxy-1-methylethyl]-4-(5-{1-[4-(5-isopropyl-1,2,4-oxadiazol-3-yl)phenoxy]propyl}-1,2,4-oxadiazol-3-yl)benzamide. Thus, a crude product of the title compound (125 mg) was obtained.

Reference Example 16

(2R)-2-{[2-fluoro-4-(5-{1-[4-(5-isopropyl-1,2,4-oxadiazol-3-yl)phenoxy]propyl}-1,2,4-oxadiazol-3-yl)benzoyl]amino}butyl N-(tert-butoxycarbonyl)glycinate

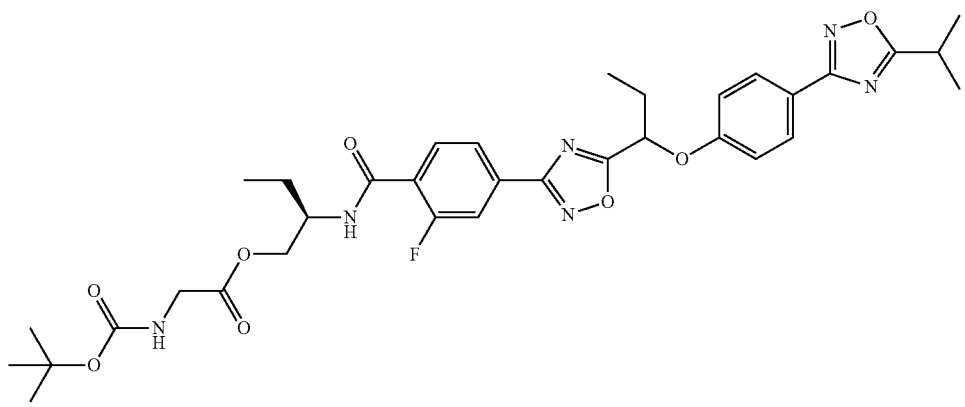 [SMILES: CCC(Oc1ccc(-c2noc(C(C)C)n2)cc1)c1nc(-c2ccc(C(=O)N[C@H](CC)COC(=O)CNC(=O)OC(C)(C)C)c(F)c2)no1]

The synthesis was carried out in the same manner as in Reference Example 14, except that the compound obtained in Example 10 that will be described below (274 mg, 0.523 mmol) was used in place of 2-fluoro-N-[(1R)-2-hydroxy-1-methylethyl]-4-(5-{1-[4-(5-isopropyl-1,2,4-oxadiazol-3-yl)phenoxy]propyl}-1,2,4-oxadiazol-3-yl)benzamide. Thus, a crude product of the title compound (358 mg) was obtained.

Reference Example 17

(2S)-2-{[2-fluoro-4-(5-{1-[4-(5-isopropyl-1,2,4-oxadiazol-3-yl)phenoxy]propyl}-1,2,4-oxadiazol-3-yl)benzoyl]amino}butyl N-(tert-butoxycarbonyl)glycinate

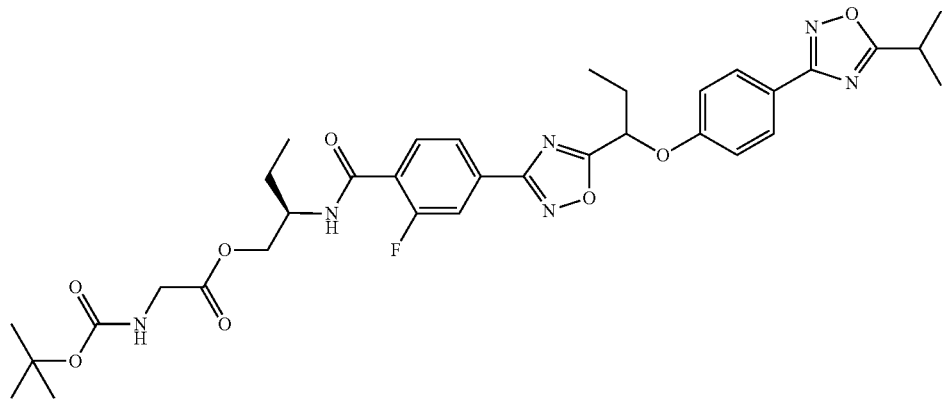 [SMILES: CCC(Oc1ccc(-c2noc(C(C)C)n2)cc1)c1nc(-c2ccc(C(=O)N[C@H](CC)COC(=O)CNC(=O)OC(C)(C)C)c(F)c2)no1]

The synthesis was carried out in the same manner as in Reference Example 14, except that the compound obtained in Example 9 that will be described below (220 mg, 0.420 mmol) was used in place of 2-fluoro-N-[(1R)-2-hydroxy-1-methylethyl]-4-(5-{1-[4-(5-isopropyl-1,2,4-oxadiazol-3-yl)phenoxy]propyl}-1,2,4-oxadiazol-3-yl)benzamide. Thus, a crude product of the title compound (274 mg) was obtained.

Reference Example 18

2-{[2-fluoro-4-(5-{1-[4-(5-isopropyl-1,2,4-oxadiazol-3-yl)phenoxy]propyl}-1,2,4-oxadiazol-3-yl)benzoyl]amino}-2-methylpropyl N-(tert-butoxycarbonyl)glycinate

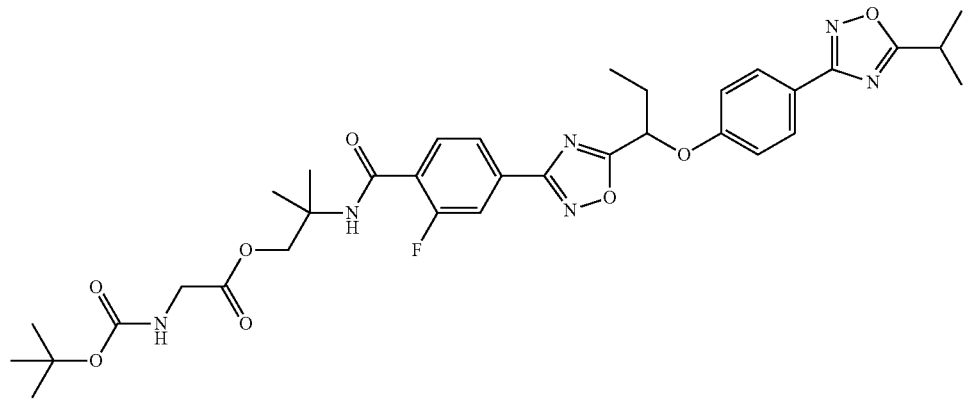 [SMILES: CCC(Oc1ccc(-c2noc(C(C)C)n2)cc1)c1nc(-c2ccc(C(=O)NC(C)(C)COC(=O)CNC(=O)OC(C)(C)C)c(F)c2)no1]

The synthesis was carried out in the same manner as in Reference Example 14, except that the compound obtained in Example 8 that will be described below (133 mg, 0.254 mmol) was used in place of 2-fluoro-N-[(1R)-2-hydroxy-1-methylethyl]-4-(5-{1-[4-(5-isopropyl-1,2,4-oxadiazol-3-yl)phenoxy]propyl}-1,2,4-oxadiazol-3-yl)benzamide. Thus, the title compound (173 mg, yield: 100%) was obtained.

Reference Example 19

4-Methoxybenzyl glycolate

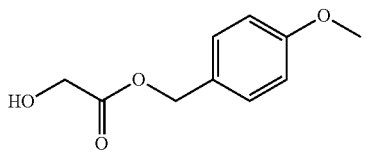

Sodium hydrogen carbonate (2.20 g, 26.3 mg) was added to a solution of glycolic acid (2.00 g, 26.3 mmol) in water (2.00 mL), and the mixture was stirred for one hour at room temperature. The solvent was distilled off from the reaction mixture under reduced pressure, and to a dimethylformamide (10.0 mL) solution of the resulting residue, p-methoxybenzyl chloride (4.10 g, 26.3 mmol) was added. The mixture was stirred for 2 hours at room temperature. Water was added to the reaction mixture, and the mixture was subjected to extraction with ethyl acetate. The organic layer thus obtained was washed sequentially with water and saturated brine, and was dried over anhydrous sodium sulfate. The solvent was distilled off under reduced pressure. Thus, a crude product of the title compound (4.24 g) was obtained.

Reference Example 20

4-Methoxybenzyl {[(allyloxy)carbonyl]oxy}acetate

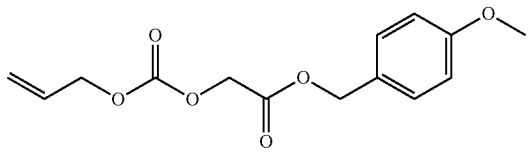 [SMILES: C=CCOC(=O)OCC(=O)OCc1ccc(OC)cc1]

To a methylene chloride (70.0 mL) solution of the compound obtained in Reference Example 19 (4.25 g, 25.7 mmol), 4-dimethylaminopyridine (3.80 g, 2.57 mmol) and a methylene chloride (10.0 mL) solution of allyl chloroformate (3.30 mL, 30.8 mmol) were added, and the mixture was stirred for 30 minutes at room temperature. Water was added to the reaction mixture, and the mixture was subjected to extraction with methylene chloride. The organic layer thus obtained was washed with water, and was dried over anhydrous sodium sulfate. The solvent was distilled off under reduced pressure. The resulting residue was subjected to silica gel column chromatography (hexane:ethyl acetate=19:1→1:1, v/v). Thus, a crude product of the title compound (4.69 g) was obtained.

Reference Example 21

[(Allyloxy)carbonyl]oxyacetic acid

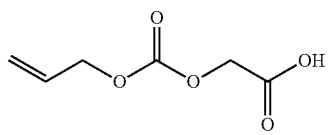

Trifluoromethanesulfonic acid (20.0 mL) and anisole (3.40 mL, 49.6 mmol) were added to the compound obtained in Reference Example 20 (4.69 g, 16.5 mmol), and the mixture was stirred for 2 hours at room temperature. Toluene (100 mL) was added to the reaction mixture, and the solvent was distilled off under reduced pressure. Thus, a crude product of the title compound (2.90 g) was obtained.

Reference Example 22

(2R)-2-{[2-fluoro-4-(5-{1-[4-(5-isopropyl-1,2,4-oxadiazol-3-yl)phenoxy]propyl}-1,2,4-oxadiazol-3-yl)benzoyl]amino}propyl {[(allyloxy)carbonyl]oxy}acetate

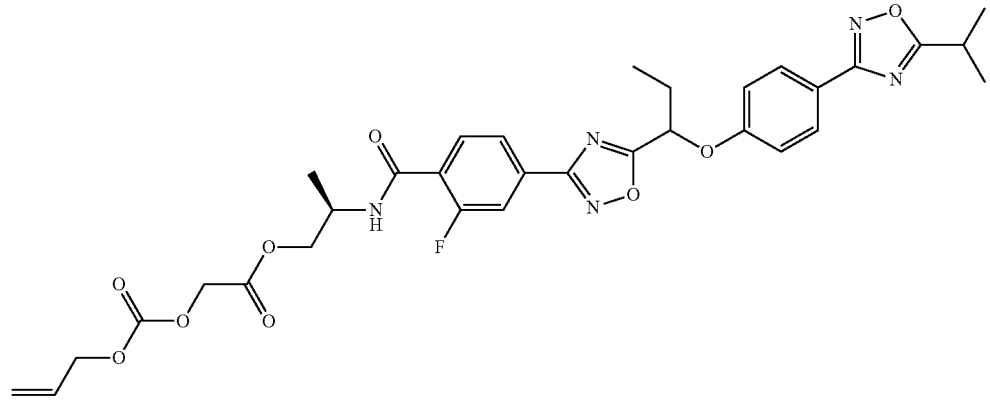 [SMILES: C=CCOC(=O)OCC(=O)OC[C@@H](C)NC(=O)c1ccc(-c2noc(C(CC)Oc3ccc(-c4noc(C(C)C)n4)cc3)n2)cc1F]

To a dimethylformamide (7.00 mL) solution of the compound obtained in Example 7 that will be described below (344 mg, 0.676 mmol), the compound obtained in Reference Example 21 (163 mg, 1.01 mmol), 4-dimethylaminopyridine (8.26 mg, 0.0676 mmol) and 1-(3-dimethylaminopropyl)-3-ethylcarbodiimide (389 mg, 2.03 mmol) were added, and the mixture was stirred for 2 hours at room temperature. Water was added to the reaction mixture, and the mixture was subjected to extraction with ethyl acetate. The organic layer thus obtained was washed sequentially with water and saturated brine, and was dried over anhydrous sodium sulfate. The solvent was distilled off under reduced pressure, and the resulting residue was purified by silica gel column chromatography (hexane:ethyl acetate=9:1→1:1, v/v). Thus, the title compound (300 mg, yield: 75%) was obtained.

Reference Example 23

2-Diazo-1-(4-bromo-3-fluorophenyl)ethanone

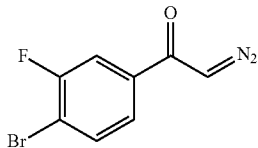

To a methylene chloride (50.0 mL) solution of 4-bromo-3-fluorobenzoic acid (5.00 g, 22.8 mmol), dimethylformamide (5 droplets) and oxalyl chloride (2.39 mL, 27.4 mmol) were added at room temperature, and the mixture was stirred for 1.5 hours at the same temperature. Subsequently, the solvent was distilled off under reduced pressure. The resulting residue was dissolved in tetrahydrofuran (15.0 mL)-acetonitrile (15.0 mL), and triethylamine (6.36 mL, 45.7 mmol) and a 2 M-trimethylsilyldiazomethane tetrahydrofuran solution (22.8 mL, 45.7 mmol) were added to the solution at room temperature. The mixture was stirred for 30 minutes. Water was added to the reaction mixture, and the mixture was subjected to extraction two times with ethyl acetate. The organic layer was washed with saturated brine, and then was dried over anhydrous sodium sulfate. The solvent was distilled off under reduced pressure. The resulting residue was washed with hexane-ethyl acetate (10:1, v/v). Thus, a crude product of the title compound (3.36 g) was obtained.

Reference Example 24

2-Bromo-1-(4-bromo-3-fluorophenyl)ethanone

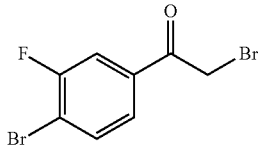 [SMILES: O=C(CBr)c1ccc(Br)c(F)c1]

A 30% hydrogen bromide-acetic acid solution (3.50 mL, excess amount) was added to a methylene chloride (14.0 mL) solution of the compound obtained in Reference Example 23 (3.35 g, about 13.8 mmol) under ice water cooling, and the mixture was stirred for 10 minutes at the same temperature. Water was added to the reaction mixture, and the mixture was subjected to extraction two times with ethyl acetate. The organic layer thus obtained was washed with a saturated aqueous solution of sodium hydrogen carbonate and saturated brine, and then was dried over anhydrous sodium sulfate. The solvent was distilled off under reduced pressure. The resulting residue was washed with hexane-ethyl acetate (10:1, v/v). Thus, a crude product of the title compound (3.92 g) was obtained.

Reference Example 25

2-(4-Bromo-3-fluorophenyl)-2-oxoethyl 2-[4-(5-isopropyl-1,2,4-oxadiazol-3-yl)phenoxy]butanoate

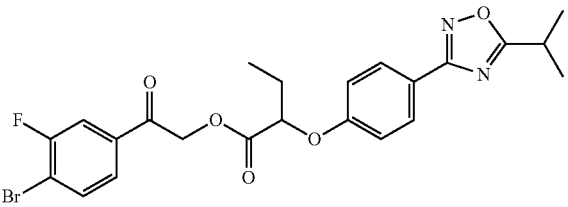 [SMILES: CCC(Oc1ccc(-c2noc(C(C)C)n2)cc1)C(=O)OCC(=O)c1ccc(Br)c(F)c1]

Triethylamine (353 µL, 2.53 mmol) was added to an acetone (9.00 mL) solution of the compound obtained in Reference Example 24 (500 mg, 1.69 mmol) and the compound obtained in Reference Example 6 (540 mg, 1.86 mmol) at room temperature, and the mixture was stirred for 2 hours at the same temperature. Water was added to the reaction mixture, and the mixture was subjected to extraction two times with ethyl acetate. The organic layer thus obtained was washed with a saturated sodium hydrogen carbonate solution and saturated brine, and then was dried over anhydrous sodium sulfate. The solvent was distilled off under reduced pressure. Thus, a crude product of the title compound (854 mg) was obtained.

Reference Example 26

3-(4-{1-[4-(4-Bromo-3-fluorophenyl)-1,3-oxazol-2-yl]propoxy}phenyl)-5-isopropyl-1,2,4-oxadiazole

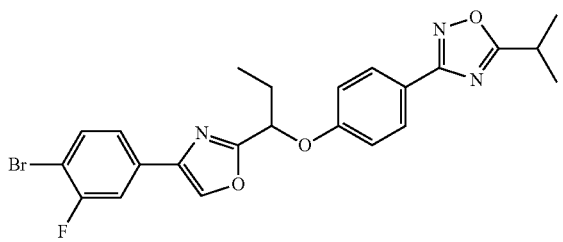 [SMILES: CCC(Oc1ccc(-c2noc(C(C)C)n2)cc1)c1nc(-c2ccc(Br)c(F)c2)co1]

Ammonium trifluoroacetate (1.70 g, excess amount) was added to the compound obtained in Reference Example 25 (854 mg, 1.69 mmol), and the mixture was stirred for 6 hours at 150° C. The reaction mixture was cooled to room temperature, subsequently water was added to the reaction mixture, and the mixture was subjected to extraction two times with ethyl acetate. The organic layer thus obtained was washed with water and saturated brine, and then was dried over anhydrous sodium sulfate. The solvent was distilled off under reduced pressure, and the resulting residue was purified by

Reference Example 27

2-Fluoro-4-(2-{1-[4-(5-isopropyl-1,2,4-oxadiazol-3-yl)phenoxy]propl}-1,3-oxazol-4-yl)benzoic acid

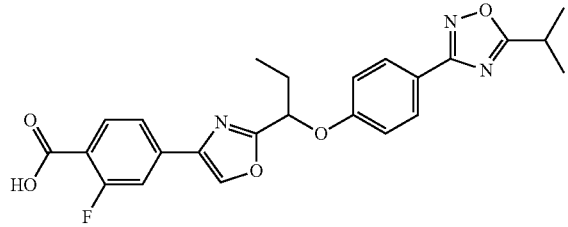 [SMILES: CCC(Oc1ccc(-c2noc(C(C)C)n2)cc1)c1nc(-c2ccc(C(=O)O)c(F)c2)co1]

To a dimethylformamide (2.50 mL)-methanol (2.50 mL) solution of the compound obtained in Reference Example 26 (496 mg, 1.02 mmol), triethylamine (426 μL, 3.06 mmol) and a [1,1'-bis(diphenylphosphino)ferrocene]palladium(II) dichloride-methylene chloride complex (167 mg, 0.204 mmol) were added at room temperature, and the mixture was stirred for 5 hours at 80° C. under a carbon monoxide gas stream. The reaction mixture was cooled to room temperature, subsequently water was added to the reaction mixture, and the mixture was subjected to extraction two times with ethyl acetate. The organic layer thus obtained was washed with saturated brine, and then was dried over anhydrous sodium sulfate. The solvent was distilled off under reduced pressure, and the resulting residue (300 mg) was dissolved in tetrahydrofuran (1.60 mL)-methanol (800 μL). A 1 M aqueous solution of sodium hydroxide (773 μL, 0.773 mmol) was added to the solution, and the mixture was stirred for 2.5 hours at room temperature. The reaction mixture was concentrated under reduced pressure, and water was added thereto. The aqueous layer was washed with diethyl ether, and then a 1 M-aqueous hydrochloric acid solution was added thereto. The mixture was subjected to extraction two times with ethyl acetate, and the organic layer thus obtained was washed with saturated brine and then was dried over anhydrous sodium sulfate. The solvent was distilled off under reduced pressure, and the resulting residue was washed with a hexane-diethyl ether (10:1, v/v) mixture. Thus, a crude product of the title compound (262 mg) was obtained.

Reference Example 28

(2S)-2-{[2-fluoro-4-(2-{1-[4-(5-isopropyl-1,2,4-oxadiazol-3-yl)phenoxy]propyl}-1,3-oxazol-4-yl)benzoyl]amino}propyl N-(tert-butoxycarbonyl)glycinate

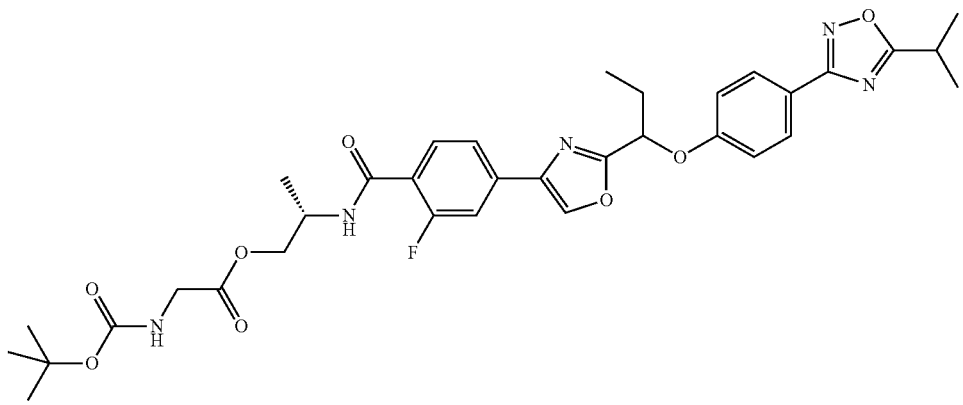 [SMILES: CCC(Oc1ccc(-c2noc(C(C)C)n2)cc1)c1nc(-c2ccc(C(=O)N[C@@H](C)COC(=O)CNC(=O)OC(C)(C)C)c(F)c2)co1]

The synthesis was carried out in the same manner as in Reference Example 14, except that the compound obtained in Example 18 that will be described below (20.0 mg, 39.3 μmol) was used in place of 2-fluoro-N-[(1R)-2-hydroxy-1-methylethyl]-4-(5-{1-[4-(5-isopropyl-1,2,4-oxadiazol-3-yl)phenoxy]propyl}-1,2,4-oxadiazol-3-yl)benzamide. Thus, the title compound (26 mg) was obtained.

Reference Example 29

Ethyl 2-[4-(5-ethyl-1,2,4-oxadiazol-3-yl)phenoxy]butanoate

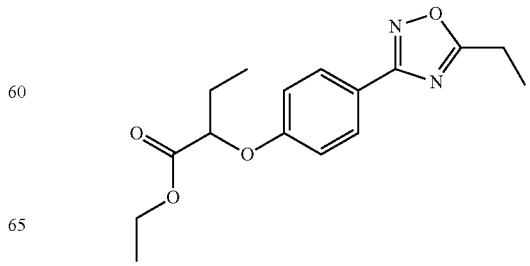

The synthesis was carried out in the same manner as in Reference Example 5, except that the compound obtained in Reference Example 4 (4.10 g, 15.4 mmol) was used, and propionic acid chloride (1.47 mL, 17.0 mmol) was used in place of isobutyric acid chloride. Thus, the title compound (1.95 g, yield: 42%) was obtained.

$^1$H-NMR (400 MHz, CDCl$_3$) δ ppm: 8.00 (2H, d, J=8 Hz), 6.96 (2H, d, J=8 Hz), 4.63 (1H, t, J=6 Hz), 4.23 (2H, q, J=7 Hz), 2.96 (2H, q, J=7 Hz), 2.02 (2H, q, J=7 Hz), 1.44 (3H, t, J=7 Hz), 1.25 (3H, t, J=7 Hz), 1.10 (3H, t, J=7 Hz).

Reference Example 30

2-[4-(5-Ethyl-1,2,4-oxadiazol-3-yl)phenoxy]butanoic acid

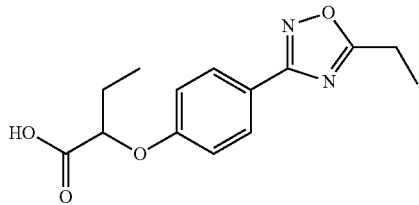 [SMILES: CCc1nc(-c2ccc(OC(CC)C(=O)O)cc2)no1]

The synthesis was carried out in the same manner as in Reference Example 6, except that the compound obtained in Reference Example 29 (1.95 g, 6.41 mmol) was used in place of ethyl 2-[4-(5-isopropyl-1,2,4-oxadiazol-3-yl)phenoxy]butanoate. Thus, the title compound (1.77 g, yield: 100%) was obtained.

$^1$H-NMR (400 MHz, CDCl$_3$) δ ppm: 8.00 (2H, d, J=9 Hz), 6.99 (2H, d, J=9 Hz), 4.69 (1H, t, J=6 Hz), 2.97 (2H, q, J=8 Hz), 2.11-2.05 (2H, m), 1.44 (3H, t, J=8 Hz), 1.13 (3H, t, J=8 Hz).

Reference Example 31

Methyl 4-(5-{1-[4-(5-ethyl-1,2,4-oxadiazol-3-yl)phenoxy]propyl}-1,2,4-oxadiazol-3-yl)-2-fluorobenzoate

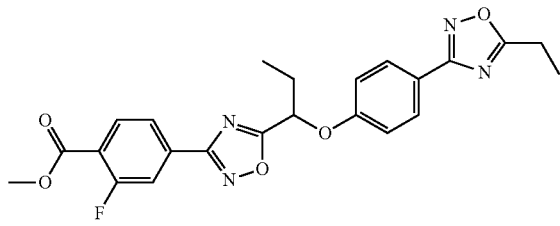 [SMILES: CCc1nc(-c2ccc(OC(CC)c3nc(-c4ccc(C(=O)OC)c(F)c4)no3)cc2)no1]

The synthesis was carried out in the same manner as in Reference Example 7, except that the compound obtained in Reference Example 30 (1.97 g, 7.13 mmol) was used in place of 2-[4-(5-isopropyl-1,2,4-oxadiazol-3-yl)phenoxy]butanoic acid. Thus, the title compound (1.94 g, yield: 60%) was obtained.

$^1$H-NMR (400 MHz, CDCl$_3$) δ ppm: 8.07-7.99 (3H, m), 7.93 (1H, dd, J=8 Hz, 2 Hz), 7.88 (1H, dd, J=11 Hz, 2 Hz), 7.07 (2H, d, J=9 Hz), 5.51 (1H, t, J=6 Hz), 3.96 (3H, s), 2.96 (2H, q, J=7 Hz), 2.34-2.18 (2H, m), 1.43 (3H, t, J=7 Hz), 1.15 (3H, t, J=7 Hz).

Reference Example 32

4-(5-{1-[4-(5-Ethyl-1,2,4-oxadiazol-3-yl)phenoxy]propyl}-1,2,4-oxadiazol-3-yl)-2-fluorobenzoic acid

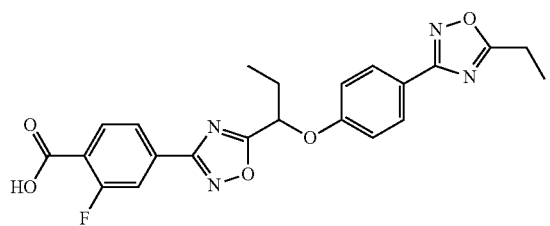

The synthesis was carried out in the same manner as in Reference Example 8, except that the compound obtained in Reference Example 31 (1.94 mg, 4.29 mmol) was used in place of methyl 2-fluoro-4-(5-{1-[4-(5-isopropyl-1,2,4-oxadiazol-3-yl)phenoxy]propyl}-1,2,4-oxadiazol-3-yl)benzoate. Thus, the title compound (1.66 g, yield: 88%) was obtained.

$^1$H-NMR (400 MHz, CDCl$_3$) δ ppm: 8.16-8.14 (1H, m), 8.01 (2H, d, J=9 Hz), 7.97 (1H, dd, J=8 Hz, 2 Hz), 7.92 (1H, dd, J=11 Hz, 2 Hz), 7.07 (2H, d, J=9 Hz), 5.52 (1H, t, J=6 Hz), 2.96 (2H, q, J=8 Hz), 2.31-2.24 (2H, m), 1.43 (3H, t, J=8 Hz), 1.15 (3H, t, J=7 Hz).

Reference Example 33

(2S)-2-{[4-(5-{1-[4-(5-ethyl-1,2,4-oxadiazol-3-yl)phenoxy]propyl}-1,2,4-oxadiazol-3-yl)-2-fluorobenzoyl]amino}propyl N-(tert-butoxycarbonyl)glycinate

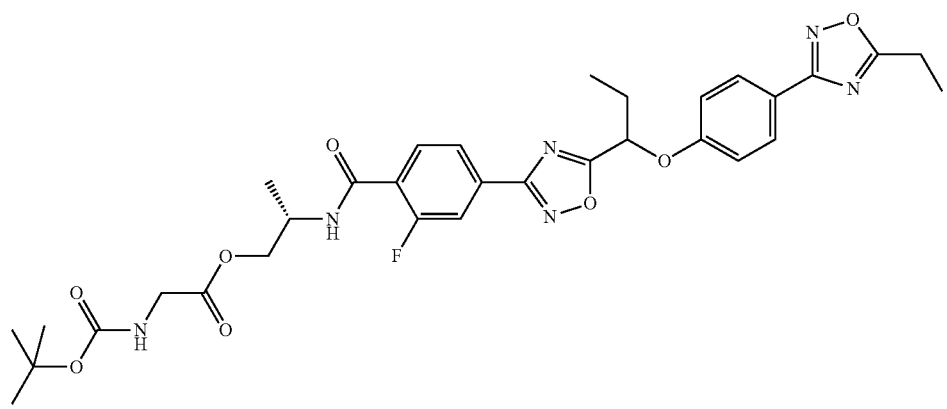 [SMILES: CCc1nc(-c2ccc(OC(CC)c3nc(-c4ccc(C(=O)N[C@@H](C)COC(=O)CNC(=O)OC(C)(C)C)c(F)c4)no3)cc2)no1]

The synthesis was carried out in the same manner as in Reference Example 14, except that the compound obtained in Example 20 that will be described below (280 mg, 0.565 mmol) was used in place of 2-fluoro-N-[(1R)-2-hydroxy-1-methylethyl]-4-(5-{1-[4-(5-isopropyl-1,2,4-oxadiazol-3-yl)phenoxy]propyl}-1,2,4-oxadiazol-3-yl)benzamide. Thus, the title compound (210 mg, yield: 98%) was obtained.

$^1$H-NMR (400 MHz, CDCl$_3$) δ ppm: 8.19-8.15 (1H, m), 8.02-7.97 (3H, m), 7.86 (1H, dd, J=11 Hz, 2 Hz), 7.07 (2H, d, J=9 Hz), 6.83-6.78 (1H, m), 5.51 (1H, t, J=6 Hz), 5.06-5.01 (1H, m), 4.59-4.52 (1H, m), 4.28 (2H, br-dd, J=12 Hz, 4 Hz), 3.95 (2H, br-d, J=5 Hz), 2.95 (2H, q, J=8 Hz), 2.32-2.25 (2H, m), 1.45-1.41 (12H, m), 1.32 (3H, d, J=7 Hz), 1.15 (3H, t, J=7 Hz).

Reference Example 34

(2R)-2-{[4-(5-{1-[4-(5-ethyl-1,2,4-oxadiazol-3-yl)phenoxy]propyl}-1,2,4-oxadiazol-3-yl)-2-fluorobenzoyl]amino}propyl N-(tert-butoxycarbonyl)glycinate

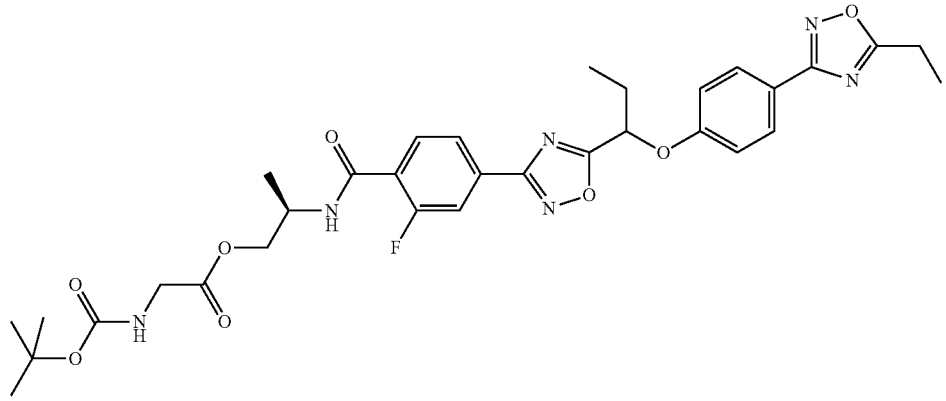 [SMILES: CCc1nc(-c2ccc(OC(CC)c3nc(-c4ccc(C(=O)N[C@H](C)COC(=O)CNC(=O)OC(C)(C)C)c(F)c4)no3)cc2)no1]

The synthesis was carried out in the same manner as in Reference Example 14, except that the compound obtained in Example 21 that will be described below (183 mg, 0.369 mmol) was used in place of 2-fluoro-N-[(1R)-2-hydroxy-1-methylethyl]-4-(5-{1-[4-(5-isopropyl-1,2,4-oxadiazol-3-yl)phenoxy]propyl}-1,2,4-oxadiazol-3-yl)benzamide. Thus, the title compound (210 mg, yield: 87%) was obtained.

$^1$H-NMR (400 MHz, CDCl$_3$) δ ppm: 8.20-8.18 (1H, m), 8.02-7.97 (3H, m), 7.86 (1H, dd, J=11 Hz, 2 Hz), 7.07 (2H, d, J=9 Hz), 6.82-6.77 (1H, m), 5.51 (1H, t, J=6 Hz), 5.04-5.00 (1H, m), 4.59-4.52 (1H, m), 4.28 (2H, br-dd, J=12 Hz, 4 Hz), 3.95 (2H, br-d, J=5 Hz), 2.95 (2H, q, J=8 Hz), 2.34-2.20 (2H, m), 1.45-1.41 (12H, m), 1.32 (3H, d, J=7 Hz), 1.15 (3H, t, J=7 Hz).

Reference Example 35

2-{[4-(5-{1-[4-(5-Ethyl-1,2,4-oxadiazol-3-yl)phenoxy]propyl}-1,2,4-oxadiazol-3-yl)-2-fluorobenzoyl]amino}-2-methylpropyl N-(tert-butoxycarbonyl)glycinate

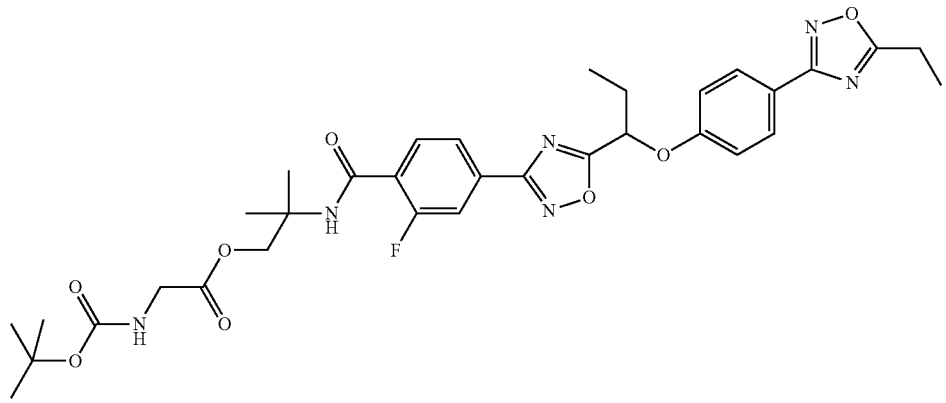 [SMILES: CCc1nc(-c2ccc(OC(CC)c3nc(-c4ccc(C(=O)NC(C)(C)COC(=O)CNC(=O)OC(C)(C)C)c(F)c4)no3)cc2)no1]

The synthesis was carried out in the same manner as in Reference Example 14, except that the compound obtained in Example 22 that will be described below (355 mg, 0.697 mmol) was used in place of 2-fluoro-N-[(1R)-2-hydroxy-1-methylethyl]-4-(5-{1-[4-(5-isopropyl-1,2,4-oxadiazol-3-yl)phenoxy]propyl}-1,2,4-oxadiazol-3-yl)benzamide. Thus, the title compound (360 mg, yield: 77%) was obtained.

$^1$H-NMR (400 MHz, CDCl$_3$) δ ppm: 8.15-8.11 (1H, m), 8.02-7.96 (3H, m), 7.84 (1H, dd, J=11 Hz, 2 Hz), 7.07 (2H, d, J=9 Hz), 6.68-6.65 (1H, m), 5.51 (1H, t, J=6 Hz), 5.04-4.99 (1H, m), 4.42 (2H, s), 3.95 (2H, br-d, J=6 Hz), 2.95 (2H, q, J=8 Hz), 2.34-2.20 (2H, m), 1.49 (6H, s), 1.45-1.41 (12H, m), 1.15 (3H, t, J=7 Hz).

Reference Example 36

Ethyl 2-[4-(5-cyclopropyl-1,2,4-oxadiazol-3-yl)phenoxy]butanoate

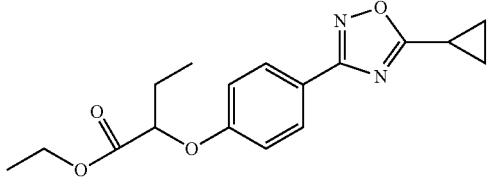 [SMILES: CCOC(=O)C(CC)Oc1ccc(-c2noc(C3CC3)n2)cc1]

The synthesis was carried out in the same manner as in Reference Example 5, except that the compound obtained in Reference Example 4 (4.00 g, 15.0 mmol) was used, and cyclopropanecarbonyl chloride (1.52 mL, 16.5 mmol) was used in place of isobutyric acid chloride. Thus, the title compound (2.01 g, yield: 42%) was obtained.

$^1$H-NMR (400 MHz, CDCl$_3$) δ ppm: 7.96 (2H, d, J=9 Hz), 6.94 (2H, d, J=9 Hz), 4.62 (1H, t, J=6 Hz), 4.23 (2H, q, J=7 Hz), 2.26-2.21 (1H, m), 2.04-1.99 (2H, m), 1.31-1.27 (4H, m), 1.24 (3H, t, J=7 Hz), 1.09 (3H, t, J=7 Hz).

Reference Example 37

2-[4-(5-Cyclopropyl-1,2,4-oxadiazol-3-yl)phenoxy]butanoic acid

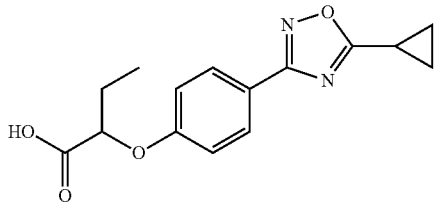 [SMILES: CCC(Oc1ccc(-c2noc(C3CC3)n2)cc1)C(=O)O]

The synthesis was carried out in the same manner as in Reference Example 6, except that the compound obtained in Reference Example 36 (2.01 g, 6.35 mmol) was used in place of ethyl 2-[4-(5-isopropyl-1,2,4-oxadiazol-3-yl)phenoxy]butanoate. Thus, the title compound (1.83 g, yield: 100%) was obtained.

$^1$H-NMR (400 MHz, CDCl$_3$) δ ppm: 7.96 (2H, d, J=9 Hz), 6.97 (2H, d, J=9 Hz), 4.68 (1H, t, J=6 Hz), 2.28-2.24 (1H, m), 2.11-2.03 (2H, m), 1.33-1.22 (4H, m), 1.13 (3H, t, J=7 Hz).

Reference Example 38

Methyl 4-(5-{1-[4-(5-cyclopropyl-1,2,4-oxadiazol-3-yl)phenoxy]propyl}-1,2,4-oxadiazol-3-yl)-2-fluorobenzoate

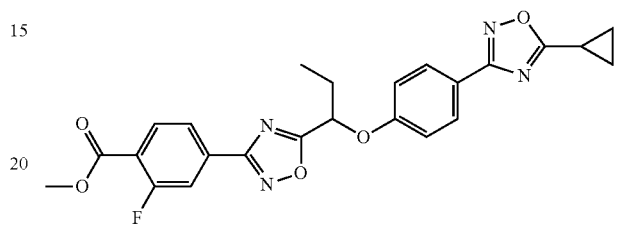

The synthesis was carried out in the same manner as in Reference Example 7, except that the compound obtained in Reference Example 37 (951 mg, 3.30 mmol) was used in place of 2-[4-(5-isopropyl-1,2,4-oxadiazol-3-yl)phenoxy]butanoic acid. Thus, the title compound (930 mg, yield: 61%) was obtained.

$^1$H-NMR (400 MHz, CDCl$_3$) δ ppm: 8.07-8.03 (1H, m), 7.97 (2H, d, J=9 Hz), 7.94-7.86 (2H, m), 7.06 (2H, d, J=9 Hz), 5.51 (1H, t, J=6 Hz), 3.97 (3H, s), 2.34-2.20 (3H, m), 1.31-1.21 (4H, m), 1.15 (3H, t, J=7 Hz).

Reference Example 39

4-(5-{1-[4-(5-Cyclopropyl-1,2,4-oxadiazol-3-yl)phenoxy]propyl}-1,2,4-oxadiazol-3-yl)-2-fluorobenzoic acid

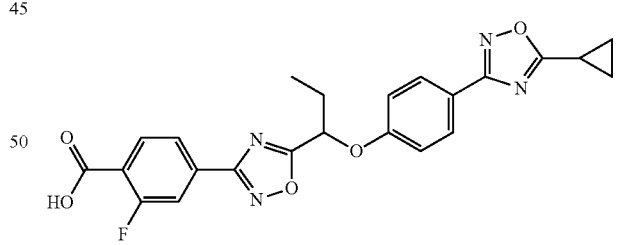

The synthesis was carried out in the same manner as in Reference Example 8, except that the compound obtained in Reference Example 38 (930 mg, 2.00 mmol) was used in place of methyl 2-fluoro-4-(5-{1-[4-(5-isopropyl-1,2,4-oxadiazol-3-yl)phenoxy]propyl}-1,2,4-oxadiazol-3-yl)benzoate. Thus, the title compound (900 mg, yield: 100%) was obtained.

$^1$H-NMR (400 MHz, CDCl$_3$) δ ppm: 8.16-8.12 (1H, m), 7.98-7.95 (3H, m), 7.91 (1H, dd, J=11 Hz, 2 Hz), 7.06 (2H, d, J=9 Hz), 5.51 (1H, t, J=7 Hz), 2.34-2.20 (3H, m), 1.31-1.21 (4H, m), 1.15 (3H, t, J=7 Hz).

Reference Example 40

(2R)-2-{[4-(5-{1-[4-(5-cyclopropyl-1,2,4-oxadiazol-3-yl)phenoxy]propyl}-1,2,4-oxadiazol-3-yl)-2-fluorobenzoyl]amino}propyl N-(tert-butoxycarbonyl)glycinate

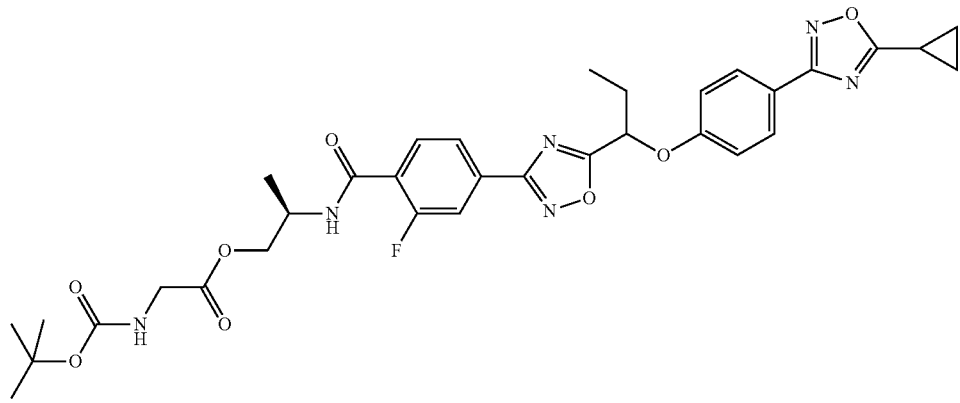 [SMILES: CCC(Oc1ccc(-c2noc(C3CC3)n2)cc1)c1nc(-c2ccc(C(=O)N[C@H](C)COC(=O)CNC(=O)OC(C)(C)C)c(F)c2)no1]

The synthesis was carried out in the same manner as in Reference Example 14, except that the compound obtained in Example 27 that will be described below (243 mg, 0.479 mmol) was used in place of 2-fluoro-N-[(1R)-2-hydroxy-1-methylethyl]-4-(5-{1-[4-(5-isopropyl-1,2,4-oxadiazol-3-yl)phenoxy]propyl}-1,2,4-oxadiazol-3-yl)benzamide. Thus, the title compound (260 mg, yield: 82%) was obtained.

$^1$H-NMR (400 MHz, CDCl$_3$) δ ppm: 8.20-8.16 (1H, m), 7.99-7.96 (3H, m), 7.86 (1H, dd, J=12 Hz, 2 Hz), 7.06 (2H, d, J=9 Hz), 6.82-6.77 (1H, m), 5.50 (1H, t, J=6 Hz), 5.05-5.00 (1H, m), 4.60-4.51 (1H, m), 4.28 (2H, br-dd, J=12 Hz, 4 Hz), 3.95 (2H, br-d, J=6 Hz), 2.34-2.19 (3H, m), 1.43 (9H, s), 1.32 (3H, d, J=7 Hz), 1.29-1.29 (4H, m), 1.14 (3H, t, J=7 Hz).

Reference Example 41

Tert-butyl 4-cyano-2-fluorobenzoate

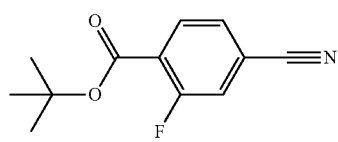 [SMILES: CC(C)(C)OC(=O)c1ccc(C#N)cc1F]

Di-tert-butyl dicarbonate (145.4 g, 666.2 mmol) was added to a tert-butyl alcohol (1000 mL)-tetrahydrofuran (500 mL) solution of 4-cyano-2-fluorobenzoic acid (100.0 g, 605.6 mmol), and the mixture was stirred for 3 hours at 60° C. The reaction mixture was cooled to room temperature, and the insoluble matter was removed by filtration through Celite. The solvent was distilled off under reduced pressure. Thus, a crude product of the title compound was obtained.

Reference Example 42

Tert-butyl 4-amino(hydroxyimino)methyl-2-fluorobenzoate

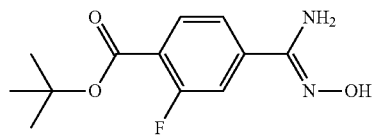 [SMILES: CC(C)(C)OC(=O)c1ccc(/C(N)=N/O)cc1F]

A 50% aqueous solution of hydroxylamine (60 mL, 100 mmol) was added to an ethanol (100 mL)-tetrahydrofuran (50 mL) solution of the compound obtained in Reference Example 41 (11.0 g, 66.6 mmol), and the mixture was stirred for 2 hours at 80° C. The reaction mixture was cooled to room temperature, and then the solvent was distilled off under reduced pressure. The resulting residue was washed with water, and was dried under reduced pressure at 40° C. for two days. Thus, the title compound (150.0 g, yield: 98%) was obtained.

$^1$H-NMR (400 MHz, CDCl$_3$) δ ppm: 7.89 (1H, t, J=8 Hz), 7.44 (2H, dd, J=8, 2 Hz), 7.39 (2H, dd, J=11, 2 Hz), 4.90 (2H, s), 1.60 (9H, s).

Reference Example 43

N',4-dihydroxybenzenecarboxylmidamide

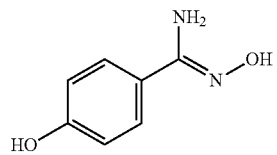 [SMILES: N/C(=N\O)c1ccc(O)cc1]

A 50% aqueous solution of hydroxylamine (13.3 mL, 202 mmol) was added to an ethanol (300 mL) solution of 4-cyanophenol (20.0 g, 168 mmol) at room temperature, and the mixture was stirred for 2 hours at 80° C. The reaction mixture was cooled to room temperature, subsequently the solvent was distilled off under reduced pressure, and the resulting residue was washed with water and ethyl acetate. Thus, the title compound (21.9 g, yield: 86%) was obtained.

$^1$H-NMR (400 MHz, DMSO-$d_6$) (ppm: 9.59 (1H, s), 9.35 (1H, s), 7.47 (2H, d, J=9 Hz), 6.73 (2H, d, J=9 Hz), 5.63 (2H, s).

Reference Example 44

4-(5-Isopropyl-1,2,4-oxadiazol-3-yl)phenol

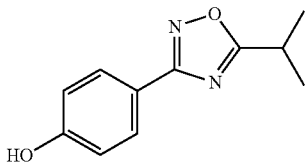

Isobutyric anhydride (16.6 mL, 99.3 mmol) was added to an N,N-dimethylformamide (150 mL) solution of the compound obtained in Reference Example 43 (15.0 g, 99.3 mmol) at room temperature, and the mixture was stirred for 30 minutes at 0° C. Subsequently, the mixture was heated to 100° C. and stirred for 7 hours. The reaction mixture was cooled to room temperature, subsequently water was added thereto, and the mixture was subjected to extraction 2 times with ethyl acetate. The organic layer thus obtained was washed with a saturated aqueous solution of sodium hydrogen carbonate and with 10% brine, and then was dried over anhydrous sodium sulfate. The solvent was distilled off under reduced pressure, and the resulting residue was washed with hexane-ethyl acetate (10:1, v/v). Thus, the title compound (18.9 g, yield: 93%) was obtained.

$^1$H-NMR (400 MHz, CDCl$_3$) δ ppm: 7.97 (2H, d, J=9 Hz), 6.91 (2H, d, J=9 Hz), 5.39 (1H, s), 3.33-3.22 (1H, m), 1.45 (6H, d, J=7 Hz).

Reference Example 45

(2R)-2-[4-(5-isopropyl-1,2,4-oxadiazol-3-yl)phenoxy]butyric acid

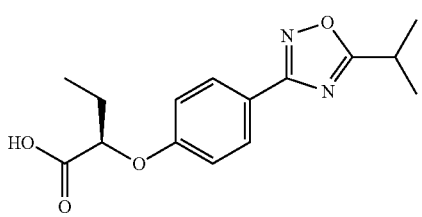 [SMILES: CC[C@@H](Oc1ccc(-c2noc(C(C)C)n2)cc1)C(=O)O]

A 1,4-dioxane (100 mL) solution of the compound obtained in Reference Example 44 was added to a 60% dioxane (700 mL) solution of sodium hydride (18.8 g, 0.49 mol) at 0° C., and the mixture was stirred for 10 minutes at room temperature. Subsequently, a dioxane (100 mL) solution of (S)-2-chlorobutyric acid (18.0 g, 147 mmol) was added to the reaction mixture, and the mixture was stirred for 4 hours at 80° C. The reaction mixture was cooled to 0° C., and then a saturated aqueous solution of ammonium chloride was added thereto. 2 N hydrochloric acid was added to the mixture until a pH value of 3 was obtained. The mixture was subjected to extraction three times with ethyl acetate, and the organic layer thus obtained was washed with water and saturated brine and then was dried over anhydrous sodium sulfate. The solvent was distilled off under reduced pressure, and the resulting residue was washed with hexane-ethyl acetate (1:1, v/v). Thus, the title compound (30.5 g, yield: 86%) was obtained.

$^1$H-NMR (500 MHz, CDCl$_3$) δ ppm: 8.00 (2H, d, J=9 Hz), 6.98 (2H, d, J=9 Hz), 4.69 (1H, t, J=6 Hz), 3.32-3.24 (1H, m), 2.08-2.05 (2H, m), 1.45 (6H, d, J=7 Hz), 1.13 (3H, t, J=7 Hz).

Reference Example 46

Tert-butyl 2-fluoro-4-(5-{(1R)-1-[4-(5-isopropyl-1,2,4-oxadiazol-3-yl)phenoxy]propyl}-1,2,4-oxadiazol-3-yl)benzoate

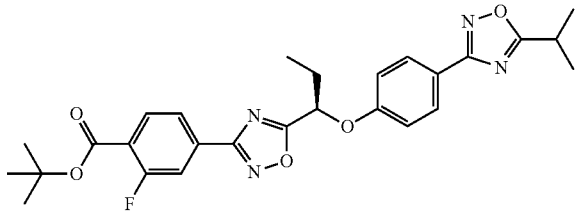 [SMILES: CC[C@@H](Oc1ccc(-c2noc(C(C)C)n2)cc1)c1nc(-c2ccc(C(=O)OC(C)(C)C)c(F)c2)no1]

To an N,N-dimethylformamide (500 mL) solution of the compound obtained in Reference Example 45 (30.6 g, 105 mmol), 1-hydroxybenzotriazole monohydrate (14.2 mg, 105 mmol) and N-(3-dimethylaminopropyl)-N'-ethylcarbodiimide (40.3 g, 210 mmol) were added at room temperature, and the mixture was stirred for 30 minutes at the same temperature. The compound obtained in Reference Example 42 (26.8 g, 105 mmol) was added thereto, and the mixture was stirred for 30 minutes and was further stirred for 4 hours at 100° C. The reaction mixture was cooled to room temperature, subsequently water was added to the reaction mixture, and the mixture was subjected to extraction two times with ethyl acetate. The organic layer thus obtained was washed with water and 10% brine, and then was dried over anhydrous sodium sulfate. The solvent was distilled off under reduced pressure, and the resulting residue was purified by silica gel column chromatography (hexane:ethyl acetate=95:5→85:15, v/v). Thus, the title compound (45.2 g, yield: 84%) was obtained.

¹H-NMR (400 MHz, CDCl₃) δ ppm: 8.01 (2H, d, J=9 Hz), 7.96 (1H, t, J=8 Hz), 7.89 (1H, dd, J=8, 2 Hz), 7.83 (1H, dd, J=11, 1 Hz), 7.07 (2H, d, J=9 Hz), 5.50 (1H, t, J=6 Hz), 3.31-3.20 (1H, m), 2.36-2.18 (2H, m), 1.61 (9H, s), 1.43 (6H, d, J=7 Hz), 1.15 (3H, t, J=7 Hz).

Reference Example 47

2-Fluoro-4-(5-{(1R)-1-[4-(5-isopropyl-1,2,4-oxadiazol-3-yl)phenoxy]propyl}-1,2,4-oxadiazol-3-yl)benzoic acid

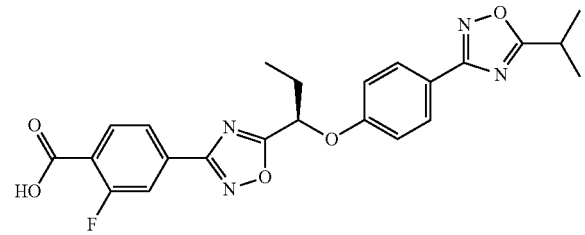 [SMILES: CC[C@@H](Oc1ccc(-c2noc(C(C)C)n2)cc1)c1nc(-c2ccc(C(=O)O)c(F)c2)no1]

Trifluoroacetic acid (300 mL) was added to a dichloromethane (100 mL) solution of the compound obtained in Reference Example 46 (45.2 g, 89.4 mmol), and the mixture was stirred for 2 hours at room temperature. The reaction mixture was concentrated under reduced pressure, and was azeotropically boiled with toluene (100 mL) for two times. Thus, the title compound (33.1 g, yield: 82%) was obtained.

¹H-NMR (400 MHz, CDCl₃) δ ppm: 8.13 (1H, t, J=8 Hz), 8.01 (2H, d, J=9 Hz), 7.96 (1H, d, J=8 Hz), 7.90 (1H, d, J=11 Hz), 7.07 (2H, d, J=9 Hz), 5.51 (1H, t, J=7 Hz), 3.28-3.23 (1H, m), 2.34-2.20 (2H, m), 1.43 (6H, d, J=7 Hz), 1.15 (3H, t, J=7 Hz).

Example 1

4-[2-Fluoro-4-(5-{1-[4-(5-isopropyl-1,2,4-oxadiazol-3-yl)phenoxy]propyl}-1,2,4-oxadiazol-3-yl)benzoyl]morpholine

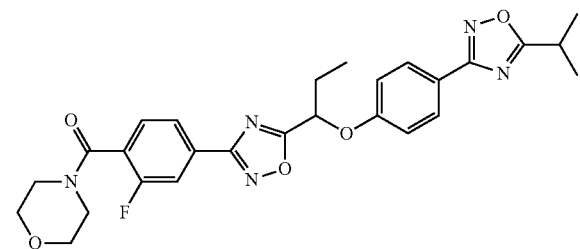 [SMILES: CCC(Oc1ccc(-c2noc(C(C)C)n2)cc1)c1nc(-c2ccc(C(=O)N3CCOCC3)c(F)c2)no1]

To a methylene chloride (1.60 mL) solution of the compound obtained in Reference Example 8 (70.0 mg, 0.155 mmol), 1-hydroxybenzotriazole monohydrate (28.4 mg, 0.186 mmol) and N-(3-dimethylaminopropyl)-N'-ethylcarbodiimide (35.6 mg, 0.186 mmol) were added at room temperature, and the mixture was stirred for 15 minutes. Morpholine (16.2 μL, 0.186 mmol) was added thereto, and the mixture was stirred for another one hour. A saturated aqueous solution of sodium hydrogen carbonate was added to the reaction mixture, and the mixture was subjected to extraction two times with methylene chloride. The extract was dried over anhydrous sodium sulfate. The solvent was distilled off under reduced pressure, and the resulting residue was purified by silica gel column chromatography (hexane:ethyl acetate=1:1, v/v). Thus, the title compound (80 mg, yield: 100%) was obtained.

¹H-NMR (400 MHz, CDCl₃) δ ppm: 8.04-7.85 (4H, m), 7.58-7.52 (1H, m), 7.11-7.07 (2H, m), 5.53 (1H, m), 3.90-3.63 (6H, m), 3.42-3.23 (3H, m), 2.38-2.22 (2H, m), 1.46 (6H, d, J=7 Hz), 1.17 (3H, t, J=7 Hz); MS (FAB⁺) m/z: 522 [M+H]⁺.

Example 2

N-[(1S)-2-hydroxy-1-methylethyl]-4-(5-{1-[4-(5-isopropyl-1,2,4-oxadiazol-3-yl)phenoxy]propyl}-1,2,4-oxadiazol-3-yl)-2-methylbenzamide

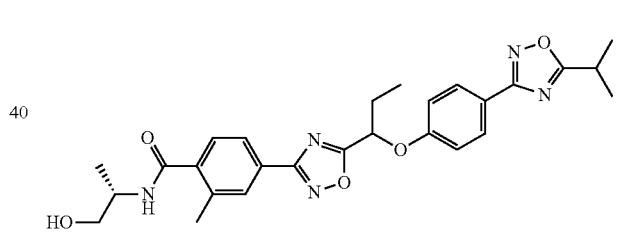

The synthesis was carried out in the same manner as in Example 1, except that the compound obtained in Reference Example 13 (101 mg, 0.225 mmol) was used in place of 2-fluoro-4-(5-{1-[4-(5-isopropyl-1,2,4-oxadiazol-3-yl)phenoxy]propyl}-1,2,4-oxadiazol-3-yl)benzoic acid, and (S)-(+)-2-amino-1-propanol (26 μL, 0.338 mmol) was used in place of morpholine. Thus, the title compound (17 mg, yield: 15%) was obtained.

¹H-NMR (400 MHz, CDCl₃) δ ppm: 8.04-7.92 (4H, m), 7.49 (1H, d, J=7 Hz), 7.10 (2H, d, J=8 Hz), 6.10-6.00 (1H, br-s), 5.52 (1H, t, J=7 Hz), 4.37-4.25 (1H, m), 3.87-3.64 (2H, m), 3.31-3.25 (1H, m), 2.53 (3H, s), 2.38-2.20 (2H, m), 1.70-1.50 (1H, br-s), 1.46 (6H, d, J=7 Hz), 1.32 (3H, d, J=7 Hz), 1.17 (3H, t, J=7 Hz); MS (ESI) m/z: 507 [M+H]⁺.

Example 3

2-Fluoro-4-(5-{1-[4-(5-isopropyl-1,2,4-oxadiazol-3-yl)phenoxy]propyl}-1,2,4-oxadiazol-3-yl)-N-(2-methoxyethyl)benzamide

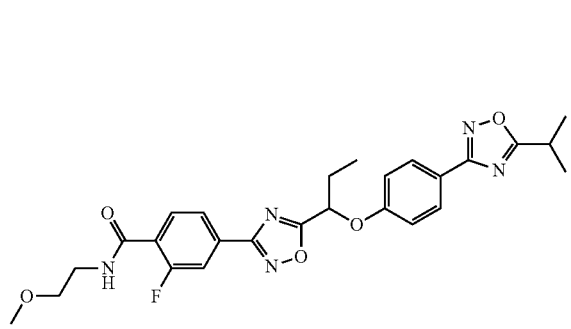 [SMILES: CCC(Oc1ccc(-c2noc(C(C)C)n2)cc1)c1nc(-c2ccc(C(=O)NCCOC)c(F)c2)no1]

The synthesis was carried out in the same manner as in Example 1, except that 2-methoxyethylamine (16.0 μL, 0.186 mmol) was used in place of morpholine. Thus, the title compound (78 mg, yield: 100%) was obtained.

¹H-NMR (400 MHz, CDCl₃) δ ppm: 8.23 (1H, t, J=8 Hz), 8.05-7.86 (4H, m), 7.13-7.08 (3H, m), 5.53 (1H, d, J=7 Hz), 3.78-3.59 (4H, m), 3.44 (3H, s), 3.32-3.23 (1H, m), 2.38-2.22 (2H, m), 1.46 (6H, d, J=7 Hz), 1.18 (3H, t, J=7 Hz); MS (FAB⁺) m/z: 510 [M+H]⁺.

Example 4

2-Fluoro-N-(2-hydroxyethyl)-4-(5-{1-[4-(5-isopropyl-1,2,4-oxadiazol-3-yl)phenoxy]propyl}-1,2,4-oxadiazol-3-yl)benzamide

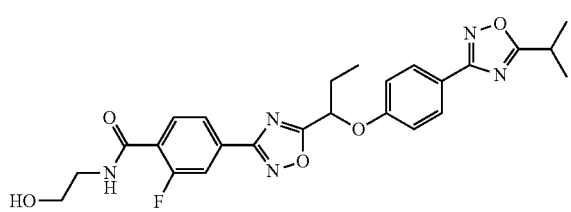 [SMILES: CCC(Oc1ccc(-c2noc(C(C)C)n2)cc1)c1nc(-c2ccc(C(=O)NCCO)c(F)c2)no1]

The synthesis was carried out in the same manner as in Example 1, except that ethanolamine (11.1 μL, 0.186 mmol) was used in place of morpholine. Thus, the title compound (71 mg, yield: 93%) was obtained.

¹H-NMR (400 MHz, CDCl₃) δ ppm: 8.24 (1H, t, J=8 Hz), 8.05-7.88 (4H, m), 7.12-7.08 (3H, m), 5.53 (1H, d, J=7 Hz), 3.93-3.68 (4H, m), 3.31-3.25 (1H, m), 2.36-2.24 (3H, m), 1.46 (6H, d, J=7 Hz), 1.17 (3H, t, J=7 Hz); MS (FAB⁺) m/z: 496 [M+H]⁺.

Example 5

2-Fluoro-4-(5-{1-[4-(5-isopropyl-1,2,4-oxadiazol-3-yl)phenoxy]propyl}-1,2,4-oxadiazol-3-yl)benzamide

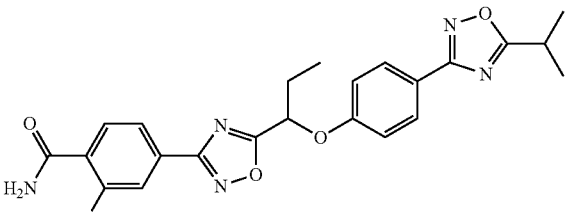

1,1'-Carbonyldiimidazole (20.2 mg, 0.124 mmol) was added to a tetrahydrofuran (0.50 mL) solution of the compound obtained in Reference Example 8 (37.5 mg, 0.0829 mmol) at room temperature, and the mixture was stirred for 30 minutes at the same temperature. Subsequently, a 28 w/w % aqueous ammonia solution (0.50 mL, excess amount) was added thereto, and the mixture was further stirred for 10 minutes at the same temperature. Water was added to the reaction mixture, and the mixture was subjected to extraction two times with ethyl acetate. The organic layer thus obtained was washed with saturated brine, and then was dried over anhydrous sodium sulfate. The solvent was distilled off under reduced pressure, and the resulting residue was purified by silica gel column chromatography (hexane:ethyl acetate=3:1→1:2, v/v). Thus, the title compound (37 mg, yield: 100%) was obtained.

¹H-NMR (400 MHz, CDCl₃) δ ppm: 8.27 (1H, t, J=8 Hz), 8.07-7.88 (4H, m), 7.11-7.06 (2H, m), 6.76-6.70 (1H, m), 5.97-5.90 (1H, m), 5.54 (1H, d, J=7 Hz), 3.31-3.25 (1H, m), 2.38-2.20 (2H, m), 1.46 (6H, d, J=7 Hz), 1.17 (3H, t, J=7 Hz); MS (FAB⁺) m/z: 452 [M+H]⁺.

Example 6

2-Fluoro-N-[(1S)-2-hydroxy-1-methylethyl]-4-(5-{1-[4-(5-isopropyl-1,2,4-oxadiazol-3-yl)phenoxy]propyl}-1,2,4-oxadiazol-3-yl)benzamide

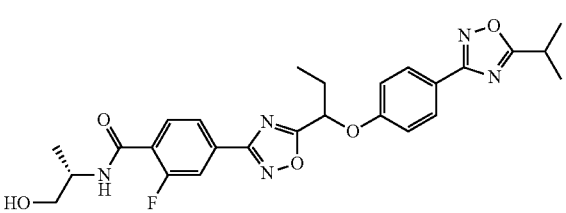 [SMILES: CCC(Oc1ccc(-c2noc(C(C)C)n2)cc1)c1nc(-c2ccc(C(=O)N[C@@H](C)CO)c(F)c2)no1]

The synthesis was carried out in the same manner as in Example 1, except that (S)-(−)-2-amino-1-propanol (16.0 μL, 0.273 mmol) was used in place of morpholine. Thus, the title compound (82 mg, yield: 88%) was obtained.

¹H-NMR (400 MHz, DMSO-d₆) δ ppm: 8.20-7.72 (5H, m), 7.75-7.72 (2H, m), 5.97 (1H, t, J=7 Hz), 4.74 (1H, t, J=7 Hz), 3.98-3.92 (1H, m), 3.45-3.20 (4H, m), 2.20-2.15 (2H, m), 1.33 (6H, d, J=7 Hz), 1.10 (3H, d, J=7 Hz), 1.02 (3H, t, J=7 Hz); MS (FAB⁺) m/z: 510 [M+H]⁺.

Example 7

2-Fluoro-N-[(1R)-2-hydroxy-1-methylethyl]-4-(5-{1-[4-(5-isopropyl-1,2,4-oxadiazol-3-yl)phenoxy]propyl}-1,2,4-oxadiazol-3-yl)benzamide

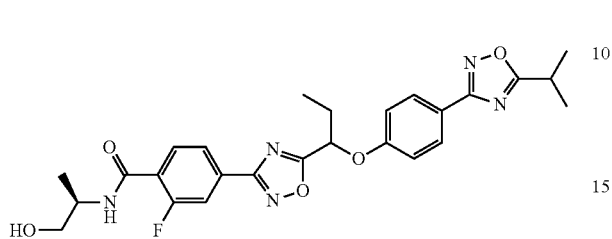

The synthesis was carried out in the same manner as in Example 1, except that (R)-(−)-2-amino-1-propanol (23.0 μL, 0.290 mmol) was used in place of morpholine. Thus, the title compound (85 mg, yield: 86%) was obtained. $^1$H-NMR (400 MHz, DMSO-$d_6$) δ ppm: 8.18 (1H, d, J=8 Hz), 7.93 (2H, d, J=9 Hz), 7.87-7.73 (2H, m), 7.22 (2H, d, J=9 Hz), 5.99 (1H, t, J=7 Hz), 4.75 (1H, t, J=6 Hz), 4.03-3.90 (1H, m), 3.48-3.38 (1H, m), 3.37-3.20 (3H, m), 2.22-2.15 (2H, m), 1.34 (6H, d, J=7 Hz), 1.11 (3H, d, J=7 Hz), 1.02 (3H, t, J=7 Hz); MS (FAB$^+$) m/z: 510 [M+H]$^+$.

Example 8

2-Fluoro-N-(2-hydroxy-1,1-dimethylethyl)-4-(5-{1-[4-(5-isopropyl-1,2,4-oxadiazol-3-yl)phenoxy]propyl}-1,2,4-oxadiazol-3-yl)benzamide

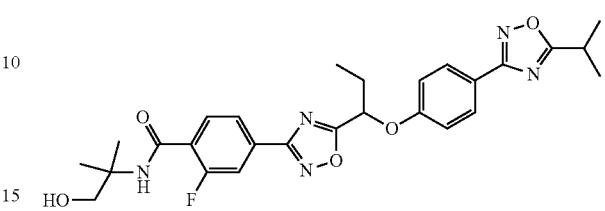

The synthesis was carried out in the same manner as in Example 1, except that 2-amino-2-methyl-1-propanol (29.5 μL, 0.332 mmol) was used in place of morpholine. Thus, the title compound (82 mg, yield: 72%) was obtained.
$^1$H-NMR (400 MHz, DMSO-$d_6$) δ ppm: 7.95-7.70 (7H, m), 7.25-7.20 (2H, m), 5.97 (1H, t, J=7 Hz), 4.88 (1H, t, J=6 Hz), 3.60-3.42 (2H, m), 3.33-3.25 (1H, m), 2.20-2.13 (1H, m), 1.32 (3H, d, J=7 Hz), 1.28 (6H, s), 1.03 (6H, d, J=7 Hz); MS (FAB$^+$) m/z: 524 [M+H]$^+$.

Example 9

2-Fluoro-N-[(1S)-1-(hydroxymethyl)propyl]-4-(5-{1-[4-(5-isopropyl-1,2,4-oxadiazol-3-yl)phenoxy]propyl}-1,2,4-oxadiazol-3-yl)benzamide

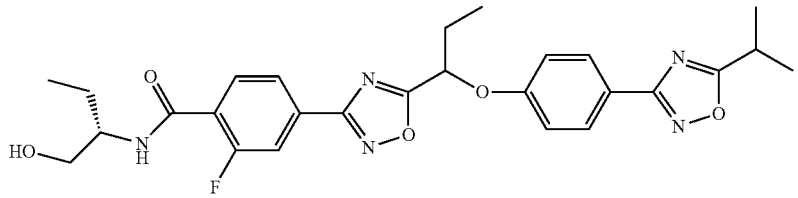 [SMILES: CCC(Oc1ccc(-c2noc(C(C)C)n2)cc1)c1nc(-c2ccc(C(=O)N[C@@H](CC)CO)c(F)c2)no1]

The synthesis was carried out in the same manner as in Example 1, except that (S)-2-aminobutan-1-ol (42.0 μL, 0.444 mmol) was used in place of morpholine. Thus, the title compound (147 mg, yield: 63%) was obtained. $^1$H-NMR (400 MHz, DMSO-$d_6$) δ ppm: 8.10 (1H, d, J=8 Hz), 7.95-7.70 (5H, m), 7.24-7.19 (2H, m), 5.97 (1H, t, J=6 Hz), 4.69 (1H, t, J=6 Hz), 3.85-3.75 (1H, m), 3.47-3.22 (3H, m), 2.20-2.13 (2H, m), 1.69-1.54 (1H, m), 1.41-1.32 (7H, m), 1.42 (3H, t, J=7 Hz), 1.09 (3H, t, J=7 Hz); MS (FAB$^+$) m/z: 524 [M+H]$^+$.

Example 10

2-Fluoro-N-[(1R)-1-(hydroxymethyl)propyl]-4-(5-{1-[4-(5-isopropyl-1,2,4-oxadiazol-3-yl)phenoxy]propyl}-1,2,4-oxadiazol-3-yl)benzamide

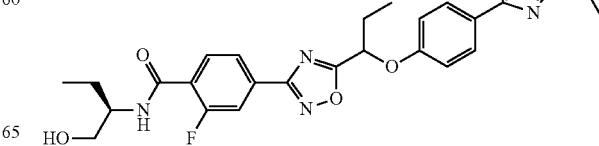

The synthesis was carried out in the same manner as in Example 1, except that (R)-2-aminobutan-1-ol (16.0 μL, 0.186 mmol) was used in place of morpholine. Thus, the title compound (297 mg, yield: 86%) was obtained.

$^1$H-NMR (400 MHz, CDCl$_3$) δ ppm: 8.23 (1H, t, J=8 Hz), 8.05-7.87 (4H, m), 7.13-6.85 (3H, m), 5.53 (1H, d, J=7 Hz), 4.21-4.13 (1H, m), 3.86 (1H, dd, J=11 Hz, 4 Hz), 3.76 (1H, dd, J=11 Hz, 7 Hz), 3.31-3.25 (1H, m), 2.38-2.22 (2H, m), 1.80-1.48 (3H, m), 1.46 (6H, d, J=7 Hz), 1.17 (3H, t, J=7 Hz), 1.07 (3H, t, J=7 Hz); MS (FAB$^+$) m/z: 524 [M+H]$^+$.

Example 11

2-Fluoro-N-(3-hydroxypropyl)-4-(5-{1-[4-(5-isopropyl-1,2,4-oxadiazol-3-yl)phenoxy]propyl}-1,2,4-oxadiazol-3-yl)benzamide

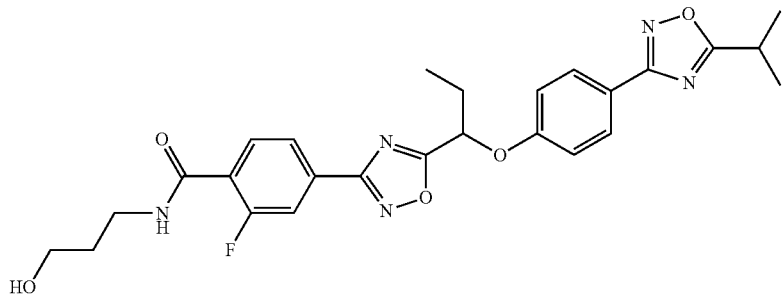 [SMILES: CCC(Oc1ccc(-c2noc(C(C)C)n2)cc1)c1nc(-c2ccc(C(=O)NCCCO)c(F)c2)no1]

The synthesis was carried out in the same manner as in Example 1, except that 3-amino-1-propanol (50 μL, 0.663 mmol) was used in place of morpholine. Thus, the title compound (210 mg, yield: 93%) was obtained.

$^1$H-NMR (400 MHz, CDCl$_3$) δ ppm: 8.17 (1H, t, J=8 Hz), 8.01-7.78 (4H, m), 7.24-7.00 (3H, m), 5.47 (1H, t, J=7 Hz), 3.78-3.63 (4H, m), 3.25-3.18 (1H, m), 2.35-2.15 (2H, m), 1.84-1.75 (2H, m), 1.41 (6H, d, J=7 Hz), 1.12 (3H, t, J=7 Hz); MS (ESI) m/z: 511 [M+H]$^+$.

Example 12

(2R)-2-{[2-fluoro-4-(5-{1-[4-(5-isopropyl-1,2,4-oxadiazol-3-yl)phenoxy]propyl}-1,2,4-oxadiazol-3-yl)benzoyl]amino}propyl glycinate hydrochloride

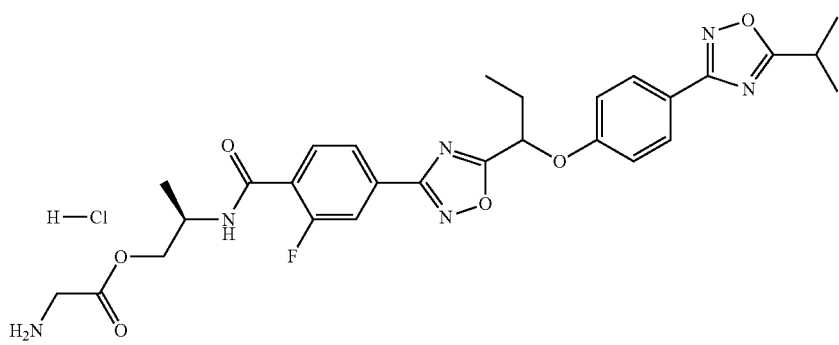

A 4 M aqueous hydrochloric acid solution (1.00 mL) was added to an ethyl acetate (1.00 mL) solution of the compound obtained in Reference Example 14 (90.6 mg, 0.136 mmol), and the mixture was stirred for 4 hours at room temperature. The solvent was distilled off from the reaction mixture under reduced pressure, and the residue was washed with diethyl ether. Thus, the title compound (52 mg, yield: 64%) was obtained.

$^1$H-NMR (400 MHz, DMSO-$d_6$) δ ppm: 8.49 (1H, d, J=8 Hz), 8.36-8.23 (2H, m), 7.95-7.71 (4H, m), 7.25-7.18 (2H, m), 5.98 (1H, t, J=7 Hz), 4.33-4.07 (3H, m), 3.79 (2H, s), 3.84-3.87 (3H, m), 2.20-2.14 (2H, m), 1.33 (6H, d, J=7 Hz), 1.17 (3H, d, J=7 Hz), 1.03 (3H, d, J=7 Hz); MS (FAB$^+$) m/z: 567 [M+H]$^+$.

Example 13

(2S)-2-{[2-fluoro-4-(5-{1-[4-(5-isopropyl-1,2,4-oxadiazol-3-yl)phenoxy]propyl}-1,2,4-oxadiazol-3-yl)benzoyl]amino}propyl glycinate hydrochloride

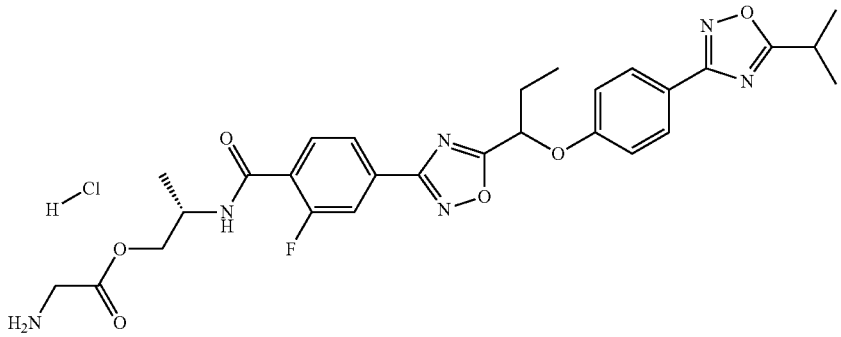 [SMILES: CCC(Oc1ccc(-c2noc(C(C)C)n2)cc1)c1nc(-c2ccc(C(=O)N[C@@H](C)COC(=O)CN)c(F)c2)no1 ; Cl]

The synthesis was carried out in the same manner as in Example 12, except that the compound obtained in Reference Example 15 (123 mg, 0.184 mmol) was used in place of (2R)-2-{[2-fluoro-4-(5-{1-[4-(5-isopropyl-1,2,4-oxadiazol-3-yl)phenoxy]propyl}-1,2,4-oxadiazol-3-yl)benzoyl]amino}propyl N-(tert-butoxycarbonyl)glycinate. Thus, the title compound (63 mg, yield: 57%) was obtained.

$^1$H-NMR (400 MHz, DMSO-$d_6$) δ ppm: 8.49 (1H, d, J=8 Hz), 8.46-8.23 (2H, m), 7.99-7.71 (4H, m), 7.30-7.25 (2H, m), 6.04 (1H, t, J=7 Hz), 4.37-4.16 (3H, m), 3.89 (2H, s), 3.84-3.87 (3H, m), 2.20-2.14 (2H, s), 1.39 (6H, d, J=7 Hz), 1.24 (3H, d, J=7 Hz), 1.09 (3H, d, J=7 Hz); MS (FAB$^+$) m/z: 567 [M+H]$^+$.

Example 14

(2R)-2-{[2-fluoro-4-(5-{1-[4-(5-isopropyl-1,2,4-oxadiazol-3-yl)phenoxy]propyl}-1,2,4-oxadiazol-3-yl)benzoyl]amino}butyl glycinate hydrochloride

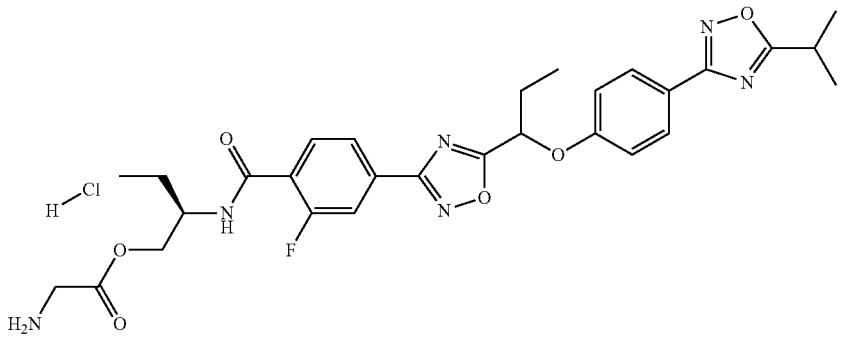

The synthesis was carried out in the same manner as in Example 12, except that the compound obtained in Reference Example 16 (358 mg, 0.523 mmol) was used in place of (2R)-2-{[2-fluoro-4-(5-{1-[4-(5-isopropyl-1,2,4-oxadiazol-3-yl)phenoxy]propyl}-1,2,4-oxadiazol-3-yl)benzoyl]amino}propyl N-(tert-butoxycarbonyl)glycinate. Thus, the title compound (308 mg, yield: 95%) was obtained.

$^1$H-NMR (400 MHz, DMSO-$d_6$) δ ppm: 8.63-8.33 (3H, m), 8.02-7.75 (5H, m), 7.32-7.24 (2H, m), 6.04 (1H, t, J=7 Hz), 4.37-4.09 (3H, m), 3.83 (2H, s), 2.26-2.21 (2H, m), 1.75-1.49 (2H, m), 1.34 (6H, d, J=7 Hz), 1.36-1.25 (1H, m), 1.13-0.83 (7H, m); MS (FAB$^+$) m/z: 581 [M+H]$^+$.

Example 15

(2S)-2-{[2-fluoro-4-(5-{1-[4-(5-isopropyl-1,2,4-oxadiazol-3-yl)phenoxy]propyl}-1,2,4-oxadiazol-3-yl)benzoyl]amino}butyl glycinate hydrochloride

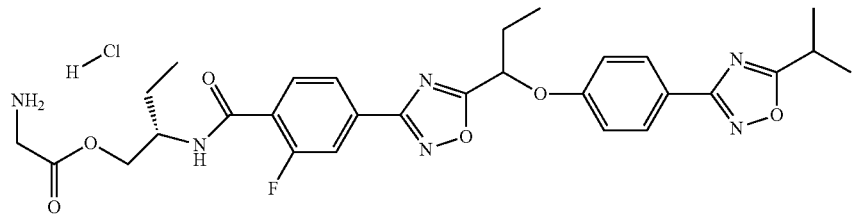

The synthesis was carried out in the same manner as in Example 12, except that the compound obtained in Reference Example 17 (274 mg, 0.403 mmol) was used in place of (2R)-2-{[2-fluoro-4-(5-{1-[4-(5-isopropyl-1,2,4-oxadiazol-3-yl)phenoxy]propyl}-1,2,4-oxadiazol-3-yl)benzoyl]amino}propyl N-(tert-butoxycarbonyl)glycinate. Thus, the title compound (49 mg, yield: 20%) was obtained.

$^1$H-NMR (400 MHz, DMSO-$d_6$) δ ppm: 8.39-8.22 (3H, m), 8.02-7.75 (4H, m), 7.29-7.27 (2H, m), 6.03 (1H, t, J=7 Hz), 4.37-4.17 (3H, m), 3.85 (2H, s), 2.28-2.19 (2H, m), 1.75-1.55 (2H, m), 1.39 (6H, d, J=7 Hz), 1.09 (3H, t, J=7 Hz), 0.97 (3H, t, J=7 Hz); MS (ESI) m/z: 581 [M+H]$^+$.

Example 16

2-{[2-Fluoro-4-(5-{1-[4-(5-isopropyl-1,2,4-oxadiazol-3-yl)phenoxy]propyl}-1,2,4-oxadiazol-3-yl)benzoyl]amino}-2-methylpropyl glycinate hydrochloride

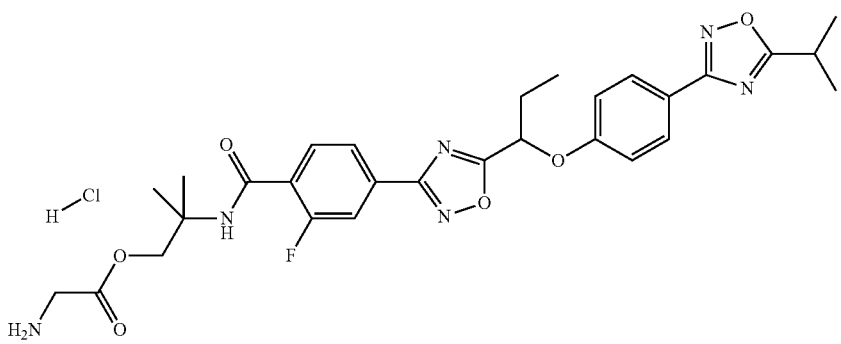 [SMILES: CCC(Oc1ccc(-c2noc(C(C)C)n2)cc1)c1nc(-c2ccc(C(=O)NC(C)(C)COC(=O)CN)c(F)c2)no1 ; Cl]

The synthesis was carried out in the same manner as in Example 12, except that the compound obtained in Reference Example 18 (169 mg, 0.523 mmol) was used in place of (2R)-2-{[2-fluoro-4-(5-{1-[4-(5-isopropyl-1,2,4-oxadiazol-3-yl)phenoxy]propyl}-1,2,4-oxadiazol-3-yl)benzoyl]amino}propyl N-(tert-butoxycarbonyl)glycinate. Thus, the title compound (129 mg, yield: 84%) was obtained.

$^1$H-NMR (400 MHz, DMSO-$d_6$) δ ppm: 8.52-8.34 (3H, m), 8.20 (1H, s), 8.01-7.72 (5H, m), 7.30-7.26 (2H, m), 6.04 (1H, t, J=7 Hz), 4.40 (2H, s), 3.87 (2H, s), 2.26-2.20 (2H, m), 1.41 (6H, s), 1.38 (6H, d, J=7 Hz), 1.38-1.36 (1H, br-s), 1.09 (3H, t, J=7 Hz); MS (FAB$^+$) m/z: 581 [M+H]$^+$.

Example 17

(2R)-2-{[2-fluoro-4-(5-{1-[4-(5-isopropyl-1,2,4-oxadiazol-3-yl)phenoxy]propyl}-1,2,4-oxadiazol-3-yl)benzoyl]amino}-2-methylpropyl glycolate

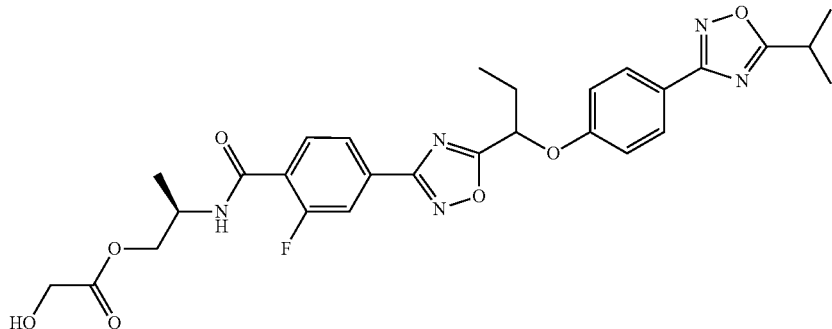 [SMILES: CCC(Oc1ccc(-c2noc(C(C)C)n2)cc1)c1nc(-c2ccc(C(=O)N[C@H](C)COC(=O)CO)c(F)c2)no1]

To a tetrahydrofuran (5.00 mL) solution of the compound obtained in Reference Example 22 (300 mg, 0.505 mmol), triphenylphosphine (58.3 mg, 0.224 mmol), dimedone (46.0 mg, 0.329 mmol) and tetrakistriphenylphosphinepalladium (58.4 mg, 0.0505 mmol) were added, and the mixture was stirred for 4 hours at room temperature. The solvent was distilled off from the reaction mixture under reduced pressure, and the resulting residue was purified by silica gel column chromatography (hexane:ethyl acetate=9:1→1:1, v/v). Thus, the title compound (252 mg, yield: 77%) was obtained.

$^1$H-NMR (400 MHz, DMSO-$d_6$) δ ppm: 8.49 (1H, d, J=8 Hz), 8.00-7.75 (5H, m), 7.25-7.18 (2H, m), 6.04 (1H, t, J=7 Hz), 5.35 (1H, t, J=7 Hz), 4.32-4.04 (6H, m), 2.26-2.22 (2H, m), 1.40 (6H, d, J=7 Hz), 1.19 (3H, d, J=7 Hz), 1.09 (3H, t, J=7 Hz); MS (FAB$^+$) m/z: 568 [M+H]$^+$.

Example 18

2-Fluoro-N-[(1S)-2-hydroxy-1-methylethyl]-4-(2-{1-[4-(5-isopropyl-1,2,4-oxadiazol-3-yl)phenoxy]propyl}-1,3-oxazol-4-yl)benzamide

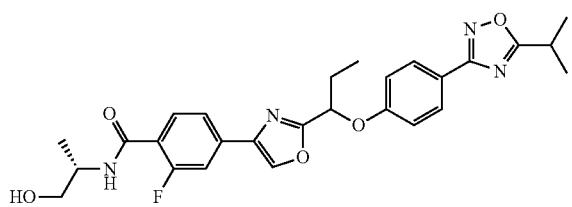 [SMILES: CCC(Oc1ccc(-c2noc(C(C)C)n2)cc1)c1nc(-c2ccc(C(=O)N[C@@H](C)CO)c(F)c2)co1]

The synthesis was carried out in the same manner as in Example 1, except that the compound obtained in Reference Example 27 (70.0 mg, 0.155 mmol) was used in place of 2-fluoro-4-(5-{1-[4-(5-isopropyl-1,2,4-oxadiazol-3-yl)phenoxy]propyl}-1,2,4-oxadiazol-3-yl)benzoic acid, and (R)-2-amino-1-propanol (14.4 μL, 0.186 mmol) was used in place of morpholine. Thus, the title compound (56 mg, yield: 72%) was obtained.

$^1$H-NMR (400 MHz, CDCl$_3$) δ ppm: 8.14 (1H, t, J=8 Hz), 8.03-7.99 (3H, m), 7.60-7.56 (2H, m), 7.15-7.10 (2H, m), 6.96-6.85 (1H, m), 5.37 (1H, t, J=7 Hz), 4.40-4.32 (1H, m), 3.83 (1H, dd, J=11 Hz, 4 Hz), 3.70 (1H, dd, J=11 Hz, 6 Hz), 3.30-3.25 (1H, m), 2.33-2.16 (3H, m), 1.46 (6H, d, J=7 Hz), 1.34 (3H, d, J=7 Hz), 1.12 (3H, t, J=7 Hz) MS (FAB$^+$) m/z: 509 [M+H]$^+$.

Example 19

(2S)-2-{[2-fluoro-4-(2-{1-[4-(5-isopropyl-1,2,4-oxadiazol-3-yl)phenoxy]propyl}-1,3-oxazol-4-yl)benzoyl]amino}propyl glycinate hydrochloride

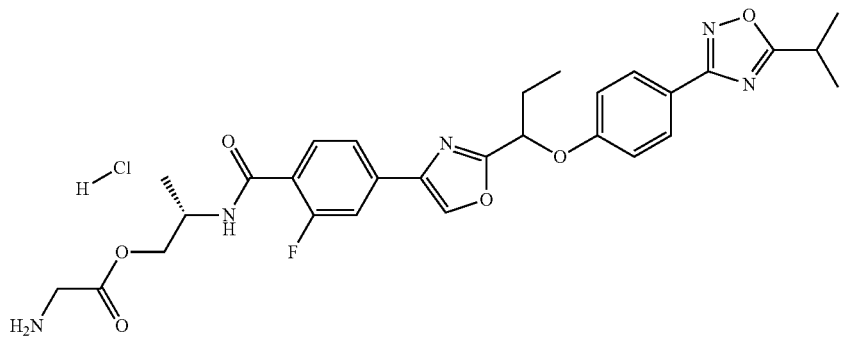

The synthesis was carried out in the same manner as in Example 12, except that the compound obtained in Reference Example 28 (123 mg, 0.184 mmol) was used in place of (2R)-2-{[2-fluoro-4-(5-{1-[4-(5-isopropyl-1,2,4-oxadiazol-3-yl)phenoxy]propyl}-1,2,4-oxadiazol-3-yl)benzoyl]amino}propyl N-(tert-butoxycarbonyl)glycinate. Thus, the title compound (19 mg, yield: 85%) was obtained.

$^1$H-NMR (400 MHz, CDCl$_3$) δ ppm: 8.73-8.57 (2H, br-s), 8.00-7.88 (4H, m), 7.46-7.02 (5H, m), 5.32 (1H, t, J=7 Hz), 4.47-4.05 (4H, m), 3.30-3.19 (1H, m), 2.33-2.09 (5H, m), 1.43 (6H, d, J=7 Hz), 1.31-1.25 (2H, m), 1.07 (3H, t, J=7 Hz); MS (FAB$^+$) m/z: 566 [M+H]$^+$.

Example 20

4-(5-{1-[4-(5-Ethyl-1,2,4-oxadiazol-3-yl)phenoxy]propyl}-1,2,4-oxadiazol-3-yl)-2-fluoro-N-[(1S)-2-hydroxy-1-methylethyl]benzamide

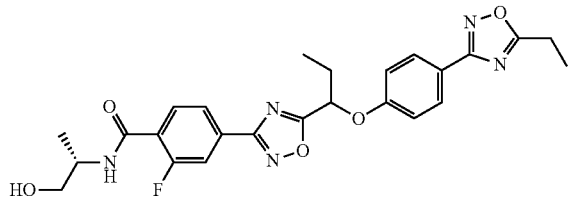

The synthesis was carried out in the same manner as in Example 6, except that the compound obtained in Reference Example 32 (300 mg, 0.684 mmol) was used in place of 2-fluoro-4-(5-{1-[4-(5-isopropyl-1,2,4-oxadiazol-3-yl)phenoxy]propyl}-1,2,4-oxadiazol-3-yl)benzoic acid. Thus, the title compound (280 mg, yield: 83%) was obtained.

$^1$H-NMR (400 MHz, CDCl$_3$) δ ppm: 8.18 (1H, t, J=8 Hz), 8.00-7.82 (4H, m), 7.08-6.86 (3H, m), 5.49 (1H, t, J=7 Hz), 4.38-4.27 (1H, m), 3.83-3.62 (2H, m), 2.93 (2H, q, J=7 Hz), 2.48-2.40 (1H, br-s), 2.33-2.15 (2H, m), 1.41 (3H, t, J=7 Hz), 1.30 (3H, d, J=7 Hz), 0.86 (3H, t, J=7 Hz); MS (ESI) m/z: 497 [M+H]$^+$.

Example 21

4-(5-{1-[4-(5-Ethyl-1,2,4-oxadiazol-3-yl)phenoxy]propyl}-1,2,4-oxadiazol-3-yl)-2-fluoro-N-[(1R)-2-hydroxy-1-methylethyl]benzamide

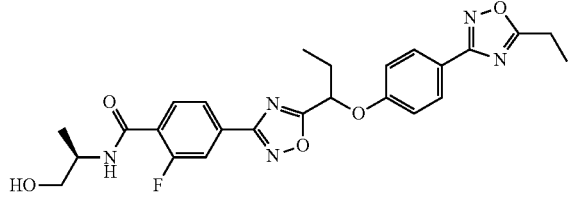 [SMILES: CCc1nc(-c2ccc(OC(CC)c3nc(-c4ccc(C(=O)N[C@H](C)CO)c(F)c4)no3)cc2)no1]

The synthesis was carried out in the same manner as in Example 7, except that the compound obtained in Reference Example 32 (300 mg, 0.684 mmol) was used in place of 2-fluoro-4-(5-{1-[4-(5-isopropyl-1,2,4-oxadiazol-3-yl)phenoxy]propyl}-1,2,4-oxadiazol-3-yl)benzoic acid. Thus, the title compound (183 mg, yield: 54%) was obtained.

$^1$H-NMR (400 MHz, CDCl$_3$) δ ppm: 8.18 (1H, t, J=8 Hz), 8.02-7.81 (4H, m), 7.08-6.86 (3H, m), 5.49 (1H, t, J=7 Hz), 4.39-4.26 (1H, m), 3.79 (1H, dd, J=11 Hz, 4 Hz), 3.66 (1H, dd, J=11 Hz, 7 Hz), 2.93 (2H, q, J=7 Hz), 2.34-2.20 (2H, m), 1.61 (1H, br-s), 1.41 (3H, t, J=7 Hz), 1.30 (3H, d, J=7 Hz), 1.13 (3H, t, J=7 Hz); MS (ESI) m/z: 497 [M+H]$^+$.

Example 22

4-(5-{1-[4-(5-Ethyl-1,2,4-oxadiazol-3-yl)phenoxy]propyl}-1,2,4-oxadiazol-3-yl)-2-fluoro-N-(2-hydroxy-1,1-dimethylethyl)benzamide

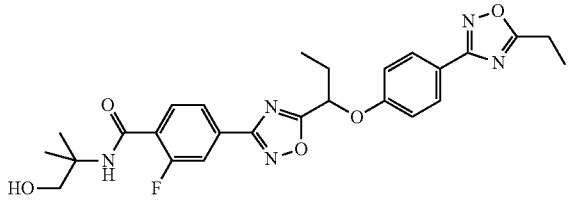 [SMILES: CCc1nc(-c2ccc(OC(CC)c3nc(-c4ccc(C(=O)NC(C)(C)CO)c(F)c4)no3)cc2)no1]

The synthesis was carried out in the same manner as in Example 8, except that the compound obtained in Reference Example 32 (400 mg, 0.912 mmol) was used in place of 2-fluoro-4-(5-{1-[4-(5-isopropyl-1,2,4-oxadiazol-3-yl)phenoxy]propyl}-1,2,4-oxadiazol-3-yl)benzoic acid. Thus, the title compound (355 mg, yield: 76%) was obtained.

$^1$H-NMR (400 MHz, CDCl$_3$) δ ppm: 8.13 (1H, t, J=7 Hz), 8.01-7.80 (4H, m), 7.08-6.83 (3H, m), 5.49 (1H, t, J=7 Hz), 4.39-4.26 (1H, br-s), 3.70 (2H, s), 2.93 (2H, q, J=7 Hz), 2.36-2.15 (2H, m), 1.43-1.37 (9H, m), 1.13 (3H, t, J=7 Hz); MS (ESI) m/z: 511 [M+H]$^+$.

Example 23

4-(5-{1-[4-(5-Ethyl-1,2,4-oxadiazol-3-yl)phenoxy]propyl}-1,2,4-oxadiazol-3-yl)-2-fluoro-N-(2-hydroxyethyl)benzamide

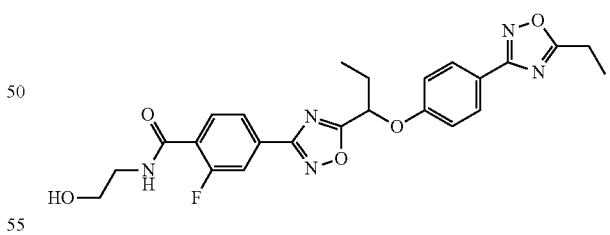

The synthesis was carried out in the same manner as in Example 4, except that the compound obtained in Reference Example 32 (200 mg, 0.456 mmol) was used in place of 2-fluoro-4-(5-{1-[4-(5-isopropyl-1,2,4-oxadiazol-3-yl)phenoxy]propyl}-1,2,4-oxadiazol-3-yl)benzoic acid. Thus, the title compound (157 mg, yield: 72%) was obtained.

$^1$H-NMR (400 MHz, CDCl$_3$) δ ppm: 8.20 (1H, t, J=8 Hz), 8.00-7.83 (4H, m), 7.24-6.98 (3H, m), 5.49 (1H, d, J=7 Hz), 3.89-3.63 (4H, m), 2.93 (2H, q, J=7 Hz), 2.35-2.15 (2H, m), 1.60-1.52 (1H, br-s), 1.41 (3H, t, J=7 Hz), 1.12 (3H, t, J=7 Hz); MS (ESI) m/z: 482 [M+H]$^+$.

Example 24

(2S)-2-{[4-(5-{1-[4-(5-ethyl-1,2,4-oxadiazol-3-yl)phenoxy]propyl}-1,2,4-oxadiazol-3-yl)-2-fluorobenzoyl]amino}propyl glycinate hydrochloride

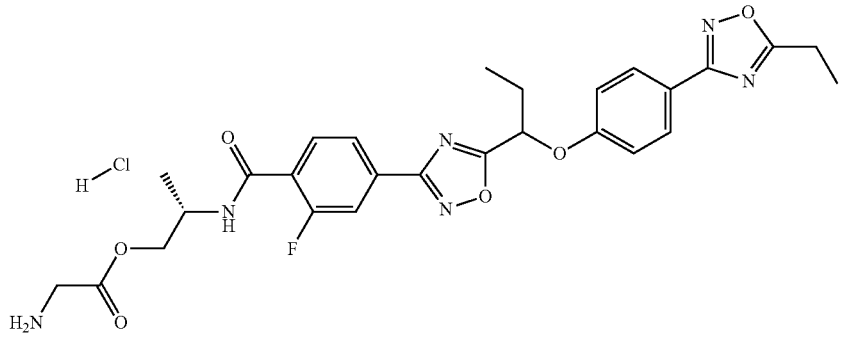

The synthesis was carried out in the same manner as in Example 12, except that the compound obtained in Reference Example 33 (360 mg, 0.552 mmol) was used in place of (2R)-2-{[2-fluoro-4-(5-{1-[4-(5-isopropyl-1,2,4-oxadiazol-3-yl)phenoxy]propyl}-1,2,4-oxadiazol-3-yl)benzoyl]amino}propyl N-(tert-butoxycarbonyl)glycinate. Thus, the title compound (244 mg, yield: 75%) was obtained.

$^1$H-NMR (400 MHz, DMSO-d$_6$) δ ppm: 8.54 (1H, d, J=8 Hz), 8.46-8.23 (2H, m), 7.99-7.71 (5H, m), 7.30-7.25 (2H, m), 5.99 (1H, t, J=7 Hz), 4.37-4.08 (3H, m), 3.78 (2H, s), 3.43-3.34 (1H, m), 2.92 (2H, q, J=7 Hz), 2.24-2.14 (2H, m), 1.30 (3H, t, J=7 Hz), 1.19 (3H, d, J=7 Hz), 1.04 (3H, t, J=7 Hz); MS (ESI) m/z: 554 [M+H]$^+$.

Example 25

(2R)-2-{[4-(5-{1-[4-(5-ethyl-1,2,4-oxadiazol-3-yl)phenoxy]propyl}-1,2,4-oxadiazol-3-yl)-2-fluorobenzoyl]amino}propyl glycinate hydrochloride

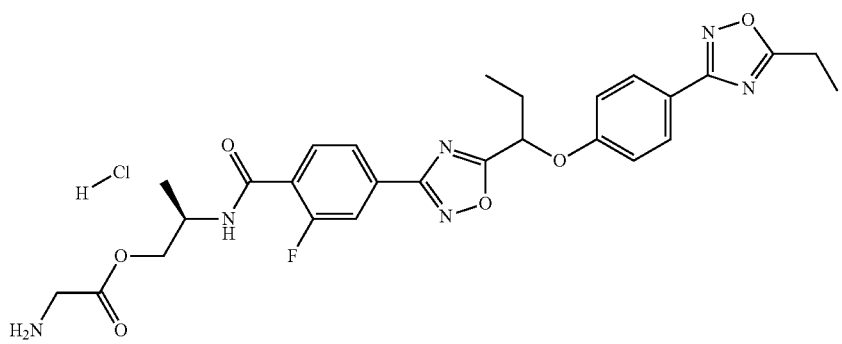

The synthesis was carried out in the same manner as in Example 12, except that the compound obtained in Reference Example 34 (210 mg, 0.322 mmol) was used in place of (2R)-2-{[2-fluoro-4-(5-{1-[4-(5-isopropyl-1,2,4-oxadiazol-3-yl)phenoxy]propyl}-1,2,4-oxadiazol-3-yl)benzoyl]amino}propyl N-(tert-butoxycarbonyl)glycinate. Thus, the title compound (170 mg, yield: 90%) was obtained.

$^1$H-NMR (400 MHz, DMSO-d$_6$) δ ppm: 8.54 (1H, d, J=8 Hz), 8.46-8.23 (3H, m), 7.95-7.74 (5H, m), 7.27-7.19 (2H, m), 6.00 (1H, t, J=7 Hz), 4.37-4.08 (3H, m), 3.78 (2H, s), 2.97 (2H, q, J=7 Hz), 2.24-2.14 (2H, m), 1.30 (3H, t, J=7 Hz), 1.19 (3H, d, J=7 Hz), 1.04 (3H, t, J=7 Hz); MS (ESI) m/z: 554 [M+H]$^+$.

Example 26

2-{[4-(5-{1-[4-(5-Ethyl-1,2,4-oxadiazol-3-yl)phenoxy]propyl}-1,2,4-oxadiazol-3-yl)-2-fluorobenzoyl]amino}-2-methylpropyl glycinate hydrochloride

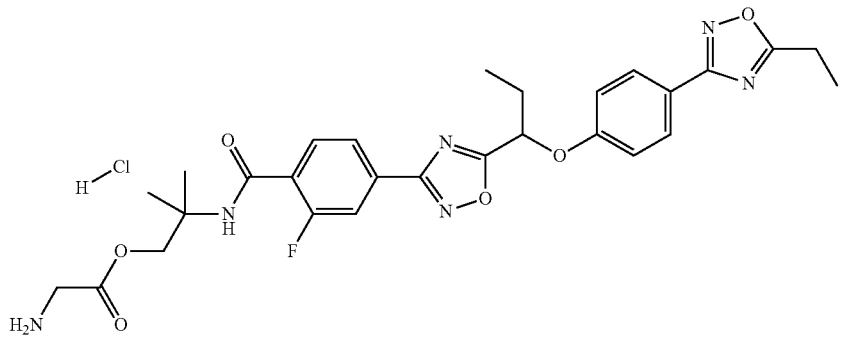

The synthesis was carried out in the same manner as in Example 12, except that the compound obtained in Reference Example 35 (360 mg, 0.539 mmol) was used in place of (2R)-2-{[2-fluoro-4-(5-{1-[4-(5-isopropyl-1,2,4-oxadiazol-3-yl)phenoxy]propyl}-1,2,4-oxadiazol-3-yl)benzoyl]amino}propyl N-(tert-butoxycarbonyl)glycinate. Thus, the title compound (224 mg, yield: 69%) was obtained.

$^1$H-NMR (400 MHz, DMSO-$d_6$) δ ppm: 8.50-8.40 (2H, br-s), 8.20 (1H, s), 8.00-7.24 (7H, m), 6.04 (1H, t, J=7 Hz), 4.40 (2H, s), 3.87 (2H, s), 3.66-3.60 (1H, m), 3.01 (2H, q, J=7 Hz), 2.26-2.20 (2H, m), 1.50 (6H, s), 1.35 (3H, t, J=7 Hz), 1.09 (3H, t, J=7 Hz); MS (ESI) m/z: 568 [M+H]$^+$.

Example 27

4-(5-{1-[4-(5-Cyclopropyl-1,2,4-oxadiazol-3-yl)phenoxy]propyl}-1,2,4-oxadiazol-3-yl)-2-fluoro-N-[(1R)-2-hydroxy-1-methylethyl]benzamide

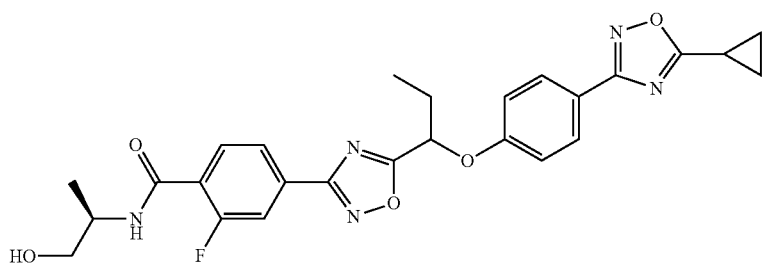 [SMILES: CCC(Oc1ccc(-c2noc(C3CC3)n2)cc1)c1nc(-c2ccc(C(=O)N[C@H](C)CO)c(F)c2)no1]

The synthesis was carried out in the same manner as in Example 7, except that the compound obtained in Reference Example 39 (357 mg, 0.797 mmol) was used in place of 2-fluoro-4-(5-{1-[4-(5-isopropyl-1,2,4-oxadiazol-3-yl)phenoxy]propyl}-1,2,4-oxadiazol-3-yl)benzoic acid. Thus, the title compound (280 mg, yield: 69%) was obtained.

$^1$H-NMR (400 MHz, CDCl$_3$) δ ppm: 8.18 (1H, t, J=8 Hz), 8.00-7.79 (4H, m), 7.05-6.84 (3H, m), 5.48 (1H, t, J=7 Hz), 4.37-4.25 (1H, m), 3.78 (1H, dd, J=11 Hz, 4 Hz), 3.66 (1H, dd, J=11 Hz, 7 Hz), 2.33-2.15 (3H, m), 1.73-1.65 (1H, br-s), 1.32-1.02 (10H, m); MS (ESI) m/z: 509 [M+H]$^+$.

Example 28

(2R)-2-{[4-(5-{1-[4-(5-cyclopropyl-1,2,4-oxadiazol-3-yl)phenoxy]propyl}-1,2,4-oxadiazol-3-yl)-2-fluorobenzoyl]amino}propyl glycinate hydrochloride

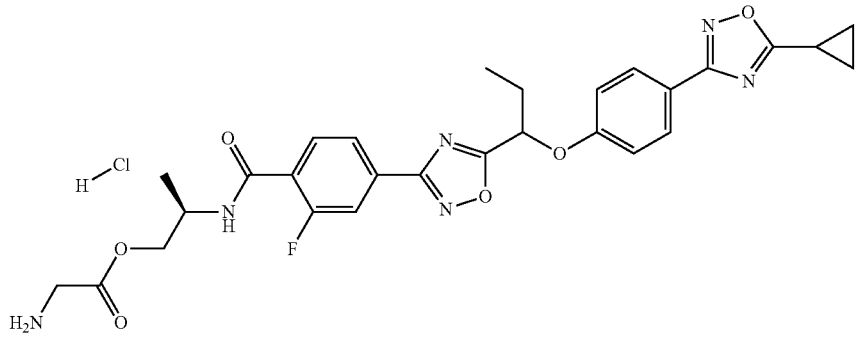

Trifluoroacetic acid (1.00 mL) was added to a methylene chloride (1.00 mL) solution of the compound obtained in Reference Example 40 (260 mg, 0.391 mmol), and the mixture was stirred for one hour at room temperature. A saturated aqueous solution of sodium hydrogen carbonate was added to the reaction mixture, and the mixture was subjected to extraction two times with ethyl acetate. The organic layer thus obtained was washed once with saturated brine, and then was dried over anhydrous sodium sulfate. The solvent was distilled off under reduced pressure, and the resulting residue was purified by silica gel column chromatography (ethyl acetate:methanol=9:1→4:1, v/v). To an ethyl acetate (500 µL) solution of the resulting (2R)-2-{[4-(5-{1-[4-(5-cyclopropyl-1,2,4-oxadiazol-3-yl)phenoxy]propyl}-1,2,4-oxadiazol-3-yl)-2-fluorobenzoyl]amino}propyl glycinate (187 mg, 0.331 mmol), a 4 N hydrochloric acid-ethyl acetate solution (248 (L, 0.994 mmol) was added, and the solvent was distilled off under reduced pressure. Diethyl ether was added to the resulting residue, and the mixture was filtered. Thus, the title compound (170 mg, yield: 72%) was obtained.

$^1$H-NMR (400 MHz, DMSO-d6) (ppm: 8.52 (1H, d, J=8 Hz), 8.34-8.28 (3H, m), 7.93-7.71 (5H, m), 7.25-7.18 (2H, m), 5.99 (1H, t, J=7 Hz), 4.35-4.09 (3H, m), 3.80 (2H, s), 2.43-2.12 (3H, m), 1.30-1.02 (10H, m); MS (ESI) m/z: 566 [M+H]+.

Example 29

(2R)-2-{[2-fluoro-4-(5-{1-[4-(5-isopropyl-1,2,4-oxadiazol-3-yl)phenoxy]propyl}-1,2,4-oxadiazol-3-yl)benzoyl]amino}propyl N,N-dimethylglycinate hydrochloride

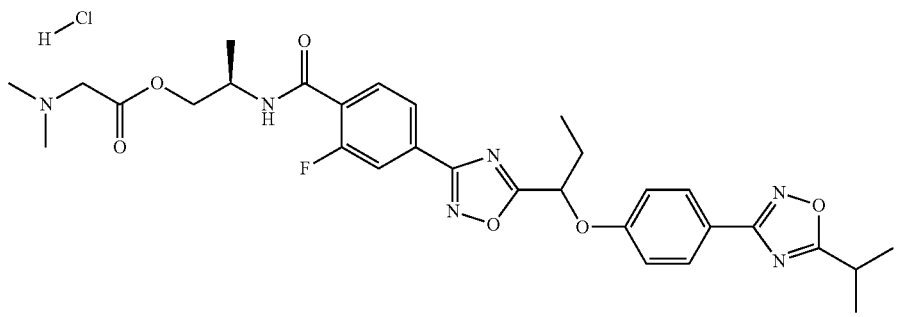

The synthesis was carried out in the same manner as in Reference Example 14, except that N,N-dimethylglycine (68.0 mg, 0.659 mmol) was used in place of N-(tert-butoxycarbonyl)glycine, and thus (2R)-2-{[2-fluoro-4-(5-{1-[4-(5-isopropyl-1,2,4-oxadiazol-3-yl)phenoxy]propyl}-1,2,4-oxadiazol-3-yl)benzoyl]amino}propyl N,N-dimethylglycinate was obtained. A 4 M aqueous hydrochloric acid solution (1.00 mL) was added thereto, and the solvent was distilled off from the reaction mixture under reduced pressure. Thus, the title compound (280 mg, 52%) was obtained.

$^1$H-NMR (400 MHz, DMSO-d$_6$) δ ppm: 10.3-10.2 (1H, br-s), 8.55 (1H, d, J=8 Hz), 7.97-7.71 (5H, m), 7.23 (2H, d, J=8 Hz), 6.00 (1H, t, J=7 Hz), 4.38-3.27 (5H, m), 3.34-3.29 (1H, m), 2.82 (6H, s), 2.23-2.13 (2H, m), 1.18 (6H, d, J=7 Hz), 1.20 (3H, d, J=7 Hz), 1.10-1.00 (3H, m); MS (ESI) m/z: 596 [M+H]$^+$.

Example 30

2-{[2-Fluoro-4-(5-{1-[4-(5-isopropyl-1,2,4-oxadiazol-3-yl)phenoxy]propyl}-1,2,4-oxadiazol-3-yl)benzoyl]amino}ethyl N,N-dimethylglycinate hydrochloride

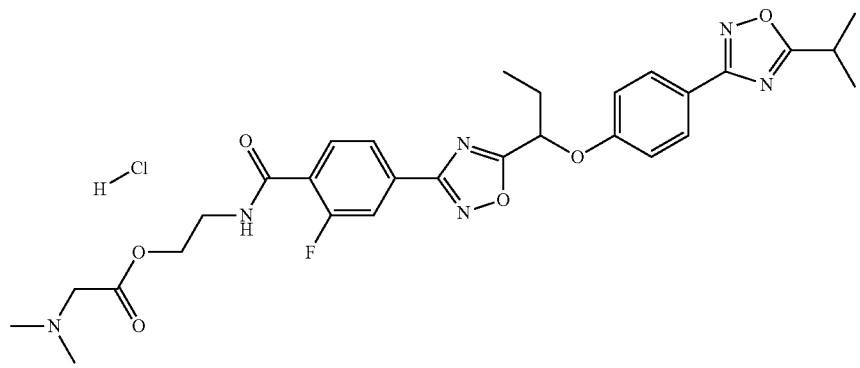 [SMILES: CCC(Oc1ccc(-c2noc(C(C)C)n2)cc1)c1nc(-c2ccc(C(=O)NCCOC(=O)CN(C)C)c(F)c2)no1 ; Cl]

The synthesis was carried out in the same manner as in Example 29, except that the compound obtained in Example 4 (390 mg, 0.787 mmol) was used in place of 2-fluoro-N-[(1R)-2-hydroxy-1-methylethyl]-4-(5-{1-[4-(5-isopropyl-1,2,4-oxadiazol-3-yl)phenoxy]propyl}-1,2,4-oxadiazol-3-yl)benzamide. Thus, the title compound (363 mg, yield: 74%) was obtained.

$^1$H-NMR (400 MHz, DMSO-d$_6$) δ ppm: 10.3-10.2 (1H, br-s), 8.72-8.65 (1H, m), 7.95-7.76 (5H, m), 7.21 (2H, d, J=8 Hz), 5.85 (1H, t, J=7 Hz), 4.29 (2H, t, J=7 Hz), 4.13 (2H, s), 3.58-3.56 (2H, m), 3.28-3.26 (1H, m), 2.80 (6H, s), 2.20-2.13 (2H, m), 1.33 (6H, d, J=7 Hz), 1.03 (3H, t, J=7 Hz); MS (ESI) m/z: 582 [M+H]$^+$.

Compounds of Examples 31 to 66 were obtained by making reference to the Reference Examples and Examples described above.

TABLE 1

| Example | Structural formula | NMR data |
|---|---|---|
| 31 |  | $^1$H-NMR (400 MHz, CDCl$_3$) δ ppm: 8.05-7.83 (4H, m), 7.56-7.48 (1H, m), 7.25-7.18 (2H, m), 5.54 (1H, t, J = 7 Hz), 3.80-3.68 (2H, m), 3.46-3.39 (4H, m), 3.32-3.25 (2H, m), 3.19 (1H, s), 3.02 (2H, s), 2.38-2.20 (2H, m), 1.46 (6H, d, J = 7 Hz), 1.17 (3H, t, J = 7 Hz); MS (FAB$^+$) m/z: 524 [M + H]$^+$. |

TABLE 1-continued

| Example | Structural formula | NMR data |
|---|---|---|
| 32 | | ¹H-NMR (400 MHz, CDCl₃) δ ppm: 8.05-7.83 (4H, m), 7.56-7.48 (1H, m), 7.10-7.09 (2H, m), 5.54 (1H, t, J = 7 Hz), 3.96-3.71 (3.5H, t, J = 7 Hz), 3.41 (0.5H, t, J = 7 Hz), 3.32-3.25 (2H, m), 3.04 (3H, s), 2.38-2.20 (2H, m), 1.47 (6H, d, J = 7 Hz), 1.17 (3H, t, J = 7 Hz). MS (FAB⁺) m/z: 510 [M + H]⁺. |
| 33 | | ¹H-NMR (400 MHz, DMSO-d₆) δ ppm: 8.43-8.35 (1H, M), 7.94-7.92 (5H, m), 7.30-7.26 (2H, m), 5.97 (1H, t, J = 7 Hz), 4.72 (1H, t, J = 6 Hz), 3.52-3.25 (4H, m), 2.62-2.41 (3H, m), 2.20-2.13 (2H, m), 1.02 (3H, t, J = 3 Hz). |
| 34 | | ¹H-NMR (400 MHz, DMSO-d₆) δ ppm: 8.00-7.82 (3H, m), 7.67 (1H, t, J = 7 Hz), 7.27 (2H, d, J = 9 Hz), 6.03 (1H, t, J = 7 Hz), 4.86 (0.75H, t, J = 6 Hz), 4.73 (0.25H, t, J = 6 Hz), 4.21-4.11 (1H, m), 3.69-3.09 (6H, m), 2.26-2.20 (2H, m), 2.00-1.74 (4H, m), 1.39 (6H, d, J = 7 Hz), 1.08 (3H, t, J = 7 Hz). |
| 35 | | ¹H-NMR (400 MHz, DMSO-d₆) δ ppm: 8.00-7.83 (6H, m), 7.28 (2H, d, J = 7 Hz), 6.03 (1H, t, J = 7 Hz), 4.75-4.69 (2H, m), 4.01-3.85 (2H, m), 3.64-3.32 (3H, m), 2.26-2.20 (2H, m), 1.39 (6H, d, J = 7 Hz), 1.13-1.05 (6H, m). |
| 36 | | ¹H-NMR (400 MHz, DMSO-d₆) δ ppm: 8.30 (1H, d, J = 7 Hz), 7.92-7.68 (4H, m), 7.21 (2H, d, J = 8 Hz), 5.97 (1H, t, J = 7 Hz), 4.12-3.99 (1H, m), 3.60-3.25 (5H, m), 2.20-2.13 (2H, m), 1.70-1.50 (2H, m), 1.33 (6H, d, J = 7 Hz), 1.02 (3H, t, J = 7 Hz), 1.00 (3H, d, J = 7 Hz). |

TABLE 1-continued

| Example | Structural formula | NMR data |
|---|---|---|
| 37 | | $^1$H-NMR (400 MHz, DMSO-d$_6$) δ ppm: 8.43 (1H, d, J = 3 Hz) 8.23 (1H, t, J = 8 Hz), 8.23-7.98 (3H, m), 7.39 (1H, dd, J = 9 Hz, 3 Hz), 7.00-6.90 (1H, m), 5.56 (1H, t, J = 7 Hz), 4.40-4.30 (1H, m), 3.84 (1H, dd, J = 10 Hz, 4 Hz), 3.84 (1H, dd, J = 10 Hz, 6 Hz), 3.06-3.04 (2H, m), 2.27-2.55 (4H, m), 1.19 (3H, t, J = 7 Hz), 1.00 (6H, d, J = 7 Hz). |

TABLE 2

| Example | Structural formula | NMR data |
|---|---|---|
| 38 | | $^1$H-NMR (400 MHz, CDCl$_3$) δ ppm: 8.18 (1H, t, J = 8 Hz), 8.07-7.83 (3H, m), 7.87-7.82 (1H, m), 7.10 (2H, d, J = 8 Hz), 6.90-6.82 (1H, m), 5.54 (1H, t, J = 7 Hz), 3.75 (2H, s), 2.83 (2H, d, J = 7 Hz), 2.37-2.20 (3H, m), 1.46 (6H, s), 1.18 (3H, t, J = 7 Hz), 1.06 (6H, d, J = 7 Hz). |
| 39 | | $^1$H-NMR (400 MHz, CDCl$_3$) δ ppm: 8.30 (1H, s), 8.24 (1H, t, J = 8 Hz), 8.03-7.87 (3H, m), 7.02 (1H, d, J = 7 Hz), 6.95-6.91 (1H, m), 5.54 (1H, t, J = 7 Hz), 4.41-4.31 (1H, m), 3.86-3.63 (2H, m), 3.31-3.26 (1H, m), 2.45-2.25 (2H, m), 1.75-1.50 (1, br-s), 1.46 (6H, d, J = 7 Hz), 1.35 (3H, d, J = 7 Hz), 1.23 (3H, t, J = 7 Hz); MS (FAB$^+$) m/z: 588 [M + H]$^+$. |
| 40 | | $^1$H-NMR (400 MHz, CDCl$_3$) δ ppm: 8.16 (1H, t, J = 8 Hz), 7.95-7.80 (4H, m), 7.03 (2H, d, J = 8 Hz), 6.82-6.79 (1H, m), 5.48 (1H, t, J = 7 Hz), 4.30-4.17 (1H, br-s), 3.70 (2H, s), 2.31-2.10 (3H, m), 1.70-1.50 (1H, br-s), 1.55 (6H, s), 1.41-1.10 (6H, m); MS (FAB$^+$) m/z: 523 [M + H]$^+$. |

TABLE 2-continued

| Example | Structural formula | NMR data |
|---|---|---|
| 41 | | $^1$H-NMR (400 MHz, CDCl$_3$) δ ppm: 8.16 (1H, t, J = 8 Hz), 7.95-7.80 (4H, m), 7.03 (2H, d, J = 8 Hz), 6.82-6.79 (1H, m), 5.71 (1H, q, J = 7 Hz), 4.30-4.17 (1H, br-s), 3.70 (2H, s), 1.89 (3H, d, J = 7 Hz), 1.70-1.50 (1H, br-s), 1.55-1.52 (12H, m). |
| 42 | | $^1$H-NMR (400 MHz, CDCl$_3$) δ ppm: 8.22 (1H, t, J = 8 Hz), 8.07-7.99 (3H, m), 7.86 (1H, dd, J = 12 Hz, 1 Hz), 7.12-6.94 (3H, m), 5.53 (1H, t, J = 7 Hz), 4.47-4.39 (1H, m), 3.58-3.46 (2H, m), 3.43 (3H, s), 3.32 (1H, m), 2.37-2.22 (2H, m), 1.46 (6H, d, J = 7 Hz), 1.33 (3H, d, 8 Hz), 1.17 (3H, t, J = 7 Hz). |
| 43 | | $^1$H-NMR (400 MHz, DMSO-d$_6$) δ ppm: 8.10 (1H, s), 7.95-7.65 (5H, m), 7.23 (2H, d, J = 8 Hz), 5.99 (1H, t, J = 7 Hz), 4.40 (2H, s), 3.82 (2H, s), 3.29-3.27 (3H, m), 2.60 (3H, s), 2.20-2.10 (2H, m), 1.35 (6H, s), 1.04 (3H, t, J = 7 Hz). |
| 44 | | $^1$H-NMR (400 MHz, DMSO-d$_6$) δ ppm: 8.40-8.30 (2H, br-s), 7.98 (1H, s), 7.91 (2H, d, J = 8 Hz), 7.90-7.84 (2H, m) 7.47 (1H, d, J = 8 Hz), 7.27 (2H, d, J = 8 Hz), 6.02 (1H, t, J = 7 Hz), 4.47 (2H, s), 3.89 (2H, s), 3.35-3.30 (1H, m), 2.30 (3H, s), 2.25-2.21 (2H, m), 1.37-1.36 (12H, m), 1.10-1.06 (3H, m). MS (FAB$^+$) m/z: 578 [M + H]$^+$. |

TABLE 3

| Example | Structural formula | NMR data |
|---|---|---|
| 45 | | $^1$H-NMR (400 MHz, DMSO-d$_6$) δ ppm: 8.30-8.20 (2H, br-s), 7.92-7.81 (5H, m), 7.62-7.56 (1H, m), 7.22-7.19 (2H, m), 5.98 (1H, t, J = 7 Hz), 4.40-4.18 (2H, m), 3.78-3.73 (4H, m), 3.48-3.42 (1H, m), 3.01 (1.5H, s), 2.87 (1.5H, s), 2.20-2.14 (2H, m), 1.33 (6H, d, J = 7 Hz), 1.02 (3H, t, J = 7 Hz). |
| 46 | | $^1$H-NMR (400 MHz, DMSO-d$_6$) δ ppm: 8.49-8.22 (3H, m), 7.92-7.73 (5H, m), 7.22-7.19 (2H, m), 5.98 (1H, t, J = 7 Hz), 4.27-4.10 (4H, m), 3.79 (2H, s), 2.60 (3H, s), 2.20-2.14 (2H, m), 1.16 (3H, d, J = 7 Hz), 1.04 (3H, t, J = 7 H). |
| 47 | | $^1$H-NMR (400 MHz, DMSO-d$_6$) δ ppm: 8.50-7.50 (8H, m), 7.22-7.19 (2H, m), 5.98 (1H, t, J = 7 Hz), 4.27-4.10 (4H, m), 3.79 (2H, s), 2.47 (3H, s), 2.20-2.14 (2H, m), 1.16 (3H, d, J = 7 Hz), 1.01 (3H, t, J = 7 Hz). |
| 48 | | $^1$H-NMR (400 MHz, DMSO-d$_6$) δ ppm: 8.55-8.43 (3H, m), 7.92-7.71 (4H, m), 7.20 (2H, d, J = 8 Hz), 5.97 (1H, t, J = 7 Hz), 4.26-4.11 (3H, m), 3.78-3.76 (2H, m), 2.82 (2H, d, J = 7 Hz), 2.17-2.08 (3H, m), 1.19-0.92 (12H, m). |
| 49 | | $^1$H-NMR (400 MHz, DMSO-d$_6$) δ ppm: 8.57-8.43 (3H, m), 7.92-7.71 (4H, m), 7.20 (2H, d, J = 8 Hz), 5.97 (1H, t, J = 7 Hz), 4.26-4.11 (3H, m), 3.78-3.76 (2H, m), 2.82 (2H, d, J = 7 Hz), 2.17-2.08 (3H, m), 1.19-0.92 (12H, m). |

TABLE 3-continued

| Example | Structural formula | NMR data |
|---|---|---|
| 50 | | ¹H-NMR (400 MHz, CDCl₃) δ ppm: 8.60-8.58 (2H, br-s), 7.98-7.65 (5H, m), 7.24 (2H, d, J = 8 Hz), 6.76-6.71 (1H, m), 5.46 (1H, t, J = 7 Hz), 4.46 (2H, s), 3.97 (2H, s), 2.78 (2H, d, J = 7 Hz), 2.28-2.04 (5H, m), 1.42 (6H, s), 1.13 (3H, t, J = 7 Hz), 1.01 (6H, d, J = 7 Hz). |
| 51 | | ¹H-NMR (400 MHz, CD₃OD) δ ppm: 7.97-7.73 (7H, m), 7.14-7.12 (3H, m), 5.76 (1H, t, J = 7 Hz), 4.56 (1H, d, J = 7 Hz), 4.21-4.17 (3H, m), 3.80 (2H, s), 2.25-1.90 (4H, m), 1.08 (6H, d, J = 7 Hz), 1.07 (6H, d, J = Hz), 1.10 (3H, t, J = 7 Hz). |

TABLE 4

| Example | Structural formula | NMR data |
|---|---|---|
| 52 | | ¹H-NMR (400 MHz, DMSO-d₆) δ ppm: 8.50-8.35 (4H, m), 7.92-7.71 (5H, m), 7.24 (2H, d, J = 8 Hz), 5.97 (1H, t, J = 7 Hz), 4.26-4.11 (3H, m), 3.78 (2H, s), 2.97 (2H, q, J = 7 Hz), 2.17-2.08 (2H, m), 1.66-1.40 (2H, m), 1.30 (3H, t, J = 7 Hz), 1.04 (3H, t, J = 7 Hz), 0.91 (3H, t, J = 7 Hz); MS (FAB⁺) m/z: 568 [M + H]⁺. |
| 53 | | ¹H-NMR (400 MHz, CD₃OD) δ ppm: 7.98-7.75 (5H, m), 7.16-7.14 (2H, m), 5.78 (1H, t, J = 7 Hz), 4, 58 (1H, q, J = 7 Hz), 4.25-4.14 (2H, m), 3.84-3.83 (2H, m), 3.29 (4H, m), 2.95 (2H, q, J = 7 Hz), 2.28-2.21 (2H, m), 1.99-1.91 (1H, m), 1.39 (3H, t, J = 7 Hz), 1.15-1.00 (9H, m). |

TABLE 4-continued

| Example | Structural formula | NMR data |
|---|---|---|
| 54 | | $^1$H-NMR (400 MHz, CD$_3$OD) δ ppm: 8.42-8.40 (1H, m), 7.99-7.70 (8H, m), 7.16-7.10 (2H, m), 5.76 (1H, t, J = 7 Hz), 4.44 (1H, dd, J = 10 Hz, 5 Hz), 4.33-4.22 (1H, m), 4.15 (1H, dd, J = 10 Hz, 7 Hz), 3.85 (2H, s), 2.93 (2H, q, J = 8 Hz), 2.29-2.15 (2H, m), 1.73-1.49 (2H, m), 1.37 (3H, t, J = 8 Hz), 1.10 (3H, t, J = 7 Hz), 1.02 (3H, t, J = 7 Hz). |
| 55 | | $^1$H-NMR (400 MHz, DMSO-d$_6$) δ ppm: 8.24-8.15 (3H, m), 7.90-7.67 (5H, m), 7.21 (2H, d, J = 7 Hz), 5.98 (1H, t, J = 7 Hz), 4.40 (2H, s), 3.84 (2H, s), 2.39-2.14 (4H, m), 1.36 (6H, s), 1.27-1.01 (7H, m); MS (FAB$^+$) m/z: 580 [M + H]$^+$. |
| 56 | | $^1$H-NMR (400 MHz, DMSO-d$_6$) δ ppm: 8.24-8.15 (3H, m), 7.02-7.74 (5H, m), 7.21 (2H, d, J = 7 Hz), 6.21 (1H, q, J = 7 Hz), 4.45 (2H, s), 3.89 (2H, s), 3.39-3.14 (2H, m), 1.86 (3H, d, J = 7 Hz), 1.40-1.30 (12H, m). |
| 57 | | $^1$H-NMR (400 MHz, CD$_3$OD) δ ppm: 8.01-7.79 (5H, m), 7.18 (2H, d, J = 8 Hz), 5.82 (1H, t, J = 7 Hz), 4.80-4.75 (4H, m), 4.51 (1H, dd, J = 10 Hz, 4 Hz), 4.38-4.29 (1H, m), 4.27 1H, dd, J = 10 Hz, 7 Hz), 3.87 (2H, s), 2.34-2.26 (3H, m), 1.78-1.58 (2H, m), 1.33-1.23 (4H, m), 1.16 (3H, t, J = 7 Hz), 1.08 (3H, t, J = 7 Hz). |
| 58 | | $^1$H-NMR (400 MHz, CD$_3$OD) δ ppm: 8.04-7.79 (5H, m), 7.218 (2H, d, J = 8 Hz), 6.02 (1H, q J = 7 Hz), 4.80-4.75 (4H, m), 4.51 (1H, dd, J = 10 Hz, 4 Hz), 4.38-4.29 (1H, m), 4.27 (1H, dd, J = 10 Hz, 7 Hz), 3.88 (2H, s), 3.47-3.42 (1H, m), 1.91 (3H, d, J = 7 Hz), 1.78-1.59 (2H, m), 1.46 (6H, d, J = 7 Hz), 1.07 (3H, t, J = 7 Hz). |

TABLE 5

| Example | Structural formula | NMR data |
|---|---|---|
| 59 | | ¹H-NMR (400 MHz, DMSO-d₆) δ ppm: 8.84-8.55 (3H, m), 7.94-7.74 (5H, m), 7.23 (2H, d, J = 8 Hz), 6.00 (1H, q, J = 7 Hz), 4.37-4.02 (4H, m), 3.39-3.34 (1H, m), 2.22-2.15 (2H, m), 1.40 (3H, d, J = 7 Hz), 1.34 (6H, d, J = 7 Hz), 1.22-1.19 (4H, m), 1.04 (3H, t, J = 7 Hz); MS (FAB⁺) m/z: 582 [M + ]⁺. |
| 60 | | ¹H-NMR (400 MHz, DMSO-d₆) δ ppm: 8.58-8.45 (3H, m), 7.94-7.73 (5H, m), 7.23 (2H, d, J = 8 Hz), 6.00 (1H, t, J = 7 Hz), 4.32-4.13 (3H, m), 3.90 (1H, d, J = 4 Hz), 3.39-3.34 (1H, m), 2.24-2.13 (3H, m), 1.35 (6H, d, J = 7 Hz), 1.25-1.19 (4H, m), 1.06-0.82 (9H, m); MS (FAB⁺) m/z: 610 [M + H]⁺. |
| 61 | | ¹H-NMR (400 MHz, CD₃OD) δ ppm: 7.97-7.73 (9H, m), 7.14-7.12 (2H, m), 5.95 (1H, q, J = 7 Hz), 4.53-4.09 (3H, m), 3.82 (2H, s), 3.43-3.41 (1H, m), 1.84 (3H, d, J = 7 Hz), 1.39 (6H, d, J = 7 Hz) 1.26 (3H, d, J = 7 Hz). |
| 62 | | ¹H-NMR (400 MHz, DMSO-d₆) δ ppm: 8.52-8.50 (1H, m), 7.94-7.73 (5H, m), 7.23 (2H, d, J = 8 Hz), 6.00 (1H, t, J = 7 Hz), 4.40-4.05 (4H, m), 3.34-3.15 (2H, m), 2.27-1.86 (6H, m), 1.35 (6H, d, J = 7 Hz), 1.25-1.15 (4H, m), 1.04 (3H, t, J = 7 Hz). |
| 63 | | ¹H-NMR (400 MHz, DMSO-d₆) δ ppm: 9.00-8.93 (2H, br-s), 8.54 (1H, d, J = 8 Hz), 7.94-7.77 (5H, m), 7.23 (2H, d, J = 8 Hz), 5.99 (1H, t, J = 7 Hz), 4.54 (1H, t, J = 6 Hz), 4.34-4.17 (3H, m), 3.35-3.19 (4H, m), 2.22-2.15 (2H, m), 1.38 (6H, d, J = 7 Hz), 1.28-1.20 (3H, m), 1.04 (3H, t, J = 7 Hz). |

TABLE 5-continued

| Example | Structural formula | NMR data |
|---|---|---|
| 64 | | ¹H-NMR (400 MHz, CDCl$_3$) δ ppm: 8.16 (1H, t, J = 8 Hz), 8.03-7.99 (3H, m), 7.61-7.55 (2H, m), 7.25-7.09 (3H, m), 5.37 (1H, t, J = 7 Hz), 3.89 (2H, t, J = 5 Hz), 3.70 (2H, q, J = 5 Hz), 3.30-3.25 (1H, m), 2.31-2.07 (2H, m), 1.53-1.50 (1H, m), 1.46 (6H, d, J = 7 Hz), 1.12 (3H, t, J = 7 Hz) MS (FAB⁺) m/z: 495 [M + H]⁺. |
| 65 | | ¹H-NMR (400 MHz, CDCl$_3$) δ ppm: 8.10 (1H, t, J = 8 Hz), 8.03-7.99 (3H, m), 7.61-7.55 (2H, m), 7.15-7.09 (2H, m), 6.87-6.85 (1H, m), 5.37 (1H, t, J = 7 Hz), 3.74 (2H, t, J = 5 Hz), 3.30-3.25 (1H, m), 2.31-2.14 (2H, m), 1.53-1.50 (1H, m), 1.47-1.45 (12H, m), 1.12 (3H, t, J = 7 Hz). MS (FAB⁺) m/z: 523 [M + H]⁺. |

TABLE 6

| Example | Structural formula | NMR data |
|---|---|---|
| 66 | | ¹H-NMR (400 MHz, DMSO-d$_6$) δ ppm: 8.48-8.30 (2H, m), 8.00-7.92 (3H, m), 7.73-7.61 (3H, m), 7.25 (2H, d, J = 9 Hz), 5.69 (1H, t, J = 7 Hz), 4.44 (2H, s), 3.86 (2H, s), 2.22-2.12 (2H, m), 1.41 (6H, s), 1.39 (6H, d, J = 7 Hz), 1.09-1.02 (6H, m). MS (FAB⁺) m/z: 580 [M + H]⁺. |

Example 67

2-Fluoro-N-[(1R)-2-hydroxy-1-methylethyl]-4-(5-{(1R)-1-[4-(5-isopropyl-1,2,4-oxadiazol-3-yl)phenoxy]propyl}-1,2,4-oxadiazol-3-yl)benzamide To an N,N-dimethylformamide (2 mL) solution of the compound obtained in Reference Example 47 (100 mg, 0.222 mmol), 1-hydroxybenzotriazole monohydrate (29.9 mg, 0.222 mmol), N-(3-dimethylaminopropyl)-N'-ethylcarbodiimide (127.4 mg, 0.665 mol) and (R)-2-amino-1-propanol (24.9 mg, 0.332 mol) were added at room temperature, and the mixture was stirred for 3 hours at the same temperature. Subsequently, water was added to the reaction mixture, and the mixture was subjected to extraction once with ethyl acetate. The organic layer thus obtained was washed with water and 10% brine, and then was dried over anhydrous sodium sulfate. The solvent was distilled off under reduced pressure, and the resulting residue was purified by silica gel column chromatography (hexane:ethyl acetate=50:50→30:70, v/v). Thus, the title compound (92.9 mg, yield: 83%) was obtained.

¹H-NMR (500 MHz, CDCl$_3$) δ ppm: 8.20 (1H, t, J=8 Hz), 8.01-7.98 (3H, m), 7.86 (1H, dd, J=12, 2 Hz), 7.06 (2H, dd, J=12, 3 Hz), 6.90 (1H, dd, J=12, 8 Hz), 5.51 (1H, t, J=7 Hz), 4.37-4.32 (1H, m), 3.81 (1H, dd, J=11, 3 Hz), 3.68 (1H, dd, J=11, 6 Hz), 3.30-3.21 (1H, m), 2.43 (1H, s), 2.31-2.23 (2H, m), 1.43 (6H, d, J=7 Hz), 1.32 (3H, d, J=7 Hz), 1.15 (3H, t, J=8 Hz); MS (FAB$^+$) m/z: 510 [M+H]$^+$.

Example 68

N-(cyclopropylmethyl)-2-fluoro-4-(5-{(1R)-1-[4-(5-isopropyl-1,2,4-oxadiazol-3-yl)phenoxy]propyl}-1,2,4-oxadiazol-3-yl)benzamide

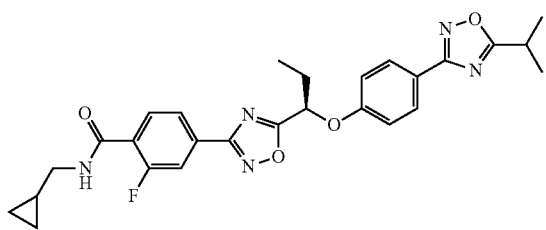 [SMILES: CC[C@@H](Oc1ccc(-c2noc(C(C)C)n2)cc1)c1nc(-c2ccc(C(=O)NCC3CC3)c(F)c2)no1]

To a dichloromethane (2 mL) solution of the compound obtained in Reference Example 47 (103 mg, 0.228 mmol), 1-hydroxybenzotriazole monohydrate (34.9 mg, 0.228 mmol), N-(3-dimethylaminopropyl)-N'-ethylcarbodiimide (65.5 mg, 0.342 mmol) and cyclopropylmethylamine (40 μL, 0.46 mmol) were added at room temperature, and the mixture was stirred for 30 minutes at the same temperature. Subsequently, water was added to the reaction mixture, and the mixture was subjected to extraction three times with dichloromethane. The organic layer thus obtained was washed with a saturated aqueous solution of sodium hydrogen carbonate, and then was dried over anhydrous sodium sulfate. The solvent was distilled off under reduced pressure, and the resulting residue was purified by silica gel column chromatography (hexane:ethyl acetate=95:5→50:50, v/v). Thus, the title compound (73.5 mg, yield: 64%) was obtained.

$^1$H-NMR (400 MHz, CDCl$_3$) δ ppm: 8.22 (1H, t, J=8 Hz), 8.01 (2H, d, J=9 Hz), 7.97-8.00 (1H, m), 7.86 (1H, d, J=13 Hz), 7.06 (2H, d, J=9 Hz), 6.82-6.90 (1H, m), 5.51 (1H, t, J=6 Hz), 3.36 (2H, dd, J=7, 7 Hz), 3.29-3.22 (1H, m), 2.34-2.20 (2H, m), 1.44 (6H, d, J=7 Hz), 1.15 (3H, t, J=7 Hz), 1.15-1.02 (1H, m), 0.61-0.56 (2H, m), 0.30 (2H, dd, J=11, 5 Hz); MS (FAB$^+$) m/z: 506 [M+H]$^+$.

Formulation Example 5 g of each of the compounds obtained in the Examples, 90 g of lactose, 34 g of corn starch, 20 g of crystalline cellulose, and 1 g of magnesium stearate are mixed with a blender, and then the blend is tabletted with a tabletting machine. Thereby, tablets are obtained.

Test Example 1

Mouse oGTT (Oral Glucose Tolerance Test 2.0 to 10.0 mg of a test compound was weighed, and then a 0.5 w/v % methyl cellulose solution was added thereto to prepare a 1 mg/mL liquid for administration. Alternatively, 1.0 to 10.0 mg of a test compound was weighed, and then N,N-dimethylformamide was added thereto to prepare a 20 mg/mL compound solution. This was further diluted to 20 times using a 0.5 w/v % methyl cellulose solution, and thereby a liquid for administration at a final concentration of 1 mg/mL was prepared. C57/BL6J mice (male, 6 to 8 weeks old) were purchased from Charles River Laboratories Japan, Inc., and were raised until they were 9 to 13 weeks old. The mice were fasted, starting from a time point between the 17$^{th}$ hour and the 18$^{th}$ hour of the day before the test day, and were continuously fasted until the test. On the test day, blood was collected from the caudal vein, and then the liquid for administration previously prepared was orally administered. Blood was collected again from the caudal vein thirty minutes after the administration (the blood sugar level at this time is designated as a pre-value). Subsequently, a 30% glucose solution was orally administered in an amount of 10 mL/kg, and thereby, the mice were subjected to glucose load. After the glucose load, blood was collected from the caudal vein at time points of 15, 30, 60 and 120 minutes. Each of the collected blood samples was centrifuged to separate blood plasma. The pre-value, and the blood glucose level values at 15, 30 60 and 120 minutes after the glucose load were measured with a Glucoloader GXT (A&T Corp.) using the separated blood plasma samples, and the decrease rate (%) of the blood sugar level AUC with respect to a vehicle-administered group was calculated. Meanwhile, the vehicle-administered group was administered with a 0.5 w/v % methyl cellulose solution or a 5% v/v N,N-dimethylformamide/0.5 w/v % methyl cellulose mixed solution.

As a result, the compounds of Examples 5, 7, 14, 47 to 49, 52, 57, 58 and 64 decreased the AUC by 5% or more and less than 20%, and the compounds of Examples 1, 4, 6, 8, 10 to 13, 15 to 19, 23 to 26, 28, 31, 33, 43 to 45, 55 to 56, 61 to 63 and 66 to 68 decreased the AUC by 20% or more.

Test Example 2

Rat oGTT (Oral Glucose Tolerance Test) and Test for Measuring Compound Concentration in Rat Blood A test compound is weighed, and then a suspension liquid thereof is prepared using a 0.5 w/v % methyl cellulose solution. Zucker Fatty rats and Zucker Diabetic Fatty rats (male, 8 to 20 weeks old) are purchased from Charles River Laboratories Japan, Inc., and before the test, grouping of the rats is carried out on the basis of the blood sugar levels and body weights of the administered groups. The rats are fasted, starting from a time point between the 15$^{th}$ hour and the 18$^{th}$ hour of the day before the test day, and are continuously fasted until the test. On the test day, blood is collected from the caudal vein, and then the suspension liquid previously prepared is orally administered. Blood is collected again from the caudal vein thirty minutes after the administration (the blood sugar level at this time is designated as a pre-value). Subsequently, a 50% glucose solution is orally administered in an amount of 4 mL/kg, and thereby, the rats are subjected to glucose load. After the glucose load, blood is collected from the caudal vein at time points of 30 minutes, 1, 2 and 3 hours. Each of the collected blood samples is centrifuged to separate blood plasma. The pre-value, and the blood glucose level values at 30 minutes, 1, 2 and 3 hours after the glucose load are measured with a Glucoloader GXT (A&T Corp.) using the separated blood plasma samples, and the decrease rate (%) of the blood sugar level AUC with respect to a vehicle-administered group is calculated. Meanwhile, the vehicle-administered group is administered with a 0.5 w/v % methyl cellulose solution.

The blood plasma samples obtained by the method described above are used for the measurement of the plasma concentration of the test compound. In order to measure the plasma concentration of the test compound for a day, blood is collected 4 hours to 8 hours after the administration, and even after 24 hours. The blood plasma is subjected to protein removal, and then is fed to a liquid chromatography/mass analyzer to calculate the compound concentration in the blood plasma.

Test Example 3

Test on Protection of β Cells (Pancreas)

The β cell (pancreas)-protecting action of a test compound can be confirmed by making reference to the method described in Junko Ogawa, et al., Life Sciences, Vol. 65, No. 12, pp. 1287-1296 (1999).

INDUSTRIAL APPLICABILITY

The compound of the present invention or a pharmaceutically acceptable salt thereof is useful as an active ingredient of a pharmaceutical composition for treating and/or preventing type 1 diabetes, type 2 diabetes, gestational diabetes, hyperglycemia due to other factors, impaired glucose tolerance, diabetes-associated diseases, diabetic complications and the like, and for protecting β cells or the pancreas.

The invention claimed is:
1. A compound represented by formula (I):

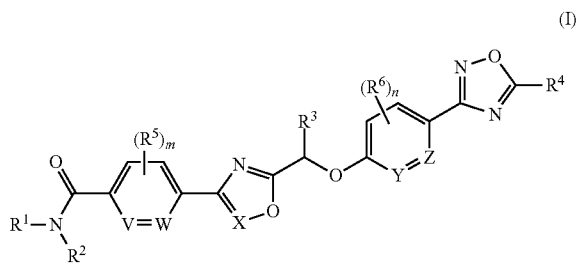

(I)

wherein $R^1$ represents a hydrogen atom, or the C1-C6 alkyl group substituted with one or two substituents selected from a substituent subgroup α;
the substituent subgroup α is the group consisting of a C1-C6 alkoxy group, a C1-C6 alkoxycarbonyl group, a hydroxyl group which may be substituted with a substituent selected from a substituent subgroup β, and a carboxyl group;
the substituent subgroup β is the group consisting of a C1-C6 alkylcarbonyl group substituted with one or two substituents selected from a substituent subgroup γ, and a 4- to 6-membered heterocyclic carbonyl group which may be substituted with one C1-C6 alkyl group;
the substituent subgroup γ is the group consisting of a hydroxyl group, an amino group, a (C1-C6 alkyl)amino group, a di(C1-C6 alkyl)amino group, a carbamoyl group, a phenyl group and a 4- to 6-membered heterocyclic group;
$R^2$ represents a hydrogen atom, or a C1-C6 alkyl group which may be substituted with one hydroxyl group;
or $R^1$ and $R^2$, together with the nitrogen atom to which $R^1$ and $R^2$ are bonded, may be joined to form an azetidino group, a pyrrolidino group or a morpholino group, wherein the azetidino group, pyrrolidino group or morpholino group may be substituted with one hydroxyl group or one hydroxy-C1-C6 alkyl group;

$R^3$ and $R^4$ each independently represent a C1-C6 alkyl group;
$R^5$ represents a halogen atom or a C1-C6 alkyl group;
$R^6$ represents a halogen atom;
m and n each independently represent an integer from 0 to 4; and
V, W, X, Y and Z each independently represent CH or N, or a pharmaceutically acceptable salt thereof.

2. The compound according to claim 1, wherein Y and Z both represent CH.

3. The compound according to claim 1, wherein V and W both represent CH.

4. The compound according to claim 1, wherein X represents N.

5. The compound according to claim 1, wherein $R^1$ represents a C1-C4 alkyl group substituted with one or two hydroxyl groups.

6. The compound according to claim 1, wherein $R^1$ represents a hydroxyethyl group, a hydroxyisopropyl group, a hydroxy-1,1-dimethylethyl group, or a 2-hydroxy-1-(hydroxymethyl)ethyl group.

7. The compound according to claim 1, wherein $R^1$ represents a C1-C4 alkyl group substituted with one substituent selected from the substituent subgroup α, wherein the substituent subgroup α is a hydroxyl group substituted with one substituent selected from the substituent subgroup β, the substituent subgroup β is a C1-C4 alkylcarbonyl group substituted with one substituent selected from the substituent subgroup γ, and the substituent subgroup γ is an amino group.

8. The compound according to claim 1, wherein $R^1$ represents an aminomethylcarbonyloxyethyl group, an aminomethylcarbonyloxyisopropyl group, or an aminomethylcarbonyloxy-1,1-dimethylethyl group.

9. The compound according to claims 1, wherein $R^2$ represents a hydrogen atom.

10. The compound according to claim 1, wherein $R^3$ represents a C1-C3 alkyl group.

11. The compound according to claim 1, wherein $R^3$ represents an ethyl group.

12. The compound according to claim 1, wherein $R^4$ represents a C1-C3 alkyl group.

13. The compound according to claim 1, wherein $R^4$ represents an ethyl group or an isopropyl group.

14. The compound according to claim 1, wherein $R^5$ represents a halogen atom, and m represents 1.

15. The compound according to claim 1, wherein $R^5$ represents a fluorine atom, and m represents 1.

16. The compound according to claim 1, wherein n represents 0.

17. A compound selected from the group consisting of the following compounds:
2-fluoro-N-(2-hydroxyethyl)-4-(5-{1-[4-(5-isopropyl-1,2,4-oxadiazol-3-yl)phenoxy]propyl}-1,2,4-oxadiazol-3-yl)benzamide,
2-fluoro-N-[(1R)-2-hydroxy-1-methylethyl]-4-(5-1{-[4-(5-isopropyl-1,2,4-oxadiazol-3-yl)phenoxy]propyl}-1,2,4-oxadiazol-3-yl)benzamide,
2-fluoro-N-(2-hydroxy-1,1-dimethylethyl)-4-(5-{1-[4-(5-isopropyl-1,2,4-oxadiazol-3-yl)phenoxy]propyl}-1,2,4-oxadiazol-3-yl)benzamide,
(2R)-2-{[2-fluoro-4-(5-{1-[4-(5-isopropyl-1,2,4-oxadiazol-3-yl)phenoxy]propyl}-1,2,4-oxadiazol-3-yl)benzoyl]amino}propyl glycinate hydrochloride,
2-{[2-fluoro-4-(5-{1-[4-(5-isopropyl-1,2,4-oxadiazol-3-yl)phenoxy]propyl}-1,2,4-oxadiazol-3-yl)benzoyl]amino}-2-methylpropyl glycinate hydrochloride, 2-fluoro-N-[(1S)-2-hydroxy-1-methylethyl]-4 (2-{1-[4 (5 isopropyl-1,2,4-oxadiazol-3-yl)phenoxy]propyl}-1,3-oxazol-4-yl)benzamide, (2S)-2-{[2-fluoro-4 (2-{1-[4 (5 isopropyl-1,2,4-oxadiazol-3-yl)phenoxy]propyl}-1,3-oxazol-4-yl)benzoyl] amino}propyl glycinate hydrochloride, 4-(5-{1-[4-(5-ethyl-1,2,4-oxadiazol-3-yl)phenoxy]propyl}-1,2,4-oxadiazol-3-yl)-2-fluoro-N-[(1S)-2-hydroxy-1-methylethyl]benzamide, (2S)-2-{[4-(5-{1-[4-(5-ethyl-1,2,4-oxadiazol-3-yl)phenoxy]propyl}-1,2,4-oxadiazol-3-yl)-2-fluorobenzoyl] amino}propyl glycinate hydrochloride, 2-fluoro-N-[(1R)-2-hydroxy-1-methylethyl]-4-(5-{(1R)-1-[4-(5-isopropyl-1,2,4-oxadiazol-3-yl)phenoxy]propyl}-1,2,4-oxadiazol-3-yl)benzamide, and N-(cyclopropylmethyl)-2-fluoro-4-(5-{(1R)-1-[4-(5-isopropyl-1,2,4-oxadiazol-3-yl)phenoxy]propyl}-1,2,4-oxadiazol-3-yl)benzamide.

18. A pharmaceutical composition comprising, the compound according to claim 1, or a pharmaceutically acceptable salt thereof.

19. A method for treating type I diabetes, type 2 diabetes, a diabetes-associated disease, or obesity, the method comprising administering to a mammal a pharmacologically effective amount of the compound according to claim 1 or a pharmaceutically acceptable salt thereof.

20. The method according to claim 19, wherein the mammal is a human being.

21. A method for protecting β cells or the pancreas, the method comprising administering to a mammal a pharmacologically effective amount of the compound according to claim 1 or a pharmaceutically acceptable salt thereof.

22. The method according to claim 21, wherein the mammal is a human being.

* * * * *